US009885092B2

(12) United States Patent
Lowe et al.

(10) Patent No.: US 9,885,092 B2
(45) Date of Patent: Feb. 6, 2018

(54) MATERIALS AND METHODS FOR DETECTION OF HPV NUCLEIC ACIDS

(75) Inventors: Brian Lowe, Olney, MD (US); Anna K. Fulbright, Columbia, MD (US); Irina Nazarenko, Gaithersburg, MD (US)

(73) Assignee: QIAGEN GAITHERSBURG INC., Gaithersburg, MD (US)

( * ) Notice: Subject to any disclaimer, the term of this patent is extended or adjusted under 35 U.S.C. 154(b) by 644 days.

(21) Appl. No.: 13/403,759

(22) Filed: Feb. 23, 2012

(65) Prior Publication Data

US 2012/0322049 A1 Dec. 20, 2012

Related U.S. Application Data

(60) Provisional application No. 61/446,306, filed on Feb. 24, 2011, provisional application No. 61/486,118, filed on May 13, 2011.

(51) Int. Cl.
*C12P 19/34* (2006.01)
*C12Q 1/70* (2006.01)
*C12Q 1/68* (2006.01)

(52) U.S. Cl.
CPC ........... *C12Q 1/708* (2013.01); *C12Q 1/6825* (2013.01)

(58) Field of Classification Search
CPC ............ C12Q 1/6825; C12Q 2563/131; C12Q 1/6804; C12Q 1/701; C12Q 1/708
USPC ......................................... 456/91.2; 435/91.2
See application file for complete search history.

(56) References Cited

U.S. PATENT DOCUMENTS

| | | | |
|---|---|---|---|
| 4,486,536 A | | 12/1984 | Baker et al. |
| 4,486,539 A | | 12/1984 | Ranki et al. |
| 4,563,417 A | | 1/1986 | Alabrella et al. |
| 4,563,419 A | | 1/1986 | Ranki et al. |
| 4,689,294 A | | 8/1987 | Boguslawski et al. |
| 4,731,325 A | | 3/1988 | Palva et al. |
| 4,732,847 A | | 3/1988 | Stuart et al. |
| 4,743,535 A | | 5/1988 | Carrico |
| 4,751,177 A | | 6/1988 | Stabinsky et al. |
| 4,775,619 A | | 10/1988 | Urdea |
| 4,833,084 A | | 5/1989 | Carrico |
| 4,851,330 A | | 7/1989 | Kohne et al. |
| 4,865,980 A | | 9/1989 | Stuart et al. |
| 4,868,105 A | | 9/1989 | Urdea et al. |
| 4,889,798 A | | 12/1989 | Rabbani |
| 4,894,325 A | | 1/1990 | Englehardt et al. |
| 5,082,830 A | | 1/1992 | Brakel et al. |
| 5,106,727 A | | 4/1992 | Hartley et al. |
| 5,116,734 A | | 5/1992 | Higgs et al. |
| 5,200,313 A | | 4/1993 | Carrico |
| 5,288,611 A | | 2/1994 | Kohne et al. |
| 5,374,524 A | | 12/1994 | Miller et al. |
| 5,424,413 A | | 6/1995 | Hogan et al. |
| 5,437,977 A | | 8/1995 | Segev |
| 5,474,895 A | | 12/1995 | Ishii et al. |
| 5,484,699 A | | 1/1996 | Bouma et al. |
| 5,545,806 A | | 8/1996 | Lonberg et al. |
| 5,545,807 A | | 8/1996 | Surani et al. |
| 5,556,748 A | | 9/1996 | Douglas |
| 5,580,970 A | * | 12/1996 | Hendricks et al. ........ 536/24.32 |
| 5,614,362 A | | 3/1997 | Urdea et al. |
| 5,623,049 A | | 4/1997 | Lobberding et al. |
| 5,627,030 A | | 5/1997 | Pandian et al. |
| 5,629,153 A | | 5/1997 | Urdea |
| 5,629,156 A | | 5/1997 | Shah et al. |
| 5,635,352 A | | 6/1997 | Urdea et al. |
| 5,641,630 A | | 6/1997 | Snitman |
| 5,656,731 A | | 8/1997 | Urdea |
| 5,681,697 A | | 10/1997 | Urdea et al. |
| 5,681,897 A | | 10/1997 | Silvis et al. |
| 5,695,926 A | | 12/1997 | Cros et al. |
| 5,702,893 A | | 12/1997 | Urdea et al. |
| 5,728,531 A | | 3/1998 | Yamada et al. |
| 5,731,153 A | | 3/1998 | Lucas et al. |
| 5,736,316 A | | 4/1998 | Irvine et al. |
| 5,747,244 A | | 5/1998 | Sheridan et al. |
| 5,747,248 A | | 5/1998 | Collins |
| 5,750,338 A | | 5/1998 | Collins et al. |
| 5,759,773 A | | 6/1998 | Tyagi et al. |
| 5,786,183 A | | 7/1998 | Ryder et al. |
| 5,792,606 A | | 8/1998 | Deger et al. |
| 5,800,994 A | | 9/1998 | Martinelli et al. |
| 5,814,492 A | | 9/1998 | Carrino et al. |
| 5,821,339 A | | 10/1998 | Schaffer et al. |
| 5,827,661 A | | 10/1998 | Blais |
| 5,853,993 A | | 12/1998 | Dellinger et al. |
| 5,888,724 A | | 3/1999 | Silverstein et al. |
| 5,981,179 A | | 11/1999 | Lorincz et al. |
| 5,994,079 A | | 11/1999 | De La Rosa et al. |
| 6,010,895 A | | 1/2000 | Deacon et al. |
| 6,027,897 A | | 2/2000 | Lorincz et al. |

(Continued)

FOREIGN PATENT DOCUMENTS

| | | |
|---|---|---|
| CN | 1690223 A | 11/2005 |
| CN | 10117701 A | 5/2008 |

(Continued)

OTHER PUBLICATIONS

International Search Report Based on Application No. PCT/US2012/020684 dated Oct. 25, 2012.

(Continued)

*Primary Examiner* — Cynthia B Wilder
(74) *Attorney, Agent, or Firm* — McBee Moore Woodward & Vanik IP, LLC; Susan McBee

(57) ABSTRACT

Provided are nucleic acids capable of hybridizing to HPV 16 and/or HPV 18 nucleic acids, in particular, mRNA encoding E2 and E6-7 gene products. Such nucleic acids are useful in methods of isolating RNA from a biological sample, methods and means for determining the presence of particular RNA splice-form variants in a biological sample, methods and means for determining the relative ratio of RNA ratios in a biological sample, methods and means for predicting the progression of precancerous cervical lesions, and methods and means for detecting disruption of genes or gene expression.

33 Claims, 14 Drawing Sheets

(56) References Cited

U.S. PATENT DOCUMENTS

| | | | |
|---|---|---|---|
| 6,043,038 | A | 3/2000 | Sivaraja et al. |
| 6,057,099 | A | 5/2000 | Nathan et al. |
| 6,083,925 | A | 7/2000 | Li et al. |
| 6,110,676 | A | 8/2000 | Coull et al. |
| 6,110,682 | A | 8/2000 | Dellinger et al. |
| 6,110,687 | A | 8/2000 | Nilsen |
| 6,207,385 | B1 | 3/2001 | Stanley |
| 6,221,581 | B1 | 4/2001 | Engelhardt et al. |
| 6,225,053 | B1 | 5/2001 | Garcia et al. |
| 6,228,578 | B1 | 5/2001 | Impraim et al. |
| 6,228,580 | B1 | 5/2001 | Blumenfeld et al. |
| 6,232,462 | B1 | 5/2001 | Collins et al. |
| 6,268,128 | B1 | 7/2001 | Collins et al. |
| 6,277,579 | B1 | 8/2001 | Lazar et al. |
| 6,280,954 | B1 | 8/2001 | Ulfendahl |
| 6,326,136 | B1 | 12/2001 | Lazar et al. |
| 6,355,424 | B1 | 3/2002 | Lorincz et al. |
| 6,436,662 | B1 | 8/2002 | Mielzynska et al. |
| 6,521,190 | B1 | 2/2003 | Edens et al. |
| 6,544,732 | B1 | 4/2003 | Chee et al. |
| 6,583,278 | B1 | 6/2003 | Carter |
| 6,686,151 | B1 | 2/2004 | Lazar et al. |
| 6,828,098 | B2 | 12/2004 | Langmore et al. |
| 6,890,729 | B2 | 5/2005 | Mielzynska et al. |
| 6,969,585 | B2 | 11/2005 | Lorincz et al. |
| 6,977,148 | B2 | 12/2005 | Dean et al. |
| 7,001,776 | B2 | 2/2006 | Botacini Das Dores et al. |
| 7,138,505 | B1 | 11/2006 | Kuo et al. |
| 7,371,518 | B2 | 5/2008 | Lorincz et al. |
| 7,439,016 | B1 * | 10/2008 | Anthony .............. C12Q 1/6834 435/6.1 |
| 7,601,497 | B2 | 10/2009 | Nazarenko et al. |
| 7,645,571 | B2 | 1/2010 | Anthony et al. |
| 7,812,144 | B2 | 10/2010 | Karlsen |
| 7,829,691 | B2 | 11/2010 | Anthony et al. |
| 8,012,944 | B2 | 9/2011 | Lacasse et al. |
| 2001/0055766 | A1 | 12/2001 | Aristarkhov et al. |
| 2002/0012936 | A1 | 1/2002 | Lorincz et al. |
| 2003/0096232 | A1 | 5/2003 | Kris et al. |
| 2003/0108897 | A1 | 6/2003 | Drmanac |
| 2003/0175765 | A1 | 9/2003 | Kessler et al. |
| 2004/0180362 | A1 | 9/2004 | Lazar et al. |
| 2004/0214302 | A1 | 10/2004 | Anthony et al. |
| 2005/0009063 | A1 | 1/2005 | Xia et al. |
| 2005/0026976 | A1 | 2/2005 | Curtin et al. |
| 2005/0032038 | A1 | 2/2005 | Fisher et al. |
| 2005/0032105 | A1 | 2/2005 | Bair et al. |
| 2005/0119217 | A1 | 6/2005 | Lacasse et al. |
| 2005/0147996 | A1 | 7/2005 | Sorge |
| 2006/0051809 | A1 | 3/2006 | Nazarenko et al. |
| 2006/0160188 | A1 | 7/2006 | Kurnit et al. |
| 2006/0240449 | A1 | 10/2006 | McGlennen et al. |
| 2006/0275784 | A1 | 12/2006 | Light |
| 2007/0109898 | A1 | 5/2007 | Kasai |
| 2007/0154884 | A1 | 7/2007 | Lorincz |
| 2007/0292899 | A1 | 12/2007 | Lovell et al. |
| 2008/0200344 | A1 | 8/2008 | Cheng |
| 2008/0247914 | A1 | 10/2008 | Edens et al. |
| 2009/0032445 | A1 | 2/2009 | Doak et al. |
| 2009/0263819 | A1 | 10/2009 | Muraca |
| 2009/0298187 | A1 | 12/2009 | Nazarenko et al. |
| 2010/0081124 | A1 | 4/2010 | Abravaya et al. |
| 2010/0105060 | A1 | 4/2010 | Eder et al. |
| 2010/0126286 | A1 | 5/2010 | Self et al. |
| 2010/0129789 | A1 | 5/2010 | Self et al. |
| 2010/0159463 | A1 | 6/2010 | Eder et al. |
| 2010/0311039 | A1 | 12/2010 | Lowe et al. |
| 2011/0009277 | A1 | 1/2011 | Devos et al. |
| 2014/0087449 | A1 | 3/2014 | Ballhause et al. |

FOREIGN PATENT DOCUMENTS

| | | | | |
|---|---|---|---|---|
| EP | 0079139 | | | 5/1983 |
| EP | 0 163 220 | | | 12/1985 |
| EP | 0 167 366 | | | 1/1986 |
| EP | 0184017 | | | 6/1986 |
| EP | 0 281 927 | | | 9/1988 |
| EP | 0 288 737 | | | 11/1988 |
| EP | 0333465 | | | 9/1989 |
| EP | 0 336 454 | | | 11/1992 |
| EP | 0 144 914 | | | 6/1995 |
| EP | 0 415 978 | | | 3/1996 |
| EP | 0 703 296 | | | 3/1996 |
| EP | 1119676 | | * | 1/2001 |
| EP | 1 806 410 | A2 | | 7/2007 |
| EP | 2 184 368 | A1 | | 5/2010 |
| JP | H07505759 | A | | 6/1995 |
| JP | T H-07-505759 | A | | 6/1995 |
| JP | H08505770 | A | | 6/1996 |
| JP | 200400508019 | A | | 3/2004 |
| JP | T-2007-509861 | A | | 4/2007 |
| JP | 2009 106220 | | | 5/2009 |
| WO | 8607387 | | | 12/1986 |
| WO | 88/03957 | | | 6/1988 |
| WO | 91/08312 | | | 6/1991 |
| WO | 93/10263 | | | 5/1993 |
| WO | 93/10263 | A1 | | 5/1993 |
| WO | 84/02721 | | | 7/1994 |
| WO | 94/16108 | | | 7/1994 |
| WO | 94/16108 | A1 | | 7/1994 |
| WO | 95/16055 | | | 6/1995 |
| WO | 95/17430 | | | 6/1995 |
| WO | 96/40992 | | | 5/1996 |
| WO | 96/40992 | | | 12/1996 |
| WO | 97/05277 | | | 2/1997 |
| WO | 97/10364 | | | 3/1997 |
| WO | 97/31256 | | | 8/1997 |
| WO | 98/18488 | | | 5/1998 |
| WO | 98/22620 | | | 5/1998 |
| WO | 98/59044 | | | 12/1998 |
| WO | 99/02488 | | | 1/1999 |
| WO | 99/29909 | | | 6/1999 |
| WO | 99/32654 | | | 7/1999 |
| WO | 99/36571 | | | 7/1999 |
| WO | 99/39001 | | | 8/1999 |
| WO | 99/40224 | | | 8/1999 |
| WO | 99/49224 | | | 9/1999 |
| WO | 99/50459 | | | 10/1999 |
| WO | 00/60116 | | | 10/2000 |
| WO | 0075336 | A2 | | 12/2000 |
| WO | 01/36681 | | | 5/2001 |
| WO | 0196608 | | | 12/2001 |
| WO | 02066993 | A1 | | 8/2002 |
| WO | 2004/087950 | | | 10/2004 |
| WO | 2005042030 | A1 | | 5/2005 |
| WO | 2005/080602 | | | 9/2005 |
| WO | 2005/088311 | A1 | | 9/2005 |
| WO | 2006039563 | A2 | | 4/2006 |
| WO | 2006/124771 | A2 | | 11/2006 |
| WO | 2007/056723 | | | 5/2007 |
| WO | 2007/130519 | A2 | | 11/2007 |
| WO | 2007134252 | A1 | | 11/2007 |
| WO | 2008/036061 | | | 3/2008 |
| WO | 2008/139938 | A1 | | 11/2008 |
| WO | 2008149237 | A2 | | 12/2008 |
| WO | 2009/057993 | A1 | | 5/2009 |
| WO | 2009/123996 | | | 10/2009 |
| WO | 2010/004251 | A1 | | 1/2010 |
| WO | 2010/028382 | | | 3/2010 |
| WO | 2010052317 | A1 | | 5/2010 |
| WO | 2010/127228 | A1 | | 11/2010 |

OTHER PUBLICATIONS

Clad et al.; "Performance of the Aptima High-Risk Human Papillomavirus MRNA Assay in a Referral Population in Comparison With Hybrid Capture 2 and Cytology"; Journal of Clinical Microbiology; Mar. 2011; LNKD- Pubmed:21191046; vol. 49; No. 3; Dec. 29, 2010; pp. 1071-1076; Abstract.

Li et al; Detection of Human Papillomavirus Genotypes With Liquid Bead Microarray in Cervical Lesions of Northern Chinese

(56) References Cited

OTHER PUBLICATIONS

Patients; Cancer Genetics and Cytogenetics, Elsevier Science Publishing, New York, NY, US; vol. 182; No. 1; Mar. 6, 2008; pp. 12-17; Abstract.
Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.
Han et al.; "Simultaneous Amplification and Identification of 25 Human Papillomavirus Types With Templex Technology"; Journal of Clinical Microbiology Nov. 2011 US LNKD- DOI:10.1128/JCM.01762-06; vol. 44; No. 11; Nov. 2006; pp. 4157-4162; Abstract.
Database EMBL [Online]; Jul. 19, 2007; "Sequence 25 From Patent EP1806410"; XP002675256; Retrieved From EBI Accession No. EMBL:CS642417; Database Accession No. CS642417; The Whole Document.
Database EMBL [Online]; Dec. 14, 2010; "Sequence 26 From U.S. Pat. No. 7812144"; XP00267527; Retrieved From EBI Accession No. EMBL:GX640151; Database Accession No. GX640151; The Whole Document.
Database Geneseq [Online]; Jan. 22, 2009; "HPV-16 E7/E6 Gene Target Sequence, Bases 752-774"; XP002675258, Retrieved From EBI Accesssion No. GSN:ATS82292; Database Accession No. ATS82292; The Whole Document.
Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; The Whole Document.
Database Geneseq [Online]; Apr. 1, 2010; "HPV16 E7 Gene Forward RT-PCR Primer Seq ID 49"; XP002675260; Retrieved From EBI Accession No. GSN:AXU96631; Database Accession No. AXU96631; The Whole Document.
Database Geneseq [Online]; Apr. 21, 2005; "E7 Coding Region (1-87) Amplifying Sense PCR Primer, Seq ID No. 37"; XP002675261; Retrieved From EBI Accession No. GSN:ADX15568; Database Accession No. ADX15568; Sequence.
Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.
International Search Report and Written Opinion based on PCT/US2001/037012 dated Apr. 17, 2012.
Lowe et al.; "A Hybrid-Capture Assay to Detect HPV MRNA Ratios in Cervical Specimens"; Journal of Virological Methods; vol. 179; No. 1; Jan. 2012; pp. 142-147.
International Search Report Based on Application No. PCT/US2012/026380 dated Oct. 15, 2012.
International Preliminary Report on Patentability dated Aug. 27, 2013, issued in Application No. PCT/US2012/026380.
Lowe et al.; U.S. Appl. No. 12/771,043, filed Apr. 30, 2010.
Lowe et al.; Office Action dated May 7, 2012 (17 pages), U.S. Appl. No. 12/771,043, filed Apr. 30, 2010.
European Office Action dated Jul. 4, 2014, issued in Application No. 09 752 940.8-1403.
Japanese Office Action dated Jun. 30, 2014, issued in Application No. 2011-548258.
Chinese Office Action dated May 4, 2014, issued in Application No. 200980143682.9, English translation.
Luo et al., "Adiponectin stimulates human osteoblasts proliferation and differentiation via the MAPK signaling pathway," Experimental Cell Research, Academic Press, US, 309: 1, (Sep. 10, 2005) 99-109, XP005037411.
Ouitas N. et al., "A Novel ex vivo skin model for the assessment of the potential transcutaneous anti-inflammatory effect of topically applied Harpagophytum procumbens extract," International Journal of Pharmaceutics, Elsevier BV, NL, 376: 1-2, (Jul. 6, 2009), 63-68, XP026185227.
Scholz et al., "Analysis of human immunodeficieny virus matrix domain replacements," Virology, Elsevier, Amsterdam, NL. 371: 2, (Nov. 8, 2007) 322-335, XP022439785.
Xie H. et al., "Apelin in and its receptor are expressed in human obsteoblasts," Regulatory Peptides, Elsevier Science B.V., NL, 134: 2-3, (May 15, 2006), 118-125, XP27895144.
Zhang W. et al., "Bone-Targeted Overespression of Bcl-2 Increases Osteoblast Adhesion and Differentiation and Inhibits of Mineralization In Vitro," Calcified Tissue International, Springer-Verlag, NE, 80: 2, (Feb. 2, 2007), 111-122.
European Office Action dated Jul. 14, 2014, issued in Application No. 10 755 291.1-1406.
Chinese First Action dated Aug. 2, 2013, issued in Application No. 201180016276.3 and English translation thereof.
Molijn A. et al., "Molecular diagnosis of human papillomavirus (HPV) infections," Journal of Clinical Virology, 2005, vol. 32S at pp. S43-S51.
Chinese Office Action (Second) issued in Application No. 200980143682.9, dated Aug. 5, 2013, and English translation thereof.
Chinese First Action dated Apr. 15, 2013, issued in Application No. 201080018737.6.
Chinese First Action dated Apr. 26, 2013, issued in Application No. 201180012414.0 and English translation thereof.
Instructions RIPA Buffer (No. 89900 89901) [online] Thermo Scientific, 2006, [<Retrieved from the Internet: http://www.piercenet.com/instructions/2161782.pdf>].
Japanese Notice of Reasons for Rejection dated Nov. 27, 2013, issued in Application No. 2011-533405 and English translation thereof.
Rychlik et al., A computer program for choosing optimal oligonucleotides for filter hybridization, sequence and in vitro amplification of DNA. Nucleic Acids Research, 17, 8543-8551, 1989.
European Office Action dated Oct. 18, 2013, issued in Application No. 11 726 003.4-1403.
Australian Patent Examination Report No. 1, dated Oct. 24, 2013, issued for Application No. 2009238247.
Huang SL et al., Comparison between the Hybrid Capture II Test and an SPF1/GP6+ PCR-based assay for detection of human papillomavirus DNA in cervical swab samples. J. Clin Microbiol. 2006, 44(5):1733-9.
Mittendorf T, et al., "HPV-DNA-Diagnostik zur Zervixkarzinomfrüherkennung; Deutsche Agentur für HTA des Deutschen Instituts für Medizinische Dokumentation und Information," 1. Auflage 2007.
Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.
Davey DD, et al., "Introduction and Commentary, Strategic Science Symposium, Human Papillomavirus Testing—Are you ready for a new era in cervical cancer screening?," Arch Pathol Lab Med, 127: 927-929, Aug. 2003.
Malloy C, et al., "HPV DNA Testing: Technical and Programmatic issues for Cervical Cancer Prevention in Low-Resource Settings," Path, Dec. 2000.
Stacey SN, et al., "Translation of the Human Papillomavirus Type 16 E7 Oncoprotein from Bicistronic mRNA is independent of Splicing Events within the E6 Open Reading Frame," Journal of Virology, 69(11):7023-7031. Nov. 1995.
Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).
Bohm S. et al., "The Predominant mRNA Class in HPV16-Infected Genital Neoplasias does not Encode the E6 or the E7 Protein," Int. J. Cancer: 55, 791-796 (1993).
Middleton, K, et al., "Organization of Human Pepillomavirus Productive Cycle during Neoplastic Progression Provides a Basis for Selection of Diagnostic markers," Journal of Virology, Oct. 2003, pp. 10186-10201.
Kleter et al., "Development and clinical evaluation of a highly sensitive PCT-reverse hybridization line probe assay for detection

(56) References Cited

OTHER PUBLICATIONS and identification of anogenital human papillomafirus," In: Journal of clinical Micorbiology, Aug. 1999, vol. 37(8), pp. 2508-2517, see the whole document.
GenBank Accession No. AB027021, "Human papillomavirus type 82 DNA, complete genome.", Jun. 22, 2000. See http://www.ncbi.nlm.nih.gov/nuccore/6970427.
GenBank Accession No. X67161, "Human papillomavirus type L1 gene for major capsid protein.", Apr. 18, 2005. See http://www.ncbi.nlm.nih.gov/nuccore/1197494.
Park: JS, et al., "Physical Status and Expression of HPV Genes in Cervical Cancers," Gynec. Oncol. 95 (1997), pp. 121-129.
GenBank Accession No. U31794, "Human papillomavirus type 66. complete genorne.", Oct. 18, 1995. See http://www.ncbi.nlm.nih.gov/nuccore/1020290.
Letter dated Jan. 6, 2010 to EPO re EP 1 038 022 (46 pages).
Letter to EPO dated Mar. 2, 209 re EP 1 038 055 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).
Partial International Search Report for PCT/US2009/062041, dated Jan. 5, 2010.
Partial International Search Report for PCT/US2009/062041, dated Apr. 8, 2010.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly (dT) and Poly (I) Poly dC) as Immunogens for the Induction of Antibodies to RNA-DNA Hybrids," Molecular Immunology, vol. 19, No. 3, pp. 413-420, 1982.
Ishikawa et al., "Enzyme-Labeling of Antibodies and Their Fragments for Enzyme Immunoassay and Immunohistochemical Staining," Journal of Immunoassay and Immunochemistry, 4: 3, 209-327.
Means et al., "Chemical Modifications of Proteins: History and Applications," Bioconjugate Chem. 1990, 1, 2-12.
Jakobovits et al., "Analysis of homozygous mutant chimeric mice: Deletion of the immunoglobulin heavy-chain joining region blocks B-cell development and antibody production," Proc. Natl. Acad. Sci. USA. vol. 90, pp. 2551-2555, Mar. 1993 Genetics.
Jakobovits et al., "Germ-line transmission and expression of a human-derived yeast artificial chromosome," pp. 255-258, Nature, vol. 362, Mar. 18, 1993.
International Search Report for PCT/US2009/041033, dated Dec. 22, 2009.
Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al., "Classification of papillomarviruses," In: Virology, Jun. 2004, vol. 324(1). pp. 17-27—see table 3.
GenBank Accession No. K02718, "Human papillomavirus type 16 (HPV16), complete genome.", Mar. 18, 1994. See http://www.ncbi.nlm.nihgov/nuccore/333031.
GenBank Accession No. X74479, "human papillomavirus type 45 genomic DNA.", Apr. 18, 2005. See http://www.ncbi.nlm.nih.gov/nuccore/397022 .
GenBank Accession No. X05015. "Human papillomavirus type 18 E6, E7, E1, E2, E4, E5, L1 & L2 genes.", Apr. 18, 2005. See http://www.ncbi.nlm.nih.gov/nuccore 60975.
GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002. See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999. See http://www.ncbi.nlm.nih.gov/nuccore/333087.
GenBank Accession No. X74481, "Human papillomavirus type 52 genomic DNA.", Apr. 18, 2005. See http://www.ncbi.nlm.nih.gov/nuccore/397038.
GenBank Accession No. X74483, "Human papillomavirus type 56 genomic DNA.", Apr. 18, 2005. See http://www.ncbi.nlm.nih.gov/nuccore/397053.
GenBank Accession No. D90400, "Human papillomavirus type 58, complete genome.", Dec. 7, 2007. See http://www.ncbi.nlm.nih.gov/nuccore/222386.
GenBank Accession No. X77858, "Human papillomavirus type 59, complete viral genome,", Apr. 18, 2005. See http://www.ncbi.nlm.nih.gov/nuccore/557236.
Zientara et al., 1998 "Use of reverse transcriptase-polymerase chain reaction (RT-PCR) and dot-blot hybridization for the detection and identification of African horse sickness virus nucleic acids" Arch Virol 14:317-327.
Mansy et al., 1999 "A PCR Based DNA Hybridisation Capture System for the Detection of Human Cytomegalovirus. A Comparative Study with Other Identification Methods" Journal of Virological Methods 80:113-122.
Poulsen et al., 1999 "Detection of Clinical Vancomycin-Resistant Enterococci in Denmark by Multiplex PCR and Sandwich Hybridization" APMIS 107:404-12.
Sjoroos et al., 1998 "Time-Resolved Fluorometry Based Sandwich Hybridisation Assay for HLA-DQA1 Typing" Disease Markers 14:9-19.
Edman et al., 2000 "Pathogen Analysis and Genetic Predisposition Testing Using Microelectronic Arrays and Isothermal Amplification" Journal of Investigative Medicine, 48:93-101.
Monteiro et al., 1997 Evaluation of Performances of Three DNA Enzyme Immunoassays for Detection of Helicobacter pylori PCR Products for Biopsy Specimens Journal of Clinical Microbiology, 35:2931-2936.
Chiu et al., 1998 "Sandwich-type Deoxyribonucleic Acid Hybridization Assays Based on Enzyme Amplified Time-Resolved Fluorometry" Analyst , 123:1315-1319.
White et al., 1999 "Signal Amplification System for DNA Hybridization Assays Based on in vitro Expression of a DNA Label Encoding Apoaequorin" Nucleic Acids Research 27:i-viii.
Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.
Zammatteo et al., 1997 "Comparison between Microwell and Bead Supports for the Detection of Human Cytomegalovirus Amplicons by Sandwich Hybridization" Analytical Biochemistry 253:180-189.
Fisher et al., 1997 "A System for the Quantitation of DNA Using a Microtiter Plate-Based Hybridization and Enzyme Amplification Technology" Analytical Biochemistry 251:280-287.
Wicks et al., 1998 "A Sandwich Hybridization Assay Employing Enzyme Amplification for Determination of Specific Ribosomal RNA from Unpurified Cell Lysates" Analytical Biochemistry 259:258-264.
Bruckner-Lea et al., 2000 "Rotating Rod Renewable Microcolumns for Automated, Solid-Phase DNA Hybridization Studies" Anal. Chem. 72:4135-4141.
Allen et al., 1998 "High Resolution Genetic Typing of the Class II HLA-DRB 1 Locus Using Group-Specific Amplification and SSO-Hybridisation in Microplates" Hereditas 129:161-167.

(56) References Cited

OTHER PUBLICATIONS

Chomvarin et al., 2000 "Development of EIA for Detection of Chlamydia Trachomatis in Genital Specimens" The Southeast Asian Journal of Tropical Medicine and Public Health, 31:96-103.
Alexandre et al., 1998 "Quantitative Determination of CMV DNA Using a Combination of Competitive PCR Amplification and Sandwich Hybridization" BioTechniques, 25: 676-683.
Casademont et al., 2000 "Rapid Detection of Campylobacter fetus by Polymerase Chain Reaction Combined With Non-Radioactive Hybridization Using an Oligonucleotide Covalently Bound to Microwells" Molecular and Cellular Probes 14:233-240.
Hara et al., "Small Sample Whole-Genome Amplification," Optics East 2005, UCRL-PROC-216415, Lawrence Livermore National Laboratory, Oct. 21, 2005.
Brigotti, et al., "A rapid and sensitive method to measure the enzymatic activity of ribosome-inactivating proteins," Nucleic Acids Res.. vol. 26, No. 18, pp. 4306-4307, 1998.
PCT/US2009/062061, International Searching Authority, dated Oct. 26, 2009 (6 pages).
PCT/US2009/062041, International Searching Authority, dated Oct. 26, 2009 (5 pages).
Bart "General Principles of Immunoprecipitation," Jul. 31, 2008 (XP002560372).
Bhan et al., "2',5'-Linked oligo-3' deoxyribonucleoside phosphorothioate chimeras: thermal stability and antisense inhibition of gene expression," Nucleic Acids Research, 1997, vol. 25, No. 16, pp. 3310-3317 (XP-002560367).
Genetech Diagnostics Pvt. Ltd., "Digene HBV Test Hybrid Capture II," Jun. 6, 2008 (XP-002560368).
Hantz et al., "Evaluation of accuracy of three assays for human papillomavirus detection and typing: Hybrid Capture 2, HPV Consensus kit and Amplicor HPV," Pathologie Biologie, Feb. 2008, vol. 56, No. 1, pp. 29-35 (XP002560369).
Sandri et al., "Comparison of the Digene HC2 Assay and Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146 (XP002560370).
Boston Bioproducts Inc., "Protein Extraction buffers," Sep. 2, 2007 (XP002560371).
Broker et al., "A Molecular Portrait of Human Papillomavirus Carcinogenesis", Cancer Cells, vol. 7, pp. 197-208, 1989 (Roche EU Opposition).
Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).
Karlsen et al., "Use of Multiple PCR Primer Sets for Optimal Detection of Human Papillomavirus", Journal of Clinical Microbiology, pp. 2095-2100, Sep. 1996 (Roche EU Opposition).
Park et al., "Physical Status and Expression of HPV Genes in Cervical Cancers", Gynecologic Oncology, vol. 65, pp. 121-129, 1997 (Roche EU Opposition).
Stoler et al., "Human Papillomavirus Type 16 and 18 Gene Expression in Cervical Neoplasias", Human Pathology, vol. 23, No. 2, pp. 117-128, Feb. 1992 (Roche EU Opposition).
De Villiers et al., "Classification of Papillomaviruses", Virology, vol. 324, pp. 17-27, 2004.
Howley et al., "A Rapid Method for Detecting and Mapping Homology between Heterologous DNAs", Journal of Biological Chemisny, vol. 254, No. 11, pp. 4879-4883, Jun. 10, 1979.
Law et al., "Conserved Polynucleotide Sequences Among the Genomics of Papillomaviruses", Journal of Virology, vol. 32, No. 1, pp. 199-207, Oct. 1979.
Heilman et al., "Cloning of Human Papilloma Virus Genomic DNAs and Analysis of Homologous Polynucleotide Sequences", Journal of Virology, vol. 36, No. 2, pp. 395-407, Nov. 1980.
Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.
Lorincz, A.T., "Molecular Methods for the Detection of Human Papillomavirus Infection", Obstetrics and Gynecology Clinics of North America, vol. 23. No. 3, pp. 707-730, Sep. 1996.
Eder et al., "The Next-Generation Hybrid Capture(R) High-Risk HPV DNA Assay on a Fully Automated Platform", Journal of Clinical Virology, vol. 46, No. 1. Jul. 2009, pp. S85-S92.
Stoler et al., "In Situ Hybridization Detection of Human Papillomavirus DNAs and Messenger RNAs in Genital Condylomas and a Cervical Carcinoma", Human Pathology, vol. 17, No. 12, Dec. 1, 1986, pp. 1250-1258.
Lornicz, "Hybrid Capture Method for Detection of Human Papillomavirus DNA in Clinical Specimens: A Tool for Clinical Management of Equivocal Pap Smears and for Population Screening", Journal of Obstetrics and Gynaecology Research, vol. 22, No. 6, Dec. 1, 1996, pp. 629-636.
Blair et al. "Herpes Simplex Virus Viron Stimulatory Protein mRNA Leader Contains Sequence Elements Which Increase Both Virus-Induced Transcription and tnRNA Stability." Journal of Virology, vol. 61, No. 8, pp. 2499-2508, Aug. 1987.
Larder et al. "Related Functional Domains in Virus DNA Polymerases,"The EMBO Journal. vol. 6, No. 1, pp. 160-175, 1987.
Chandler et al., Detection of Dengue-2 Viral RNA by Reversible Target Capture Flybridization., J. Clin. Microbiol., vol. 31 (10), pp. 2641-2647, 1993.
Mazzulli et al, 1999, Multicenter Comparison of the Digene Hybrid Capture CMV DNA Assay (version 2.0) the pp65 Antignenemia Assay, and Cell Culture for Detection of Cytomegalovirus Viremia, J Clin. Microbiol., vol. 37, No. 4, pp. 958-963, 1999.
Murakami et al., Fidorescent-Labeled Oligonucleotide Probes: Detection of Hybrid Formation in Solution by Fluorscence Polarization Spectroscopy, Nucleic Acids Res., vol. 19 (15), pp. 4097-4102, 1991.
Dunn and Hassell: "A Novel Method to Map Transcripts: Evidence for Homology between an Adenovirus niRNA and Discrete Multiple Regions of the Viral Genome" Cell, 12:23-36, Sep. 1977.
Coutlee et al., "Nonisotopic Detection of RNA in an Enzyme Imunoassay using a Monoclonal Antibody Against DNA-RNA Hybrids" Analytical Biochemistry 181:153-162, 1989.
Chen et al., "DNA Optical Sensor: A Rapid Method for the Detection of DNA Hybridization" Biosensors & Bioelectronics 13:451-458, 1998.
Chevrier et al., "Isolation of a Specific DNA fragment and Development of a PCR Based Method for the Detection of Mycobacterium genavense" FEMS Immunology and Medical Microbiology 23:243-452, 1999.
Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acid Research, 1126:5581-5588, 1998.
Gelmetti et al., "Detection of Rabbit Haemorrhagic Disease Virus (RHDV) by In Situ Hybridisation With a Digoxigenin Labelled RNA Probe" Journal of Virological Methods 72:219-226, 1998.
Radtkey et al., "Rapid, High Fidelity Analysis of Simple Sequence Repeats on an Electronically Active DNA Microchip" Nucleic Acids Research 28:i-vi, 2000.
Namimatsu et al., "Detection of Salmonella by Using the Colorimetric DNA/rRNA Sandwich Hybridization in Microtiter Wells" J. Vet. Med. Sci. 62:615-619, 2000.
Lazar et al., 1999 "Hybrid Capture ®: a Sensitive Signal Amplification-based Chemiluminescent Test for the Detection and Quantitation of Human Viral and Bacterial Pathogens".1. Clin. Ligand Assay 22:139-151.
Newman et al., 1989 "Solution Hybridization and Enzyme Immunoassay for Biolinylated DNA:RNA Hybrids to Detect Enteroviral RNA in Cell Culture" MoL Cell Probes 3:375-382.
Lamoureux et al., 1997 "Detection of Campylobacter jejuni in Food and Poultry Viscera Using Immunomagnetic Separation and Microtitre Hybridization" J. Appl. Microbiol. 83:641-651.

(56) References Cited

OTHER PUBLICATIONS

Coutlee et al., 1990 "Quantitative Detection of Messenger RNA by Solution Hybridization and Enzyme Immunoassay" Biol. Chem. 265:11601-11604.
Stollar, B.D. and A. Rashtchian, 1987 "Immunochemical Approaches to Gene Probe Assays" Anal. Biochem. 161:387-394.
Blais, B.W., 1994 "Transcriptional Enhancement of the Listeria Monocytogenes PCR and Simple Immunoenzymatic Assay of the Product Using Anti-RNA:DNA Antibodies" AppL Environ. Microbiol. 60:348-352.
Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.
Viscidi et al., 1989 "Monoclonal Antibody Solution Hybridization Assay for Detection of Human Immunodeficiency Virus Nucleic Acids" J. Clin. Microbiol. 27:120-125.
Boguslawski et al., 1986 "Characterization of Monoclonal Antibody to DNA:RNA and its Application to Immunodetection of Hybrids" J. Immunol. Methods 89:123-130.
Coutlee et al., 1989 "Immunodetection of DNA with Biotinylated RNA Probes: A Study of Reactivity of a Monoclonal Antibody to DNA-RNA Hybrids" Anal. Biochem. 181:96-105.
Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).
Coutlee et al., 1989 "Comparison of Colorimetric Fluorescent, and Enzymatic Amplification Substrate Systems in an Enzyme Immunoassay for Detection of DNA-RNA Hybrids" J. Clin. Microbiol. 27:1002-1007.
Dalrymple et al., DNA sequence of the herpes simplex virus type 1 gene whose product is responsible for transcriptional activation of immediate early promoters, Nucleic Acids Research, 1985, vol. 13, No. 21, pp. 7865-7879.
McLauchlan et al., DNA sequence homology between two co-linear loci on the HSV genome which have different transforming abilities, The EMBO Journal, 1983, vol. 2, No. 11, pp. 1953-1961.
Goldsborough et al., Nucleotide Sequence of Human Papillomavirus Type 31: A Cervical Neoplasia Associated Virus, Virology, 1989, vol. 171, pp. 306-311.
McGeoch et al., "DNA Sequence and Genetic Content of the HindIII 1 Region in the Short Unique Component of the Herpes Simplex Virus Type 2 Genome: Identification of the Gene Encoding Glycoprotein G, and Evolutionary Comparisons," J. Gen. Virol., 1987, vol. 68, pp. 19-38.
McGeoch et al., The Complete DNA Sequence of the Long Unique Region in the Genome of Herpes Simplex Virus Type I, 1 Gen Virol., 1988, vol. 69, pp. 1531-1574.
Yamada et al., Human Papillomavirus Type 16 Variant Lineages in United States Populations Characterized by Nucleotide Sequence Analysis of the E6, L2, and LI Coding Segments, J. Virol., Dec. 1995, vol. 69, No. 12, pp. 7743-7753.
Swain et al., Nucleotide Sequence of the Herpes Simplex Virus Type 2 Thymidine Kinase Gene,' Virol., Jun. 1983, vol. 48, No. 3, pp. 1045-1050.
Delius et al., Primer-Directed Sequencing of Human Papillomavirus Types, Current Topics in Microbiology and Immunology, 1994, vol. 185, pp. 13-31.
Blair et al., Herpes Simplex Virus Virion Stimulatory Protein mRNA Leader Contains Sequence Elements Which Increase Both Virus-Induced Transcription and mRNA Stability, J. Virol., Aug. 1987, vol. 62, No. 2, pp. 444-453.
Larder et al., Related functional domains in virus DNA polymerases, The EMBO J., 1987, vol. 6, No. 1, pp. 169-175.
McGeoch et al., Structures of Herpes Simplex Virus Type 1 Genes Required for Replication of Virus DNA, J. Virol., vol. 62, No. 2, pp. 444-453, 1989.
Supplementary European Search Report of PCT/US2006/060603, dated Jul. 7, 2010 (8 pages).
Lowe, et al., "A computer program for selection of oligonucleotide primers for polymerase chain reactions", Nucleic Acid Res., vol. 18, No. 7, pp. 1757-1761 (1990).
International Search Report and Written Opinion of PCT/US2010/022264 dated Jun. 7, 2010 (19 pages).
Cohenford et al., "C-195. Rapid Detection of Chlamydia trachomatis from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.
Gentech Diagnostics: "Chlamydia DNA Test Kit." (Jun. 6, 2008), XP002578832, Retrieved from the Internet: URL:http://www.gentechin.com/chlamydiatestkit.htm.
Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.
Darwin et al, "Comparison of Digene Hybrid Capture 2 and Conventional Culture for Detection of Chlamydia trachomatis and Neisseria gonorrhoeae in Cervical Specimens," Journal of Clinical Microbiology, (Feb. 2002), pp. 641-644, vol. 40, No. 2, XP002578833.
Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.
International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6.
Vernick et al., "The HPV DNA virus hybrid capture assay: What is it—and where do we go from here?" MLO Med. Lab. Obs., (Mar. 2003), pp. 8-10, 13, vol. 35. No. 3.
International Search Report and Written Opinion of PCT/US2010/048714, dated Dec. 10, 2010 (14 pages).
International Preliminary Report on Patentability and Written Opinion of PCT/US2009/041033, dated Oct. 19, 2010 (6 pages).
International Search Report and Written Opinion of PCT/US2010/047769, dated Nov. 9, 2010 (11 pages).
Pachowics, et al., "Sequence specific large volume sample prep solution utilizing Hybrid Capture Technology," 41st Annual Oak Ridge Conference; Baltimore, MD; Apr. 16, 2009; retrieved from the Internet; http://www.aacc.org/events/meeting_proceeding/2009/Documents/OakRidge09AllPosters.pdf.
Keegan et al., "Comparison of HPV detection technologies: Hybrid capture 2, PreTect HPV-Proofer and analysis of HPV DNA viral load in HPV16, and HPV18 and HPV33 E6/E7 mRNA positive specimens," Journal of Virological Methods, Jan. 1, 2009, pp. 61-66, vol. 155, No. 1, Elsevier BV, XP025799776.
Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.
Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.
Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott—Raven Publishers, XP008011933.
Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.
Tsai et al., "Association between Quantitative High-Risk Human Papillomavirus DNA Load and Cervical Intraepithelial Neoplasm

(56) References Cited

OTHER PUBLICATIONS

Risk," Cancer Epidemiology, Biomarkers & Prevention: American Association for Cancer Research, Nov. 2005, pp. 2544-2549, vol. 14, No. 11 pt 1, XP002603501.
Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.
Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.
Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12, No. 6; American Society for Investigative Pathology.
Partial European Search Report of EP10185824; dated Feb. 16, 2011 (8 pages).
Scott et al., "Detection of herpes simplex virus type 1 shedding in the oral cavity by polymerase chain reaction and enzyme-linked immunosorbent assay at the prodromal stage of recrudescent herpes laialis," Journal of Oral Pathology & Medicine; Aug. 1997; pp. 305-309; vol. 26, No. 7; XP009143938.
Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.
Poljak et al., "Human Papillomavirus Genotype Specificity of Hybrid Capture 2 Low-Risk Probe Cocktail", Journal of Clinical Microbiology, vol. 47, No. 8, Aug. 1, 2009, pp. 2611-2615.
International Search Report and Written Opinion for Application No. PCT/US2011/037684 dated Aug. 5, 2011.
Japanese Notice of Reasons for Rejection dated Aug. 28, 2014, issued in Application No. 2012-508768.
Coutlee et al., "Nonisotopic Detection of RNA in an Enzyme Immunoassay Using a Monoclonal Antibody against DNA-RNA Hybrids." Analytical Biochemistry 181, 153-162 (1989).
U.S. Appl. No. 12/904,459, filed Oct. 14, 2010.
U.S. Appl. No. 12/622,160, filed Nov. 19, 2009.
U.S. Appl. No. 12/576,425, filed Oct. 9, 2009.
U.S. Appl. No. 12/426,076, filed Apr. 17, 2009.
U.S. Appl. No. 12/605,605, filed Oct. 26, 2009.
U.S. Appl. No. 12/605,540, filed Oct. 26, 2009.
U.S. Appl. No. 12/695,071, filed Jan. 27, 2010.
U.S. Appl. No. 12/984,391, filed Jan. 4, 2011.
U.S. Appl. No. 12/986,540, filed Jan. 7, 2011.
U.S. Appl. No. 12/881,531, filed Sep. 14, 2010.
U.S. Appl. No. 13/016,004, filed Jan. 28, 2011.
U.S. Appl. No. 13/114,344, filed May 24, 2011.
U.S. Appl. No. 13/110,660, filed May 18, 2011.
U.S. Appl. No. 13/015,915, filed Jan. 28, 211.
U.S. Appl. No. 13/346,550, filed Jan. 9, 2012.
U.S. Appl. No. 12/695,001, filed Jan. 27, 2010.
U.S. Appl. No. 12/771,042, filed Apr. 30, 2010.

* cited by examiner

MATERIALS AND METHODS FOR DETECTION OF HPV NUCLEIC ACIDS

CROSS REFERENCE TO RELATED APPLICATIONS

This application claims priority to U.S. Provisional Application No. 61/446,306, filed on Feb. 24, 2011, and also U.S. Provisional Application No. 61/486,118, filed on May 13, 2011, which are both hereby incorporated by reference in their entirety.

BACKGROUND

1. Field

The present disclosure relates to methods, compositions, and kits for determining the presence of a nucleic acid in a sample, including nucleic acids derived from Human papillomavirus ("HPV").

2. Description of Related Art

Human papillomavirus (HPV) infection is the most important cause of cervical cancer, 13 types of which cause HPV-related cervical disease and cancer. Screening for oncogenic HPV DNA using molecular tests has been useful to diagnose HPV-related disease. However, current testing methods cannot precisely predict which infections may develop into cancer because most HPV infections are transient and regress and clear spontaneously. Therefore, additional biomarkers are being explored for use in reflex assays to confirm which infections will progress and require further treatment.

The progression of disease may be related to the expression of certain HPV genes. Detection of HPV mRNA may, therefore, be an additional biomarker for severe infections. Some HPV mRNA assays being developed for diagnostics detect a single type of transcript species, such as the E6 or E7 oncogenic sequences. These assays may not predict severe infections because the abundance of a single species may fluctuate due to the complex pattern of expression that occurs during the course of disease, or due to degradation of HPV from immune responses. In addition, an mRNA target may degrade after collection, or the number of infected cells in the collected specimen may be low, both of which may affect the assay result. As a solution, HPV assays designed to detect simultaneously two species of mRNAs in a ratio may be more predictive of disease than assays that detect a single mRNA species.

Additionally, HPV DNA is typically maintained as a productive infection in a circular, episomal state at 50-100 copies per cell. In this state, transcription of the HPV oncogenes E6 and E7 is tightly controlled by the E2 protein. E6 and E7 target p53 and pRb, respectively, and thus interfere with the normal cell cycle. Cells in which this transcriptional control is removed have a proliferative advantage over other cells due to their accelerated reentry into the cell cycle. Disruption or deletion of the E2 gene, as frequently occurs during integration of the virus into the host genome, removes the negative feedback on E6 and E7, activates telomerase, and derepresses hTERT expression, and thus clearly contributes to the progression of cell immortalization and ultimately, cancer progression.

The detection and characterization of specific nucleic acid sequences and sequence changes have been utilized to detect the presence of viral or bacterial nucleic acid sequences indicative of an infection, the presence of variants or alleles of mammalian genes associated with disease and cancers, and the identification of the source of nucleic acids found in forensic samples, as well as in paternity determinations. Characterization of the RNA species involved in normal biological processes may be important to understanding various little known biological processes.

The detection and characterization of RNA (e.g., messenger RNA, transfer RNA, ribosomal RNA, small nuclear RNA, and other RNAs) is an important tool in many fields including molecular biology, toxicology, and biochemistry. Messenger RNA (mRNA) is an essential functional constituent of a cell; during the process of gene expression, the functional single strand structure of mRNA is synthesized and serves as an intermediate template for the translation process in protein synthesis. The brief existence of an mRNA molecule begins with transcription of DNA into an RNA molecule, and ultimately ends in degradation. During its life, an mRNA molecule may also be processed, edited, and transported prior to translation. Splicing is the process by which pre-mRNA is modified to remove certain stretches of non-coding sequences called introns; the stretches that remain may include protein-coding sequences and are called exons. Sometimes pre-mRNA messages may be spliced in several different ways, allowing a single transcript to encode multiple proteins.

Detection of messenger RNA (mRNA) is critical in diagnostics because it can provide viral load and gene expression information that DNA detection cannot. These factors often give clues about the progression and prognosis of a disease. The current technologies for mRNA detection present a number of problems including complexity and potential for contamination.

The most common methods of mRNA detection include Northern blot, ribonuclease protection assay (RPA), and reverse-transcriptase polymerase chain reaction (RT-PCR). However, each of these techniques, while affording some advantages in sensitivity, requires time and material demands. In addition, some techniques require amplification of the target mRNA since total mRNA represents only about 1% of the total RNA and any particular mRNA is a significantly smaller percentage.

Currently, reverse transcriptase-polymerase chain reaction (RT-PCR) is widely used to characterize RNA transcripts. However the method has the following limitations: 1) only a limited number of the specific regions can be co-amplified; 2) mutations or alternative splicing can limit the ability of specific primers to detect the RNA; and 3) it is difficult to characterize the mRNA structure in a continuous mode method.

It therefore would be useful to have materials and methods capable of determining whether the a given nucleic acid is present or absent in a sample. Additionally, it would be useful to have materials and methods capable of determining whether a gene—including the HPV E2 gene—is disrupted, deleted, or otherwise is not being expressed in a host cell.

BRIEF SUMMARY

The present disclosure provides nucleic acids and methods useful in detecting specific nucleic acids in a sample and determining whether those nucleic acids are intact or disrupted.

In an aspect, an isolated nucleic acid is provided, having an overall length of not more than 200 nucleotides comprising, consisting essentially of, or consisting of at least one nucleotide sequence having at least 75-percent homology to a nucleotide sequence selected from the group consisting of SEQ ID NO: 1 to SEQ ID NO: 105 and SEQ ID NO: 111 to SEQ ID NO: 308, RNA equivalents thereof, and a complements thereof.

In an aspect, a method of detecting the presence of a target RNA is provided, the method comprising: a) providing at least one DNA capture probe, wherein the at least one DNA capture probe is bound to a support; b) hybridizing the target RNA to said at least one DNA capture probe, yielding a target RNA:DNA capture probe complex; c) isolating the target RNA:DNA capture probe complex; d) providing at least one DNA amplification probe, and hybridizing said at least one DNA amplification probe to said target RNA:DNA capture probe complex, yielding a target RNA:DNA capture/amplification probe complex; e) providing an anti-RNA:DNA hybrid antibody, and incubating said target RNA:DNA capture/amplification probe complex with said antibody, yielding a target RNA:DNA:antibody complex; f) detecting said antibody, wherein said detecting indicates the presence of said target RNA. In one aspect, antibody is conjugated to a detectable marker, and the step of detecting comprises detecting the marker. In one aspect, the detectable marker is selected from the group consisting of alkaline phosphatase and horseradish peroxidase. In one aspect, the step of detecting comprises providing a second antibody that binds to said anti-RNA:DNA hybrid antibody, wherein said second antibody is conjugated to a detectable marker, and wherein said detecting further comprises detecting the marker. In one aspect, the support comprises a magnetic bead. In one aspect, the magnetic bead is conjugated to at least one streptavidin molecule, and the at least one DNA capture probe is conjugated to a biotin molecule. In one aspect, at least one of the capture probes and/or amplification probes is a nucleic acid probe as set forth above.

In one aspect, the at least one DNA capture probe and the at least one DNA amplification probe are from about 15 to about 200 bases in length.

In one aspect, the target RNA is a splice variant, and the at least one DNA capture probe and the at least one DNA amplification probe are selected to detect the presence of said splice variant.

In one aspect, the at least one DNA capture probe and the at least one DNA amplification probe are complementary to RNA from HPV high risk types 16, 18, 31, 33, 35, 39, 45, 51, 52, 56, 58, 59, 68, 26, 66, 73, and 82.

In another aspect, a kit for the detection of a target RNA is provided, the kit comprising: a) at least one DNA capture probe, bound to a magnetic support; b) at least one DNA amplification probe; c) an anti-RNA:DNA hybrid antibody; and d) a detection reagent. In one aspect, said anti-RNA:DNA hybrid antibody is conjugated to a detectable marker, and said detection reagent comprises a substrate for said detectable marker. In one aspect, the kit further comprises a second antibody that binds to said anti-RNA:DNA hybrid antibody, wherein said second antibody is conjugated to a detectable marker, and wherein said detection reagent comprises a substrate for said detectable marker.

The present disclosure provides a method of providing target RNA for detection, the method comprising: incubating a biological sample containing the target RNA with carboxyl beads; isolating the beads; lysing the biological sample attached to the isolated beads; and isolating the beads from the lysed biological sample, wherein the resulting supernatant contains the target RNA for detection.

In another aspect, a method for nucleic acid detection is disclosed that does not rely on target amplification. Nucleic acids of interest are captured by specific nucleic oligonucleotides. Signal amplification is provided by adding DNA probes that cover the captured RNA target (or vice versa of the target is DNA) that is then detected using entities capable of binding specifically to DNA:RNA hybrids. This hybrid capture assay gives linear increases in signal as both quantity and length of transcripts increase. As a result, it can be used to measure deletions that existing technologies cannot. By assaying the extent of target nucleic acid disruption, as compared to total signal from a complete set of reference nucleic acids, one is able to whether, and the extent to which, the target is disrupted.

In an aspect, disruption of the target is determined by separating a sample into at least a first and second portion. The first portion of the sample is treated under conditions sufficient to generate two sets of DNA:RNA hybrids: one set comprising the target nucleic acid and one set comprising at least one reference nucleic acid. The second portion of the sample is then treated under conditions sufficient to generate the set of DNA:RNA hybrids comprising the reference nucleic acid, but not set comprising the target nucleic acid. The total amount of DNA:RNA hybrid in the first portion of the sample is then compared to the total amount of DNA:RNA hybrid in the second portion of the sample. If the target nucleic acid is missing, there should be the same amount of DNA:RNA hybrid in the first and second portions of the sample. Variations of the method also are presented for determining the extent of disruption, if any, by applying a plurality of probes specific for a substantial portion of the target nucleic acid and progressively removing the probes. The more probes that can be removed before a change in DNA:RNA hybrids is detected, the greater the extent to which the target nucleic acid is disrupted.

In another aspect, a method is provided to determine whether or not an E2 gene, cDNA, or mRNA is absent or disrupted. Such a method can be applied to, inter alia, determine whether the E2 gene is being expressed, whether the HPV genome is integrated into the host cell genome, assessing the progression of an HPV infection, and/or determining the risk of an HPV infection progressing to cancer.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

In FIG. 13, each set of 5 oligos are adjacent to one another and result in the RNA:DNA hybrid getting longer, and signal stronger, as successive sets are added.

DETAILED DESCRIPTION

Figure 1:
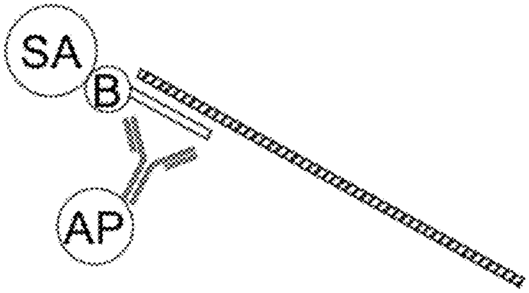
FIG. 1 is a schematic diagram of target RNA (crosshatched bar) captured by biotinylated DNA probes (white bar). "B" represents a biotin moiety; "SA" represents a streptavidin moiety; "AP" represents alkaline phosphatase conjugated to an antibody, but AP could be any other appropriate detectable moiety (e.g., horseradish peroxidase, etc.), and B and SA could be replaced by other linkage moieties.

Before the subject disclosure is further described, it is to be understood that the disclosure is not limited to the particular aspects of the disclosure described below, as variations of the particular aspects may be made and still fall within the scope of the appended claims. It is also to be understood that the terminology employed is for the purpose of describing particular aspects, and is not intended to be limiting.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

Isolated Nucleic Acids and Probes Capable of Hybridizing to HPV 16 and/or HPV 18

Nucleic acids consisting of not more than 200 nucleotides and being capable of hybridizing to HPV 16 or HPV 18 DNA or RNA are provided herein.

In an aspect, the nucleic acid comprises, consists essentially of, or consists of at least one nucleotide sequence having at least 75%, at least 80%, at least 85%, at least 90%, or at least 95% homology to a nucleotide sequence selected from the group consisting of SEQ ID NO: 1 to SEQ ID NO: 105 and SEQ ID NO: 111 to SEQ ID NO: 308, RNA equivalents thereof, and complements thereof. In a further aspect, the nucleic acid comprises, consists, or consists essentially of a nucleotide sequence selected from the group consisting of SEQ ID NO: 1 to SEQ ID NO: 105 and SEQ ID NO: 111 to SEQ ID NO: 308, RNA equivalents thereof, and complements thereof, In an aspect, the nucleic acid is capable of hybridizing under stringent conditions to a nucleic acid at least 75%, at least 80%, at least 85%, at least 90%, at least 95%, at least 96%, at least 97%, at least 98%, at least 98%, at least 99%, or 100% identical to an HPV16 or HPV18 genome or a nucleic acid derived from the same. The sequence of an exemplary HPV 16 genome is disclosed at GenBank NC_01526 (SEQ ID NO: 106). The sequence of an exemplary HPV 18 genome is disclosed at GenBank X05015 (SEQ ID NO: 107).

In another aspect, the nucleic acid is capable of hybridizing or binding to a nucleic acid at least 75%, at least 80%, at least 85%, at least 90%, at least 95%, at least 96%, at least 97%, at least 98%, at least 99%, or 100% identical to an HPV16 or HPV18 mRNA or a complement thereof. In another aspect, the HPV 16 or HPV 18 mRNA is selected from the group consisting of E2 and E6/E7 mRNA.

For present purposes, "stringent conditions" encompass conditions under which hybridization will only occur if there is 25% mismatch or less between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. Calculations regarding hybridization conditions required for attaining particular degrees of stringency are also discussed by Sambrook et al. (ed.), Molecular Cloning: A Laboratory Manual, 2nd ed., vol. 1-3, Cold Spring Harbor Laboratory Press, Cold Spring Harbor, N.Y., 1989, chapters 9 and 11, herein incorporated by reference in its entirety.

In an aspect, a probe set is provided, said probe set comprising at least one of the isolated nucleic acids disclosed herein. By way of example and not limitation, the probe set may comprise an isolated nucleic acid comprising, consisting essentially of, or consisting of at least one nucleotide sequence having at least 75%, at least 80%, at least 85%, at least 90%, or at least 95% homology to a nucleotide sequence selected from the group consisting of SEQ ID NO: 1 to SEQ ID NO: 105 and SEQ ID NO: 111 to SEQ ID NO: 308, RNA equivalents thereof, and complements thereof. In a further aspect, the probe set may comprise an isolated nucleic acid that comprises, consists, or consists essentially of a nucleotide sequence selected from the group consisting of SEQ ID NO: 1 to SEQ ID NO: 105 and SEQ ID NO: 111 to SEQ ID NO: 308, RNA equivalents thereof, and complements thereof. The isolated nucleic acids may be provided as unmodified probes or may be modified. By way of example and not limitation, the modification may facilitate isolation and/or detection of the probe and a nucleic acid to which it has hybridized, for example, by addition of a ligand and/or detectable labels. In one aspect, the probes may be provided bound to a solid support, such as a plate, tube, bead, microchip, or other solid surface.

Methods of Identifying HPV mRNA

Methods of the present disclosure may be used to detect the presence of a target nucleic acid from samples. Such nucleic acid may be an RNA, and such samples may include, without limitation, a specimen or culture (e.g., cellular, microbiological and viral cultures) including biological and environmental samples. Biological samples may be from a eukaryote, a prokaryote, an archaeon, a virus, an animal, including a human, a plant, a fungus, an excavate, and may be from fluid, solid (e.g., stool) or tissue, cell culture, liquid or solid media, as well as liquid and solid food and feed products and ingredients such as dairy items, vegetables, meat and meat by-products, and waste. Environmental samples include environmental material such as surface matter, soil, water, air and industrial samples, as well as samples obtained from food and dairy processing instruments, apparatus, equipment, utensils, disposable and non-disposable items. Particularly preferred are biological samples including, but not limited to, cervical epithelial cells (e.g., a sample obtained from a cervical swab or biopsy), adenoid cells, anal epithelial cells, blood, saliva, cerebral spinal fluid, pleural fluid, milk, lymph, sputum and semen. The sample may comprise a ribonucleic acid including messenger RNA (mRNA).

The present disclosure provides a method for determining the presence of a target RNA in a sample, wherein the method comprises: a) hybridizing the target RNA with a DNA capture probe having a sequence complementary to the target RNA to form a target RNA:DNA capture probe complex, wherein the DNA capture probe is conjugated to a support; b) separating the target RNA:DNA capture probe complex from unbound RNA (e.g., by washing); c) optionally hybridizing at least one amplification probe to the target RNA:DNA capture probe complex, wherein the at least one amplification probe has a sequence complementary to the target RNA, thereby forming a target RNA:DNA capture/amplification probe complex; d) adding an antibody that recognizes and binds to RNA:DNA hybrids to bind the target RNA:DNA capture/amplification probe complex, thereby forming a target RNA:DNA:antibody complex, wherein the antibody is labeled with a detectable marker; e) detecting the marker on said antibody, wherein the detecting indicates the presence of the target ribonucleic acid; and f) comparing the detection results with results produced from a different combination of amplification probes wherein the comparing indicates the particular RNA splice-form present.

The present disclosure provides a method for determining the presence of a target RNA in a sample, wherein the method comprises: a) hybridizing the target RNA with a DNA capture probe having a sequence complementary to the target RNA to form a target RNA:DNA capture probe complex, wherein the DNA capture probe is conjugated to a support; b) separating the target RNA:DNA capture probe complex from unbound RNA; c) optionally hybridizing at least one amplification probe to the target RNA:DNA capture probe complex, wherein the at least one amplification probe has a sequence complementary to the target RNA, thereby forming a target RNA:DNA capture/amplification probe complex; d) adding an antibody that recognizes and binds to RNA:DNA hybrids to bind the target RNA:DNA capture/amplification probe complex, thereby forming a target RNA:DNA:antibody complex; e) adding a second antibody that recognizes and binds the first antibody, wherein the second antibody is labeled with a detectable marker; f) detecting the marker on the second antibody, wherein the detecting indicates the presence of the target ribonucleic acid; and g) comparing the detection results with results produced from a different combination of amplification probes wherein the comparing indicates the particular RNA splice-form present.

The present disclosure also provides a method of detecting the presence of a ribonucleic acid (RNA) splice form in a sample, wherein the method comprises a) hybridizing the target RNA with a DNA capture probe having a sequence complementary to the target RNA under conditions that allow the probe and the target ribonucleic acid to hybridize, thereby forming a target RNA:DNA capture probe complex; b) adding a first antibody that recognizes and binds to RNA:DNA hybrids to bind the target RNA:DNA capture probe complex, thereby forming a target RNA:DNA capture probe:antibody complex, wherein the first antibody is conjugated to a support; c) separating the target RNA:DNA capture probe:antibody complex from unbound RNA; d) hybridizing at least one amplification probe to the target RNA:DNA capture probe:antibody complex, wherein the at least one amplification probe has a sequence complementary to the target RNA and is added in a combination that will cover specific target RNA regions, thereby forming a target RNA:DNA:antibody complex; e) adding a second antibody that recognizes and binds to RNA:DNA duplexes to bind the target RNA:DNA:antibody complex, to form a target RNA:DNA:antibodies complex, wherein the second antibody is labeled with a detectable marker; f) detecting the marker on said second antibody, wherein the detecting indicates the presence of the target RNA; and g) comparing the detection results with results produced from a different combination of amplification probes wherein the comparing indicates the particular RNA splice-form present.

The present disclosure also provides a method of detecting the presence of a ribonucleic acid (RNA) splice form in a sample, wherein the method comprises a) hybridizing the target RNA with a DNA capture probe having a sequence complementary to the target RNA under conditions that allow the probe and the target ribonucleic acid to hybridize, thereby forming a target RNA:DNA capture probe complex; b) adding a first antibody that recognizes and binds to RNA:DNA hybrids to bind the target RNA:DNA capture probe complex, thereby forming a target RNA:DNA capture probe:antibody complex, wherein the first antibody is conjugated to a support; c) separating the target RNA:DNA capture probe:antibody complex from unbound RNA; d) hybridizing at least one amplification probe to the target RNA:DNA capture probe:antibody complex, wherein the at least one amplification probe has a sequence complementary to the target RNA and is added in a combination that will cover specific target RNA regions, thereby forming a target RNA:DNA:antibody complex; e) adding a second antibody that recognizes and binds to RNA:DNA duplexes to bind the target RNA:DNA:antibody complex, to form a target RNA:DNA:antibodies complex; f) separating the target RNA:DNA:antibodies complex from unbound second antibody; g) adding a third antibody labeled with a detectable marker wherein the third antibody recognizes and binds to the second and/or first antibody; h) detecting the marker on the third antibody, wherein the detecting indicates the presence of the target RNA; and i) comparing the detection results with results produced from a different combination of at least one amplification probe wherein the comparing indicates the RNA splice-form present.

RNA is often transcribed from different promoters and spliced, thereby generating multiple forms that include the coding regions for different genes. It is important to characterize these multiple spliced forms of RNA for fundamental research and for applications where the detection of specific mRNA isoforms is critical.

One application of the present disclosure is the detection and characterization of mRNA expression in human papillomavirus (HPV). Carcinoma of the cervix has been shown to be associated with the presence of high-risk HPV types; from about 13 to about 18 high-risk types are currently identified. The HPV DNA test can identify high-risk HPV types, but is a poor predictor for the progression of the disease in pre-cancerous clinical specimens. Thus, additional methods and markers are needed to improve the predictive value of HPV tests. The characterization of mRNA for the presence of the E6/7 oncogene and other mRNAs, as provided by the present disclosure, will allow an accurate and reliable method that determines the ratio of expression of these oncogenes versus other viral genes. The ratio of E6/E7 to E2, E4, and/or L1 mRNA may be a better predictor for the progression of precancerous cervical lesions (see, e.g., U.S. Pat. No. 6,355,424, incorporated by reference herein). Hybrid capture technology is a linear signal amplification method. Thus, the instant disclosure provides valuable methods for guiding therapeutic strategy, while minimizing the number of patients requiring colposcopy. The instant disclosure provides methods of using mixtures of short oligonucleotides capable of hybridizing to the different lengths/genes of RNA (and mRNA in particular) in order to characterize splice forms.

Target Nucleic Acids

In one aspect, the target ribonucleic acid to be detected may be mRNA, ribosomal RNA, nucleolar RNA, transfer RNA, viral RNA, heterogeneous nuclear RNA etc., wherein the one or more polynucleotide probes are DNA probes. The target ribonucleic acids include, without limitation, nucleic acids found in specimens or cultures (e.g., cellular, microbiological and viral cultures) including biological and environmental samples. The target ribonucleic acids may be found in biological samples from an animal, including a human, fluid, solid (e.g., stool) or tissue, as well as liquid and solid food and feed products and ingredients such as dairy items, vegetables, meat and meat by-products, and waste. Target ribonucleic acids may be found in environmental samples and include environmental material such as surface matter, soil, water and industrial samples, as well as samples obtained from food and dairy processing instruments, apparatus, equipment, utensils, disposable and non-disposable items. Particularly preferred are target nucleic acids found in biological samples including, but not limited to cervical samples (e.g., a sample obtained from a cervical swab), adenoid cells, anal epithelial cells, blood, saliva, cerebral spinal fluid, pleural fluid, milk, lymph, sputum, urine and semen.

In other aspects, the target ribonucleic acids are from virus, bacteria, mycobacteria or plasmodia, for example, without intending to be limited thereby, cytomegalovirus (CMV), Herpesviridae, human immunodeficiency virus (HIV), *Chlamydia* spp., *Neisseria* spp. (e.g., *N. gonorrhea*), *Staphylococcus aureus*, mycobacteria (e.g., *Mycobacterium tuberculosis*), SARS coronavirus (SARS-CoV), or Orthomixoviridae (e.g., influenza viruses).

In one aspect, the target ribonucleic acids are human papillomavirus (HPV) and include genetic variants of HPV. A variant includes polymorphisms, mutants, derivatives, modified, altered, or the like forms of the target nucleic acid. In one aspect, the target nucleic acid is an HPV nucleic acid. In another aspect, the HPV nucleic acid is HPV DNA of a high risk HPV type. In another aspect the target nucleic acids are high risk HPV types 16, 18, 31, 33, 35, 39, 45, 51, 52, 56, 58, 59, 68, 26, 66, 73, and 82.

The RNA may be isolated and prepared for hybridization by a variety of methods and reagents including (but not limited to) guanidinium thiocyanate-phenol-chloroform extraction (e.g., with TRIzol® reagent, also known as TRI Reagent), hypotonic lysis, and carboxyl (COOH) bead capture. The principle of RNA isolation is based on cell/tissue lysis, followed by extraction, precipitation, and washing. While very effective, these techniques require a high level of technical precision and are not candidates for automation. Other RNA preparation methods do not completely eliminate DNA and other potential contaminants, require expensive enzymes, and require many sometimes time-consuming—washing steps. The challenge is to develop a method for mRNA detection that reduces many of the current challenges and can provide rapid information about expression of specific genes. Two primary sample preparation methods have been devised for the present disclosure: hypotonic cell lysis; and carboxyl bead capture. RNA isolated using TRIzol® or QIAGEN resin technology (for example, QIAGEN RNeasy Plus Mini Kit) can also be used in this assay.

In certain aspects, the biological sample is comprised of cervical cells, especially human cervical cells. The sample can be collected with any method or device known in the art, including a chemically inert collection device such as a Dacron® (poly(ethylene terephthalate)) tipped swab. Other acceptable collection devices may be used including, but not limited, to cotton swab, cervical brush, flocked swab (a swab shaped like a Dacron® swab but made with nylon fibers enabling collection of more cells and easier release of cells), cervical broom, mini broom, lavage, or any collection device often used in PAP smear testing (Papanicolaou's test). The cervical cells may also be part of a biopsy specimen.

Sample Preparation

Figure 5:
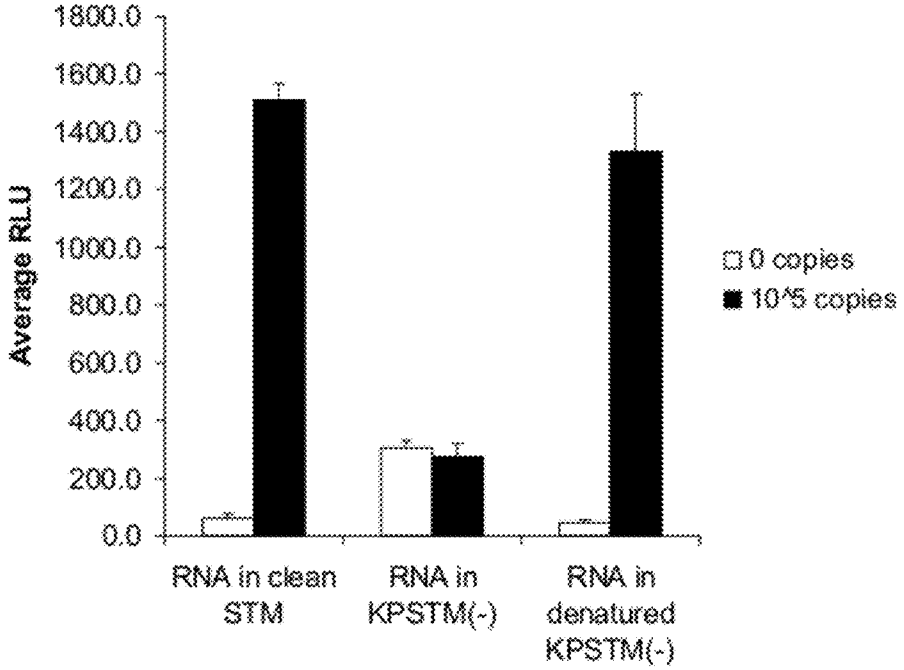
FIG. 5 shows that endogenous hybrids are often the source of clinical background noise. "RLU"=relative luminescence unit.
Figure 6:
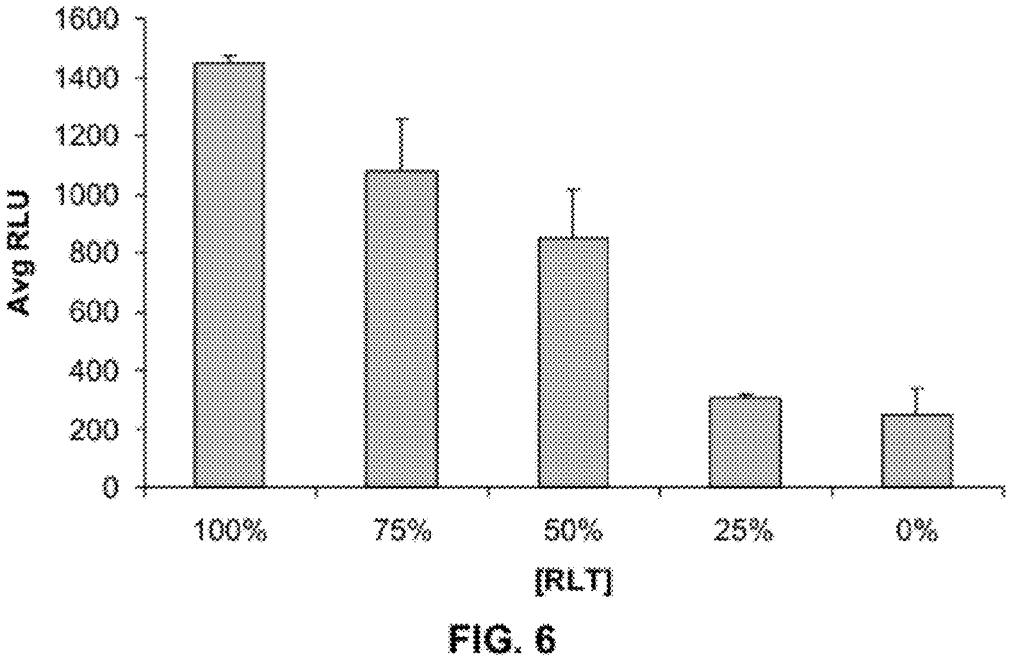
FIG. 6 shows the effect of lysis buffer (wherein 100% buffer contains about 3 M guanidine thiocyanate and about 2% detergent) concentration on assay background when assaying cellular samples in PreservCyt® Solution, and demonstrates that clinical background decreases with decreasing concentrations of lysis buffer.

The use of TRIzol® to isolate RNA, as well as other known methods for RNA isolation, may be employed in methods of the present disclosure. Sample preparation by hypotonic lysis of the cell pellet reduces the release of endogenous RNA:DNA hybrids that may interfere with assay detection step, and this is a preferable RNA isolation method. In this sample preparation method, cells are pelleted via centrifuge, the supernatant is removed, and the pellet is resuspended and the cells lysed. After lysis, the cellular debris is pelleted and the supernatant (containing RNA) collected. Reducing the stringency of lysis (as measured by salt and detergent concentrations in a buffer) reduces the clinical background produced from pools of methanol-based cervical specimens (FIGS. 5 & 6). The signal:noise ratios are also higher and the variability in background between pools and in interference is lower. Other studies have shown that hypotonic lysis works by rupturing the cellular membrane because of differences in tonicity between the cell and the milieu, making the cell permeable to macromolecules. Thus, RNA in the cell is released from the cell into the solution, whereas contaminants to the assay (such as endogenous RNA:DNA hybrids) will remain in the insoluble cell debris. This method may be useful in cases where the amount of RNA in a specimen is limited because increasing the amount of specimen does not lead to an increase in background.

Another method of sample preparation uses magnetic carboxyl (COOH) beads that can be added directly to a biological sample to concentrate cells for DNA isolation. Cells in the sample are attracted to the beads via hydrophobic interactions. After using a magnetic rack to pellet the beads, the supernatant can be removed and the cells lysed. Non-magnetic COOH beads or other adsorptive particles could also be used, substituting centrifugation for pelleting via a magnetic rack. After the lysis (which usually occurs at 65° C. for 15 min) the beads are again pelleted and the remaining supernatant may be used directly in methods of the present disclosure. While decreasing lysis stringency again reduces background in this method, water alone is not enough to release the RNA from the cells. As such, it is preferable to use a lysis buffer comprising about 1 M guanidine thiocyanate and about 0.7% detergent for all sample preparation methods of the present disclosure (see, e.g., FIGS. 5 & 6).

Hybridization/Capture—Capture Probes

After the sample is prepared and target RNA is released, it is contacted with at least one polynucleotide DNA capture probe under a condition sufficient for the at least one polynucleotide probe to hybridize to the target RNA in the sample to form a double-stranded nucleic acid hybrid. The DNA capture probes may be full length, truncated, or synthetic DNA. The DNA capture probes are sequence specific for the target RNA. DNA capture probes are ideally about 25 to 35 bases long and may be complementary to any region of the target RNA. The DNA capture probes may range from about 15 to about 200 bases in length. In other aspects, the capture probe may be not more than 100 or not more than 50 nucleotides in length. In yet other aspects, the capture probes may be: 20 to 100, 25 to 100, 30 to 100, 35 to 100, 40 to 100, 45 to 100, or 50 to 100 bases in length.

By way of example and not limitation, the capture probe may comprise, consist essentially of, or consist of at least one nucleotide sequence having at least 75%, at least 80%, at least 85%, at least 90%, or at least 95% homology to a nucleotide sequence selected from the group consisting of SEQ ID NO: 1 to SEQ ID NO: 20. In a further aspect, the capture probe comprises, consists of, or consists essentially of a nucleotide sequence selected from the group consisting of SEQ ID NO: 1 to SEQ ID NO: 20. In one aspect, a capture probe set specific for HPV 16 is provided, comprising at least one capture probe selected from the group consisting of SEQ ID NO: 1 to SEQ ID NO: 10. In one aspect, a capture probe set specific for HPV 18 is provided, comprising at least one capture probe selected from the group consisting of SEQ ID NO: 11 to SEQ ID NO: 20.

Figure 3:
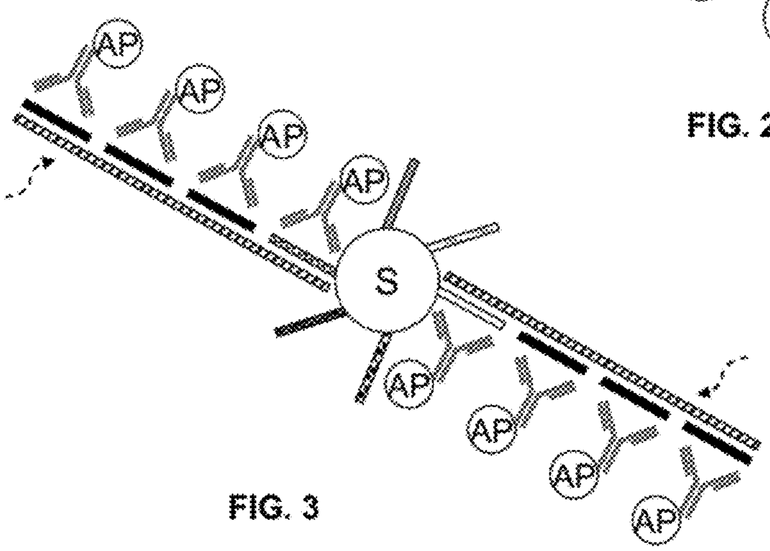
FIG. 3 is a diagram of target RNAs (dashed arrows) captured by different DNA capture probes bound to a substrate (S). Non-conjugated DNA amplification probes (black bars) and multiple antibodies that detect and bind to DNA:RNA hybrid regions (conjugated to alkaline phosphatase or any other appropriate detectable moiety, such as horseradish peroxidase, etc.) are also shown. The substrate (e.g., a bead) may bear multiple DNA capture probes, and the DNA capture probes may be the same (i.e., the same sequence and/or length) or different (i.e., different sequences and/or different lengths).
Figure 4:
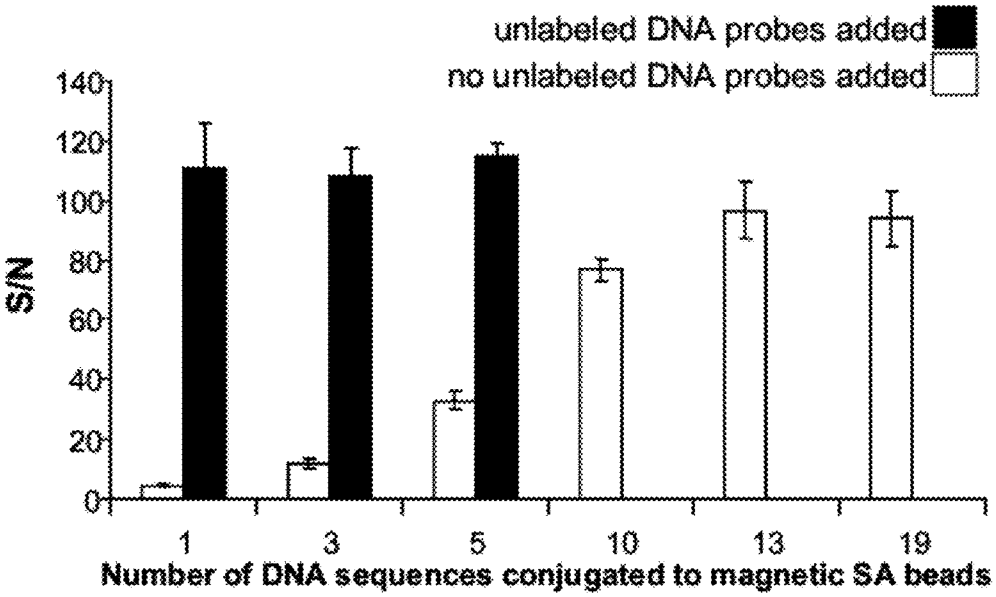
FIG. 4 provides the results of an experiment showing the effect of adding unbiotinylated DNA probes after RNA capture. In this experiment, a variable number of biotinylated probes were conjugated to streptavidin beads. The target was the E6/7 gene transcript of HPV 16. The assay was performed with each set of beads with (black bars) and without (white bars) the addition of unlabeled signal amplification probes (one- versus two-step assay). When no signal amplification step was added (white bars), the signal increased with the amount of coverage provided by the capture probes. However, when signal amplification probes were added (black bars), the signal was greater than if they were not added, and they enable a higher signal with fewer (3-5) capture probes.

The DNA capture probes can be bound to a support. "Bound" includes but is not limited to chemically attached, covalently bound, and covalently linked. Multiple DNA capture probes, and multiple different DNA capture probes may be bound to the same support (e.g., the same magnetic bead), as shown schematically in FIG. 3. Only 3-5 different capture probes are required for optimal results (see FIG. 4), thus providing a great deal of flexibility to allow these probes to be sequence-specific and not fall in regions that may be spliced out in some variants. In one aspect, the sequence-specific DNA capture probes are biotinylated and have been bound by conjugation to magnetic streptavidin beads. A capture probe may isolate a particular spliceform if it comprises a single oligo that bridges a splicesite.

Supports include, but are not limited to beads, magnetic beads, columns, plates, filter paper, polydimethylsiloxane (PDMS), and dipsticks. Any support can be used as long as it allows extraction of the liquid phase and provides the ability to separate out bound and unbound capture probes or antibodies. Magnetic beads are particularly useful in that they can be left in the solution and the liquid phase can be extracted or decanted, if a magnetic field is applied to hold the beads in place. Beads that are small and have a high surface area are preferable, such as beads about 1 μm in diameter. In certain aspects, the support comprises a modified magnetic bead, that is coated or has attached thereto a DNA capture probe complementary and specific to the target mRNA. A magnetic field is used to separate the double-stranded nucleic acid/magnetic bead complex from non-bound ribonucleic acid. In certain aspects, the support comprises a modified magnetic bead, wherein the magnetic beads are modified by coating the beads with a first antibody immunospecific for double-stranded hybrid nucleic acids. A magnetic field is used to separate the nucleic acid hybrid/antibody/magnetic bead complex from unbound ribonucleic acid. Other beads that employ charge switching or silica capture (as opposed to magnetic fields) may be used as well. In another aspect, magnetic beads with detection capacity (such as magnetic Lumonex beads) may capture and detect specific spliceforms.

Following capture of the target RNA or the target RNA:DNA hybrid as described above, the captured target RNA or RNA:DNA hybrid may be separated from the rest of the sample by application of a magnetic field (in the case of magnetic beads), and washing away of non-captured nucleic acids. Washing away unwanted interfering substances may be accomplished with buffers containing salt and or detergent that are used at various temperatures. When using supports other than magnetic beads, alternative methods of separating captured hybrid from the rest of the sample are conducted, including but not limited to, washing. Enzymatic processes, such as dnase for double-stranded DNA or RNA:DNA may be used to facilitate isolation of target RNA.

Hybridization/Capture—Amplification Probes

After the wash step to ensure that only the target remains, signal amplification DNA probes are hybridized to the target mRNA, wherein the signal amplification probes are unlabeled DNA probes complementary and/or specific to the target mRNA. The amplification probe need not be specific to the target nucleic acid. For example, the DNA amplification probe may be able to bind other nucleic acids other than the designed target. The DNA signal amplification probes complementary to the mRNA regions are designed and combined in mixtures that will cover specific genes. By extending and varying the coverage, one can determine which genes are present and the particular splice forms of the RNA. "Coverage" is defined as the extent or length of target sequence which is flanked by the complementary signal probes. The signal amplification probes are roughly 40 bases in length, but because they are designed around the capture probes, some may be more or less than 40 bases. Signal amplification probes may be about 15 to about 200 bases in length. In yet other aspects, the signal amplification probes may be: 20 to 100, 25 to 100, 30 to 100, 35 to 100, 40 to 100, 45 to 100, or 50 to 100 bases in length. Increasing coverage (i.e., hybridizing more signal probes to complementary regions of the target RNA) will lead to an increase in signal. Therefore, it is preferable to use more probes to obtain an amplified signal. The limit of detection depends, in part, on the length of the target nucleic acid (i.e., the target gene).

By way of example and not limitation, the amplification probe may comprise, consist essentially of, or consist of at least one nucleotide sequence having at least 75%, at least 80%, at least 85%, at least 90%, or at least 95% homology to a nucleotide sequence selected from the group consisting of SEQ ID NO: 21 to SEQ ID NO: 105. In a further aspect, the amplification probe comprises, consists of, or consists essentially of a nucleotide sequence selected from the group consisting of SEQ ID NO: 21 to SEQ ID NO: 105. In one aspect, an amplification probe set specific for HPV 16 is provided, comprising at least one amplification probe selected from the group consisting of SEQ ID NO: 21 to SEQ ID NO: 62. In one aspect, an amplification probe set specific for HPV 18 is provided, comprising at least one amplification probe selected from the group consisting of SEQ ID NO: 63 to SEQ ID NO: 105.

Figure 12:
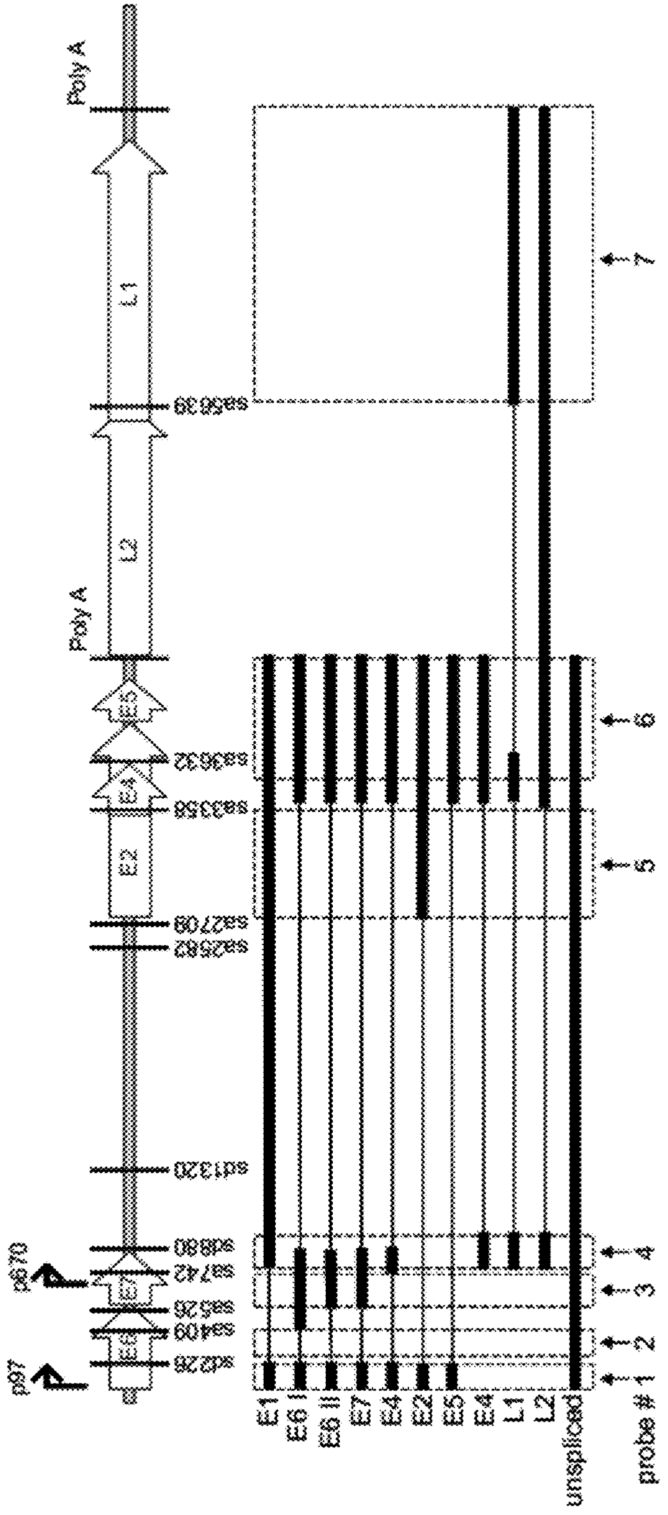
FIG. 12 is a diagram depicting capture and signal amplification probe design regions. The length of HPV transcripts can be "characterized" by capture onto magnetic beads with specific capture oligos that capture specific targets and detected with various sets of unlabeled oligonucleotides used to extend the length of the hybrid region. Signal will result if the capture RNA bears the sequence that is complementary to the capture probes that are used. Signal output will increase with successive addition of amplification signal probes until maximum length is reached where the signal will plateau. The various HPV transcripts for HPV 16 are shown. The regions denoted by the dashed boxes are designated for probe design.

Amplification signal probes are added in combinations which would extend over the genetic sequence of known RNA splice-forms. The combination of signal amplification probes will determine the extent of coverage on the target mRNA and hence, signal output. Comparison of the resulting signal output from different combinations of amplification probes will indicate the presence of particular mRNA splice-form variants. In this way, this method is a "molecular ruler" in that the signal output is dependent on the splice form present. For example, capture probe 3 is expected to hybridize with E6/7 target mRNA, but not with E1, E2, E4, E5, L1, or L2 (see, e.g., TABLE 3 and FIG. 12). Signal amplification probes 1 and 6, used after hybridization with capture probe 3, will generate a strong signal from the spliced E6/7 form, and a weak signal from the spliced/integrated E6/7 form. By varying the combinations and numbers of capture probes and amplification probes, the signal output provides information about which viral genes are being expressed (e.g., the ratio thereof), as well as which splice forms of those genes are expressed. Such information, coupled with clinical and experimental data, is expected to provide a better predictor for progression of precancerous cervical lesions.

The characterization of gene expression in cells via measurement of mRNA levels is a useful tool in determining whether cells are infected with a pathogen, and the state of disease progression.

The present disclosure provides a method of determining lengths of gene transcripts for known and unknown splice form variants. A reliable and robust method for measuring the expression of alternatively spliced transcripts is an important step in investigating the significance of each variant. So far, accurate quantification of splice variants, such as Northern blotting, RT-PCR and real time RT-PCR, has been laborious and difficult due to the intrinsic limitations of conventional methods. The present disclosure provides methods of determining the presence of splice form variants. For example, the question of whether an early HPV transcript (for example HPV E6*I) bears late-gene sequences may be determined by capturing the transcript with capture probes complimentary to the early region, then detecting with amplification probes that are complementary to the late region; resulting signal may indicate the presence of late regions on early gene transcripts. Furthermore, by providing a combination of degenerate signal amplification probes that would cover predicted splice form sequences, the presence of a splice variant could be determined. Furthermore, the absence of a region may be indicated by lack of capture by select DNA probes.

The resulting hybrids are captured/detected using molecules that recognize RNA:DNA hybrids. Molecules specific for the double stranded nucleic acid hybrids include, but are not limited to, monoclonal antibodies, polyclonal antibodies, proteins such as but not limited to RNAse H, nucleic acids including but not limited to aptamers, or sequence specific nucleic acids. Aptamers are short oligonucleotide or peptide molecules that bind to a particular target molecule. They are often created by selecting them from large pools of random sequences, although naturally-occurring aptamers (e.g., riboswitch aptamers) are known.

Hybridization/Capture—Anti-Hybrid Antibody

In one aspect the molecule specific for the double stranded nucleic acid hybrid is an antibody ("anti-hybrid antibody"). The hybrids are incubated with the anti-hybrid antibody for a sufficient amount of time to allow binding to the double-stranded nucleic acid hybrids. The anti-hybrid antibody may be monoclonal or polyclonal. In a most preferred aspect the antibody is monoclonal.

In another aspect, the first antibody is bound to a support. In this aspect, after the sample is prepared and RNA is released, it is contacted with at least one polynucleotide DNA capture probe under conditions sufficient for the at least one polynucleotide probe to hybridize to the target RNA in the sample to form a double-stranded nucleic acid hybrid. The target RNA, in the form of a target RNA:DNA capture probe complex is separated from unbound RNA by washing. After the wash step to ensure that the only RNA remaining is target RNA, signal amplification DNA probes are hybridized to the target RNA, wherein the signal amplification probes are unlabeled DNA probes that are complementary and/or specific to the target RNA. The hybridization of capture and amplification probes to the target RNA creates double stranded nucleic acid hybrids. The resulting hybrids are detected using molecules that recognize RNA:DNA hybrids. In a preferred aspect the molecule specific for the double stranded nucleic acid hybrid is an antibody ("anti-hybrid antibody"). The hybrids are incubated with the anti-hybrid antibody for a sufficient amount of time to allow binding to the double-stranded nucleic acid hybrid regions. The anti-hybrid antibody is conjugated to a support and binding to the RNA:DNA hybrids forms an RNA:DNA hybrid:antibody complex. The complex is separated from unbound antibody. In applications where the support is a magnetic bead, a magnetic field is used to separate out any unbound antibody.

Detection

After unbound anti-hybrid antibody is removed, a second antibody is added, wherein the second antibody is labeled with a detectable marker and recognizes and binds to the first antibody. The label present on the second antibody is detected to thus indicate the presence of the target ribonucleic acid. Methods for detecting various labels are known in the art. For example, colorimetry, radioactive, surface plasmon resonance, or chemiluminescence methods are described by e.g., Coutlee, et al., J. Clin. Microbiol. 27:1002-1007 (1989).

For example, antibodies conjugated with at least one alkaline phosphatase molecule can be detected by chemiluminescence with a reagent such as a Lumi-Phos™ 530 reagent (Lumigen, Detroit, Mich.) or DR2 (Applied Biosystems, Foster City, Calif.) using a detector such as an E/Lumina™ luminometer (Source Scientific Systems, Inc., Garden Grove, Calif.), an Optocomp I™ Luminometer (MGM Instruments, Hamden, Conn.), or the like. As described herein, detection of the label on the second antibody is indicative of the presence of one or more of the target ribonucleic acids in the sample that are complementary to the one or more probes. Following washing, the sample is suspended in a detection buffer that for example, contains the substrate for the label on the second antibody.

Anti-hybrid antibodies can be used and/or coupled to magnetic beads and/or immobilized on a support in the present assay as described below. In a preferred aspect, the antibodies used for capture and detection of the target nucleic acid are monoclonal antibodies. The first and second antibodies may be the same for capture and detection (i.e., produced by the same hybrid myeloma cell line) or may be from different and produced by different hybrid myeloma cell lines. In a most preferred aspect, the first and second monoclonal antibodies used for capture and/or detection are the same and are specific for RNA/DNA hybrids. Also included are immunofragments or derivatives of antibodies specific for double-stranded hybrids, where such fragments or derivatives contain binding regions of the antibody.

For example, a monoclonal RNA:DNA hybrid antibody derived from myeloma cells fused to spleen cells that are immunized with an RNA:DNA hybrid can be used. The hybrid-specific antibody can be purified by affinity purification against RNA:DNA hybrids immobilized on a solid support, for example as described in Kitawaga et al., Mol. Immunology, 19:413 (1982); and U.S. Pat. No. 4,732,847, each of which is incorporated herein by reference.

Other suitable methods of producing or isolating antibodies, including human or artificial antibodies, can be used, including, for example, methods that select recombinant antibody (e.g., single chain Fv or Fab, or other fragments thereof) from a library, or which rely upon immunization of transgenic animals (e.g., mice) capable of producing a repertoire of human antibodies (see, e.g., Jakobovits et al., Proc. Natl. Acad. Sci. USA, 90:2551 (1993); Jakobovits et al., Nature, 362: 255 (1993); and U.S. Pat. Nos. 5,545,806 and 5,545,807).

In yet another aspect, the present disclosure provides kits that allow for the detection of ribonucleic acids in a biological sample or a sample containing nucleic acids. In a preferred aspect, the kit comprises a) a DNA capture probe conjugated to a magnetic bead; b) a DNA amplification probe; c) a first anti-hybrid antibody; d) a detection reagent comprising a second antibody, wherein the second antibody binds the first antibody and is detectably labeled; e) a detergent-based wash buffer and; f) a second detection reagent comprising a substrate for the label on the second antibody. A preferred detergent-based wash buffer is 40 mM Tris-HCl, 100 mM NaCl, 0.5% Triton X-100.

In certain aspects, detection methods of the present disclosure detect RNA by first capturing the target onto complementary biotinylated DNA probes that are conjugated to magnetic streptavidin beads. This probe-bead complex may be preconjugated and is stable at 4° C. for several months. This capture step is preferably performed at 60° C. with constant shaking and allowed to proceed for about 30 minutes (a time sufficient to allow capture). The beads with the captured target are then washed so that any non-target RNA sequences are removed. Because the hybrid capture antibody binds to individual DNA-RNA hybrids, it is preferable to cover the target region with DNA amplification probes to achieve the maximal signal (see FIGS. 1 & 2). Thus, additional probes are then hybridized to the target mRNA. Because only the target is captured at this point, these probes need not be sequence-specific but rather may cover the full length of the gene, excluding regions that are already covered by the biotinylated specific probes. The signal amplification probes are complementary to the mRNA regions and are designed and combined in mixtures that will cover specific genes. By extending and varying the coverage, particular genes and particular splice variants can be determined. These "signal amplification" probes are preferably used at concentration of 4.2 nM. This hybridization also preferably occurs at 60° C. for 30 min at a pH of around 7.8. The hybridization is then followed by detection with the hybrid capture antibody system discussed above (use of anti-hybrid antibody and a second antibody to detect the anti-hybrid antibody).

Method for Determining the Presence, Disruption, or Absence of a Target Nucleic Acid In another aspect, a method for determining the presence or absence of a target nucleic acid in a sample is provided, said method comprising: (a) treating a first portion of the sample under conditions sufficient to induce the formation of: (α) a first set of DNA:RNA hybrids comprising the target nucleic acid; and (β) a second set of DNA:RNA hybrids comprising a reference nucleic acid; (b) treating a second portion of the sample under conditions sufficient to induce the formation of the second set of DNA:RNA hybrids, but not the first set of DNA:RNA hybrids; (c) generating a detectable signal in the first portion of the sample and the second portion of the sample, wherein the detectable signal has an intensity that correlates with the concentration of DNA:RNA hybrids; and (d) comparing the intensity of the detectable signal in the first portion of the sample and the intensity of the detectable signal in the second portion of the sample, wherein: (α) the target nucleic acid is present in the sample if the intensity of the detectable signal in the first portion of the sample is greater than the intensity of the detectable signal in the second portion of the sample; and (β) the target nucleic acid is absent from the sample if the intensity of the detectable signal in the first portion of the sample is less than or equal to the intensity of the detectable signal in the second portion of the sample.

As used herein, a "portion of a sample" shall refer to the sample separated in any manner. For example, the sample may be separated into equal portions according volume and/or mass. Alternatively, the different portions may be generated by extracting different constituents from the sample. By way of example and not limitation, the "portion of a sample" may refer to a collection of target nucleic acids and reference nucleic acids bound to a support and separated from the rest of the sample. Regardless of how the portion is generated, each portion should comprise roughly equal amounts of reference nucleic acid.

In one exemplary aspect, the first portion of the sample and the second portion of the sample are formed by a method comprising contacting the sample with: (a) a first capture probe specific for the target nucleic acid under stringent conditions, wherein hybridization of the first capture probe to the target nucleic acid generates a first capture complex; and (b) a second capture probe specific for the reference nucleic acid under stringent conditions, wherein hybridization of the second capture probe to the reference nucleic acid generates a second capture complex. The capture complexes may then be bound to the support.

The first and/or second capture probes may be provided covalently bound to the support or may alternatively be adapted to be bound to the support. By way of example and not limitation, the capture probes may be modified with a ligand and the support coated with a moiety capable of binding to the ligand. In such a configuration, the capture probe is bound to the support by virtue of the association between the ligand and the ligand binding moiety. By way of example and not limitation, the ligand may be biotin and the ligand binding moiety is a molecule capable of binding biotin, such as avidin and streptavidin. If desired, the first and second capture probes may have different ligands. In such a case, a first support can be provided capable of binding to both the first and second capture probes, while a second support is provided capable of binding only the second capture probe. In such a manner, a further level of specificity may be added.

In certain other aspects, the capture probe forms a DNA:RNA hybrid with the target and/or reference nucleic acids. In such a configuration, the portions of the sample may be formed by contacting the sample with a support modified by an entity capable of binding to a DNA:RNA hybrid, such as an antibody (or fragment thereof) immunospecific for double-stranded hybrid nucleic acids. The DNA:RNA hybrid formed by the capture probe and the target and/or reference nucleic acid may then be bound to the support and separated from the rest of the sample via binding of the antibody. The antibody may be covalently bound to the support, bound by virtue of a ligand/ligand-binding moiety, or bound by an entity capable of binding to an antibody, such as an Ig-specific antibody, that is coated to the support.

In another aspect, the support is coated with a nucleic acid, referred to herein as an anchor probe. In such a configuration, the capture probes may be designed with sequences capable of hybridizing to at least a portion of the anchor nucleic acid, thereby binding the capture complex to the support. In such a configuration, the capture probe may comprises: (α) a region capable of hybridizing to the target and/or reference nucleic acid under stringent conditions; and (β) a region capable of hybridizing to a sequence of the anchor probe. The anchor probe for each capture probe may be the same, or it may be different. Additionally, each capture probe may comprise a sequence capable of hybridizing to a different sequence of the same anchor probe. The different sequences may be disposed in the same or in different anchor probes.

In another exemplary aspect: (a) the first portion of the sample is formed by a method comprising capturing the first capture complex and the second capture complex to a first support; and (b) the second portion of the sample is formed by a method comprising capturing the second capture complex, but not the first capture complex, to a second support. In such an aspect, the first support may comprise the first and second capture probes covalently bound thereto (or entities capable of capturing the same), while the second support may comprise the second capture probe, but not first capture probes (or entities capable of capturing the same), bound thereto. Alternatively, the first and second supports may be substantially identical. In such a case, the sample should be first separated and then contacted with the appropriate capture probes before being contacted with the respective supports.

In another aspect, the first and second portions of the sample are formed by a method comprising: (a) capturing the first capture complex and the second capture complex to a first support to form the first portion of the sample; and (b) capturing the first capture complex and the second capture complex to a second support to form the second portion of the sample.

Where the portions of the samples are formed by capture to a support, the capture complexes may optionally be washed to remove non-captured nucleic acids. Washing away unwanted interfering substances may be accomplished with buffers containing salt and or detergent that are used at various temperatures.

Once the sample has been separated into the first and second portions and optionally washed, the target and/or reference nucleic acids are detected by forming a first set of DNA:RNA hybrids comprising the target nucleic acid and a second set of DNA:RNA hybrids comprising the reference nucleic acid.

In one aspect, the DNA:RNA hybrids are formed by contacting the portions of the sample with a signal probe capable of forming a DNA:RNA hybrid with the target and/or reference nucleic acid. As used herein, the term "signal probe" refers to any oligo- or polynucleotide capable of hybridizing to the target or reference nucleic acid under stringent conditions to form a DNA:RNA hybrid. The signal probe may be, but is not required to be, specific for the target or reference nucleic acid. For example, the signal probe may be able to bind other nucleic acids other than the designed target. Signal probes preferably are about 15 to about 200 bases in length. In some aspects, the signal probes are designed to be from 35 to 40 nucleotides in length. In other aspect, a signal probe set is provided, comprising a plurality of signal probes capable of hybridizing to distinct regions of the target and/or reference nucleic acids In one aspect: (a) the first set of DNA:RNA hybrids is formed by a method comprising contacting the sample with a first signal probe capable of hybridizing to the target nucleic acid; and (b) the second set of DNA:RNA hybrids is formed by a method comprising contacting the sample with a second signal probe capable of hybridizing to the reference nucleic acid. In each case, the first portion of the sample should be contacted with both the first and the second signal probes. Where the second portion of the sample comprises both the target and the reference nucleic acids, it should be not be contacted with the first signal probe.

Once the DNA:RNA hybrids are formed, a detectable signal is generated, the intensity of which correlates with the total concentration of DNA:RNA hybrids in the portion of the sample. Where the intensity of the detectable signal is the same or greater in the second portion of the sample as compared to the first portion of the sample, the target nucleic acid is absent. On the other hand, where the intensity of the detectable signal is the less in the second portion of the sample as compared to the first portion of the sample, the target nucleic acid is present.

In some aspects, a plurality of signal probes are designed so as to cover a substantial portion of the target and/or reference nucleic acid. By extending and varying the coverage, one can determine the approximate portion of the target nucleic acid present. Increasing coverage (i.e., hybridizing more signal probes to complementary regions of the target nucleic acid) will lead to an increase in signal. Therefore, it is preferable to use more probes to obtain an amplified signal. The limit of detection depends, in part, on the length of the target nucleic acid (i.e., the target gene). In an aspect, the probe sets comprise probes sufficient to cover at least 70-percent of the target and/or reference nucleic acids. In other aspects, the probe sets comprise sufficient to cover at least at least 75-percent, at least 80-percent, at least 85-percent, at least 90-percent, and at least 95-percent of the target and/or reference nucleic acids. In other aspects, the signal probes of the probe sets are designed to have an average length of from 20 to 50 nucleotides in length.

In an aspect, signal probes are added in combinations which would extend over the genetic sequence of a target mRNA suspected of being truncated or alternately spliced. The combination of signal probes will determine the extent of coverage on the target mRNA and hence, signal output. Comparison of the resulting signal output from different combinations of signal probes will indicate the presence of particular mRNA splice-form variants. In this way, this method is a "molecular ruler" in that the signal output is dependent on the splice form present.

The present disclosure also provides an assay for determining whether a high-risk HPV E2 gene is expressed or disrupted in a host cell, wherein the target nucleic acid is an E2 mRNA and the reference nucleic acid is selected from the group consisting of HPV E1, HPV E6/E7, HPV L1, and HPV L2 mRNAs. Such methods may also be applied to detecting integration of HPV into a host cell genome and/or predicting onset of HPV-related cell transformation and/or cancer, for example cervical cancer. High-risk HPV types include, but are not necessarily limited to, HPV 16, 18, 31, 33, 35, 39, 45, 51, 52, 56, 58, 59, 66, 68, and 82.

In certain aspects, detection methods of the present disclosure detect mRNA by contacting the sample with a biotinylated DNA capture probe complementary to the target nucleic acid and a biotinylated DNA capture probe complementary to the reference nucleic acid, wherein the capture probes are conjugated to magnetic streptavidin beads. The probe-bead complexes may be preconjugated and are stable at 4° C. for several months. This capture step is preferably performed at 60° C. with constant shaking and allowed to proceed for about 30 minutes (a time sufficient to allow capture). The beads with the captured target are then washed so that any non-target/reference RNA sequences are removed. The bead captured targets/reference nucleic acid complexes are then separated into multiple equal portions. Each portion of the sample is then contacted with DNA signal probes sufficient to cover a significant portion of the reference mRNA. The portions are also contacted with DNA signal probes sufficient to cover a progressively increasing portion of the target mRNA. At least one portion should not be contacted with signal probes capable of hybridizing to target mRNA. Because only the target and/or reference mRNA are captured at this point, these probes need not be sequence-specific but rather may cover the full length of the mRNA, excluding regions that are already covered by the biotinylated specific probes. These signal probes are preferably used at concentration of around 4.2 nM. This hybridization also preferably occurs at 60° C. for 30 min at a pH of around 7.8. The hybridization is then followed by detection with the hybrid capture antibody system discussed above (use of anti-hybrid antibody and a second antibody to detect the anti-hybrid antibody).

It will be understood to those skilled in the art that the present invention can be carried out on a number of platforms including, but not limited to, tubes, dipsticks, microarrays, microplates, 384 well plates, other microtiter plates and microfluidic systems. It will be understood to those skilled in the art that the present, as relevant to developing countries, can utilize low technology methods such as dropper bottles, rubber bulbs, Pasteur pipettes, or squirt bottles for steps involving movement of liquid. These devices deliver relatively precise volumes within the approximate ranges that are needed for the assay. In an aspect, the methods of the disclosure do not include automatic pipettors or other battery powered or energy powered pipetting devices.

Example 1

Sample Preparation Via Hypotonic Lysis of Cell Pellet

Figure 7:
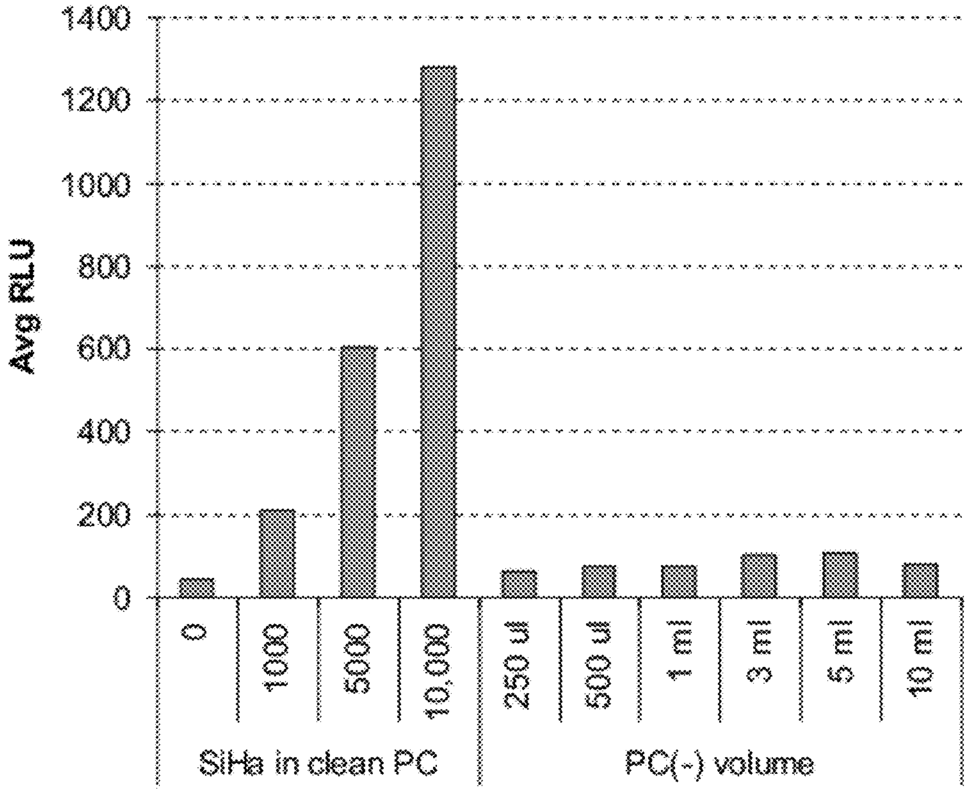
FIG. 7 shows that hypotonic lysis of cell pellets ensures that background noise remains low and stable, and that the background does not change significantly regardless of the amount of specimen used. "PC"=PreservCyt® Solution; "PC(−)"=Specimen (cervical scrape) pool fixed in PreservCyt® Solution with no HPV target.
Figure 8:
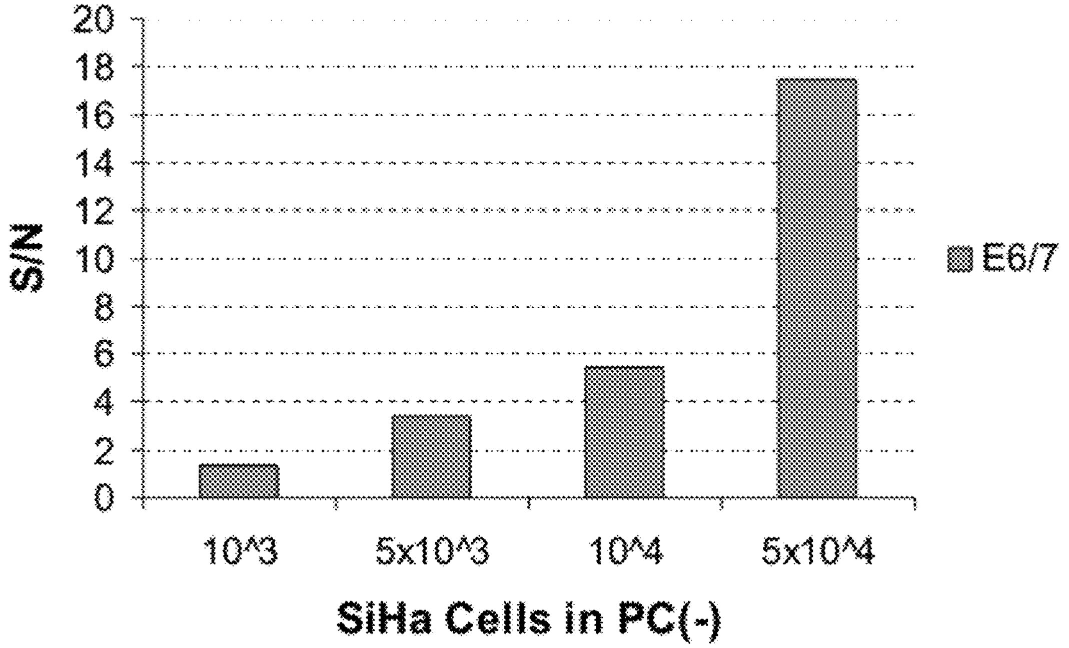
FIG. 8 shows limit of detection of HPV E6/E7 from HPV positive cells (SiHa). This shows that using the methods of the present disclosure, as little as $1\times10^3$ cells are required for HPV E6/7 RNA detection.

Endogenous hybrids present a unique challenge to detection assays because they will be detected by the hybrid capture antibody. Thus, sample preparation preferably inactivates the background of endogenouse hybrids by preventing them from adding to signal by sequestration, binding, or degradation. Hypotonic lysis relies on the former strategy. In this method, cells are pelleted via centrifuge, the supernatant is removed, and the pellet is lysed. As is shown in FIG. 6, reducing the stringency of lysis by varying salt and detergent concentrations in a buffer reduces the clinical background produced from pools of methanol-based cervical specimens. The signal:noise ratios are also higher and the variability in background between pools and in interference is lower (TABLE 2). Other studies have shown that hypotonic lysis works by rupturing the cellular membrane because of differences in cellular tonicity compared to the milieu, making the cells permeable to more soluble mRNA, but less soluble to endogenous hybrids and nuclear DNA. Thus, RNA in the cell is released from the cell into solution, whereas contaminants to the assay such as hybrids will remain with the insoluble cell debris. This method may be useful in cases where the amount of RNA in a specimen is limited because increasing the amount of specimen does not lead to an increase in background (FIG. 7). Using a model of spiking HPV positive cells into pools of negative cervical specimens, hypotonic lysis followed by detection methods of the present disclosure can detect HPV E6/7 RNA from just 1000 cells (FIG. 8).

Example 2

Sample Preparation Via Magnetic Carboxyl Beads

Figure 10:
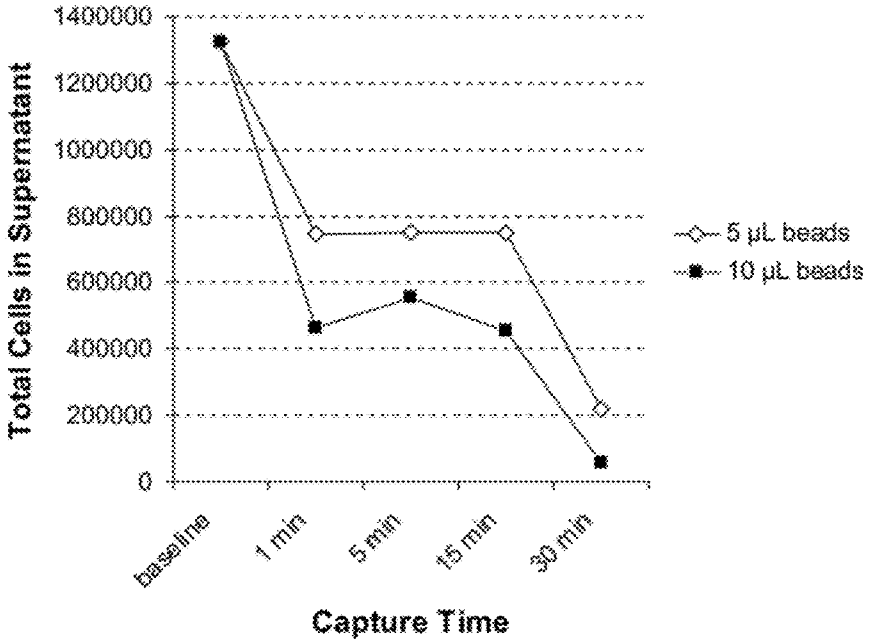
FIG. 10 shows cell capture by magnetic carboxylate-modified (COOH) beads (Sera Dyn catalog number 6515-2105-050350), over time, demonstrating that about 95% of the cells have been captured after incubation of 30 minutes.
Figure 11:
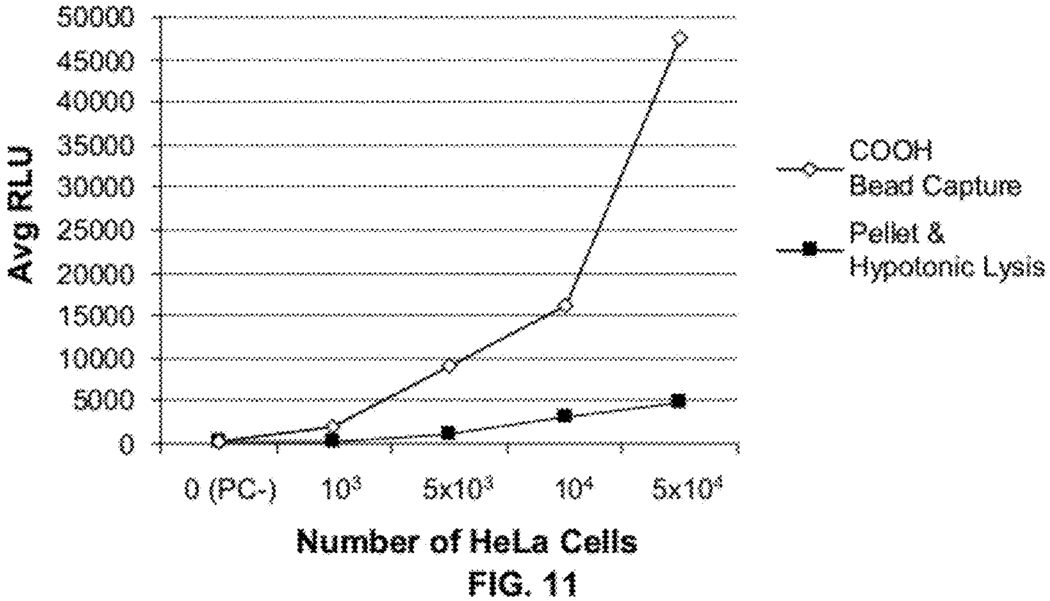
FIG. 11 shows comparison of COOH bead capture with hypotonic lysis, and indicates that COOH bead capture is more efficient than hypotonic lysis for obtaining mRNA from cells. "PC-" indicates a pool of cervical scrape specimens that lack presence of HPV.

Another sample preparation method that has been characterized for use in the methods of the present disclosure uses magnetic carboxyl modified (COOH) beads that can be added directly to a biological sample (e.g., Sera-Mag® Magnetic Carboxylate-Modified Particles; Thermo Fisher Scientific, Inc.). Cells in the sample are attracted to the beads via hydrophobic interactions. After using a magnetic rack to pellet the beads, the supernatant can be removed and the cells lysed. After lysis, the beads are again pelleted and the remaining supernatant is transferred for use in methods of the present disclosure. While decreasing lysis stringency again reduces background in this method (see TABLE 1), water alone is insufficient to release RNA from the cells. Figures in Table 1 represent percents of a 2% solution, not final solutions. Rather, a preferred lysis buffer is about 1 M guanidine thiocyanate and about 0.7% detergent (see FIG. 9), as it supports both lysis and hybridization. Stronger lysis buffer concentrations may be used if it is diluted before the hybridization capture step. As shown in FIG. 10, the capture of cells onto the beads is a biphasic reaction. Carboxyl beads were spiked directly into PreservCyt®-based samples of cervical cells. Approximately 50-60% of all the cells in the samples were attracted to the beads within the first minute of exposure. This process plateaus for at least 15 min, but approximately 30 min after adding the beads at least 95% of the cells have been captured (as measured by counting cells remaining in the supernatant; see FIG. 10). FIG. 11 shows that using methods of the present disclosure results could be obtained using only approximately 1000 HPV positive cells; carboxyl bead cell capture, followed by detection methods of the present disclosure, is more efficient at obtaining mRNA from cells than hypotonic cell lysis followed by detection methods of the present disclosure (see FIG. 11).

TABLE 1

| % Lysis Buffer | S/N |
|---|---|
| 100 | 1.6 |
| 50 | 3.2 |
| 32.5 | 7.0 |
| 25 | 1.7 |
| 0 | 0.9 |

Example 3

Effects of Endogenous Hybrids on Assay Background

Endogenous hybrids are often the source of clinical background noise (see FIG. 5). When HPV 16 E6/7 RNA is spiked into clinical pools (with no HPV; KPSTM(−)), the background is high and the signal is masked. However, when the pools are denatured (1.75 M NaOH) and neutralized before the RNA addition, the background is low and the signal is rescued. This reveals the need to eliminate or prevent release of endogenous nucleic acid hybrids before utilizing a detection method that employs antibodies that recognize nucleic acid hybrids.

Example 4

Effect of Lysis Buffer Concentration on Background

Reducing lysis stringency reduces clinical background noise (see FIG. 6). One mL of methanol-based cervical specimens were spun down and the pellets resuspended in buffer at various concentrations (100% buffer=about 3 M guanidine thiocyanate+about 2% detergent), as shown along the x-axis. Pelleted cells were heated for 15 min at 65° C. The final concentration of lysis buffer was then adjusted to 32.5% for the capture of RNA according to methods of the present disclosure. As shown in FIG. 6, the background decreased with decreasing concentrations of lysis buffer. This experiment provides evidence that hypotonic lysis of cells was successful in preventing release of endogenous nucleic acid hybrids. RNA in the cytoplasm is released from the cell whereas contaminants to the assay such as hybrids will remain in the nucleus.

In addition, water lysis gives lower background and variability and higher signal:noise than more stringent lysis (see TABLE 2, below). Values in TABLE 2 are averaged across results from four different clinical pools of cervical specimens. Typically, these pools vary greatly in background.

TABLE 2

| Lysis Condition | Background (RLUs) 1 mL PC- pools | Background Variability | S/N Ratio ($10^4$ SiHa Cells) |
|---|---|---|---|
| Water | 71 | 21.8% | 6.6 |
| 100% Lysis Buffer | 652.3 | 53.2% | 4.7 |

Example 5

Hypotonic Lysis of Cell Pellets

FIG. 7 shows that hypotonic lysis of cell pellets ensures that background noise remains stable. Varying amounts of cervical specimens (250 ul-10 ml) were spun down, lysed with water, and subjected to RNA detection assays of the present disclosure. As shown in the graph in FIG. 7, the background does not change significantly regardless of the amount of specimen used.

Example 6

Limit of Detection

The limit of detection for HPV 16 E6/7 RNA from HPV positive cells (SiHa cells) was tested (see FIG. 8). Cells were spiked into 1 mL of a pool of negative cervical specimens to model a clinical sample. After spinning down and being lysed with water and heated, buffer was added to the cells (to a concentration of 32.5% buffer, or about 1M guanidine thiocyanate and about 0.7% detergent) and they were placed in a plate to begin the RNA detection assay of the present disclosure. The results show that using the methods of the present disclosure, as few as $1\times10^3$ cells are required for HPV E6/7 RNA detection.

Example 7

Lysing Cells Captured by COOH Beads

Figure 9:
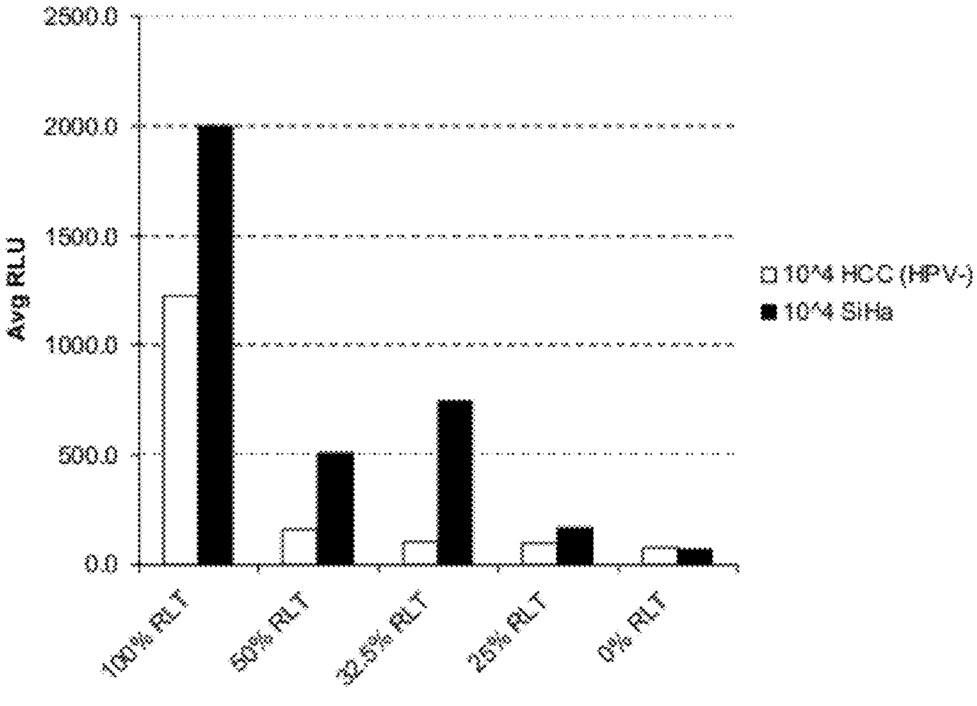
FIG. 9 shows results from tests of various lysis buffers for the ability to lyse cells captured by COOH beads. The data of FIG. 9, along with that of TABLE 1, below, shows the preferred lysis buffer is about 1M guanidine thiocyanate and about 0.7% detergent.

Various lysis buffers were compared for the ability to lyse cells captured by COOH beads (see FIG. 9). The results show that water alone is not enough to lyse cells captured by COOH beads. Either HPV negative or HPV positive cells were spiked into 1 mL of a negative cervical pool. After cells were captured by beads and the supernatant removed, varying concentrations of buffer (containing guanidine thiocyanate and detergent) were added to the samples which were then heated for 15 min at 65° C. Buffer concentration was adjusted to a total of 32.5% for RNA detection using methods of the present disclosure. As seen with the spin-down method, background does decrease with decreasing amounts of salt and detergent. However, at least 32.5% buffer (totaling approximately 1 M salt and 0.7% detergent) is required to lyse the cells enough to release RNA.

Example 8

Time Course of Cell Capture by COOH Beads Shows that Capture of Cells onto the Beads is a Biphasic Reaction A time course of cell capture by COOH beads was conducted (see FIG. 10). Cells were spiked into 1 mL of a negative cervical pool. The baseline number of cells was counted, and at each time point after addition of COOH beads, beads were pelleted for 1.5 min and then the supernatant removed and diluted for counting. Approximately 50% of cells are captured within a minute. Capture then plateaus but at 30 min at least 95% of the cells have been captured. More beads provide slightly more efficient capture.

Example 9

Carboxyl (COOH) Bead Capture is More Efficient than Hypotonic Lysis

HPV 18 positive (HeLa) cells in 1 mL of a pool of negative cervical specimens were prepared with either COOH bead capture or with pelleting and hypotonic lysis. The limit of detection for the carboxyl bead capture method is also approximately 1000 HPV positive cells and the results of the reverse hybrid capture assay show that this method is more efficient for obtaining mRNA from cells (see FIG. 11). While the background is slightly higher when COOH bead capture is used (271 RLUs versus 163 RLUs for hypotonic lysis), both signal:noise and signal—noise (a measure of the total RNA detected) were much higher than when hypotonic lysis is used.

Example 10

Pretreatment Procedure (Hypotonic Lysis) Combined with Detection of Target RNA

The following protocol combines a sample pretreatment procedure (using hypotonic cell lysis) with an RNA detection method of the present disclosure. Spin down cells in tubes for 3 minutes at 1500 relative centrifugal force (RCF). Supernatant was removed and 33.75 μL water was added and pipetted gently to resuspend the pellet. Then, heat for 15 minutes at 65° C. with gentle shaking Next, add 16.25 μL buffer (about 3 M guanidine thiocyanate and about 2% detergent) and transfer 50 μL sample to wells on the plate. Then, add 10 μL preconjugated streptavidin beads with biotinylated capture probes and incubate the plate for 30 minutes at 60° C. with shaking at 1150 revolutions per minute (RPM). Place the plate on a magnetic rack and let the beads pellet for 1.5 min and then decant and blot plate. Wash twice with Sharp Wash buffer (1 M Tris-HCl, 0.6 M NaCl, 0.25% Tween-20); the first wash should be 2 minutes and the second wash should be 5 minutes. After washing, decant and dry plate well by blotting. To each well, add 65 μL signal amplification probes diluted to 4.2 nM in RNA hybridization buffer. Then, incubate the plate for 30 minutes at 60° C. with shaking at 1150 RPM. Place the plate on magnetic rack for 3 min, decant, and dry wells. Add 35 μL Digene Hybrid Capture 2 kit Detection Reagent 1 (alkaline phosphatase-conjugated antibodies to RNA:DNA hybrids in buffered solution with 0.05% (w/v) of sodium azide, and with no RNase) into each well and incubate the plate for 30 minutes at 45° C. Place the plate on the magnetic rack, decant, and blot. Wash the plate five times with buffer comprising 40 mM Tris-HCl, 100 mM NaCl, 0.5% Triton X-100, allow plate to sit 1 minute per wash. Then, decant and dry the wells. Next, add 45 μL Digene Hybrid Capture 2 kit Detection Reagent 2 (CDP-Star® reagent with Emerald II™, a chemiluminescent substrate) to each well. Protect from light and incubate the plate for 15 minutes at room temperature with shaking at 300 RPM. Read the plate on a luminometer.

Example 11

Pretreatment Procedure (COOH Bead Capture) Combined with Detection of Target RNA The following protocol combines carboxyl bead capture sample preparation with an RNA detection method of the present disclosure. To each sample, add 8 μL carboxyl (COOH) beads (2 mL well plate) and shake at 800 RPM for 30 minutes at room temperature. Place the plate on a magnetic rack for 2 minutes to pellet beads. Remove supernatant with vacuum and resuspend in 50 μL 32.5% buffer (about 1M guanidine thiocyanate and about 0.7% detergent). Then, shake at 1000 RPM for 15 minutes at 65° C. Place the plate on a magnetic rack, pellet the beads, and transfer supernatant to new wells. Then, add 10 μL preconjugated streptavidin beads with biotinylated capture probes and incubate the plate for 30 minutes at 60° C. with shaking at 1150 RPM. Place the plate on a magnetic rack and let the beads pellet for 1.5 min and then decant and blot plate. Wash twice with Sharp Wash buffer (1 M Tris-HCl, 0.6 M NaCl, 0.25% Tween-20); the first wash should be 2 minutes and the second wash should be 5 minutes. After washing, decant and dry plate well by blotting. To each well, add 65 μL signal amplification probes diluted to 4.2 nM in RNA hybridization buffer. The, incubate the plate for 30 minutes at 60° C. with shaking at 1150 RPM. Place the plate on magnetic rack for 3 min, decant, and dry wells. Add 35 μL Detection Reagent 1 (alkaline phosphatase-conjugated antibodies to RNA: DNA hybrids in buffered solution with 0.05% (w/v) of sodium azide, and with no RNase) into each well and incubate the plate for 30 minutes at 45° C. Place the plate on the magnetic rack, decant, and blot. Wash the plate five times with buffer comprising 40 mM Tris-HCl, 100 mM NaCl, 0.5% Triton X-100, allow plate to sit 1 minute per wash. Then, decant and dry the wells. Next, add 45 μL Detection Reagent 2 (CDP-Star® reagent with Emerald II™, a chemiluminescent substrate) to each well. Protect from light and incubate the plate for 15 minutes at room temperature with shaking at 300 RPM. Read the plate on a luminometer.

Example 12

Streptavidin Bead-Biotinylated Probe Conjugation

The following protocol provides a method of forming DNA capture probes bound to magnetic beads. Vortex and sonicate Seradyn dsMag streptavidin beads (Seradyn part #3015210301050, Thermo Fisher Scientific, Inc.). Add 5 μL beads to 250 μL bead conjugation buffer (1×PBS; 0.15 M NaCl). Pull down beads on magnetic rack and was twice with bead conjugation wash buffer (above 0.5% Tween-20). Resuspend beads with 45 nM of each DNA capture probe in bead conjugation buffer. Incubate for 30 minutes at 37° C. with shaking at 1150 RPM. Pull down beads and wash three times with bead conjugation wash buffer. Resuspend in 250 μL Blocker buffer (casein-based) from Digene Hybrid Capture 2 to yield 50× beads.

Example 13

Reverse Hybrid Capture Assay

Reverse hybrid capture detects mRNA by first capturing the target RNA onto complementary biotinylated DNA probes that are conjugated to magnetic streptavidin beads. This probe-bead complex may be preconjugated and is stable at 4° C. for several months. This capture step requires 30 min and should occur at 60° C. with constant shaking. The beads with the captured target are then washed so that any non-target RNA sequences are removed. Because the hybrid capture antibody binds to individual DNA-RNA hybrids, it is preferable to cover the target RNA with DNA probes (e.g., DNA capture probe and amplification probes) to achieve the maximal signal (see, e.g., FIGS. 1 & 2). Thus, additional probes are then hybridized to the target mRNA. Because only the target is present at this point (because non-target RNA has been washed away), these probes need not be sequence-specific but rather may cover the full length of the gene, excluding regions that are already covered by the biotinylated DNA probes. These "signal amplification" probes are diluted to a working concentration of 4.2 nM. This hybridization also occurs at 60° C. for 30 min at a pH of around 7.8, preferably with shaking. The hybridization is then followed by detection with the hybrid capture antibody system: exposure to Detection Reagent 1 (alkaline phosphatase-conjugated antibodies to RNA:DNA hybrids in buffered solution with 0.05% (w/v) of sodium azide, and with no RNase) for 30 min at 45° followed by extensive washing and subsequent addition of Detection Reagent 2 (CDP-Start reagent with Emerald II™, a chemiluminescent substrate) for 15 min at room temperature. The signal is read on a luminometer. This post-analytic portion of the assay takes approximately 2 h 15 min.

Example 14

Effect of Adding Unlabeled Signal Amplification Probe

The signal is relatively low for a RNA target captured with only 3 or 5 biotinylated DNA capture probes and no unlabeled signal probes. The signal is substantially higher when unlabeled probes are hybridized to the target before detection with hybrid-capture antibody and luminescence technology. The reverse hybrid-capture assay is used to detect RNA. In this experiment, a variable number of biotinylated DNA capture probes were conjugated to streptavidin beads (see FIG. 4). The target was the E6/7 gene of HPV 16. The assay was performed with each set of beads with and without the addition of signal amplification probes (one- versus two-step assay, respectively). When no unlabeled DNA probes for signal amplification were added (one-step assay; gray bars), the signal increased with the amount of coverage provided by the biotinylated capture probes. However, when unlabeled DNA probes for signal amplification were added (two-step assay; black bars), the signal was much higher than in the one-step assay when only 1, 3, or 5 capture probes were used. In the two-step assay, optimal signal was achieved with as few as 3 to 5 capture probes.

Example 15

Length of mRNA Transcript Determined by Molecular Ruler Method

The length of HPV transcripts can be "measured" by capture onto magnetic beads and detection with unlabeled oligonucleotides used in order to extend the length of the hybrid region. Signal output will increase with successive addition of amplification signal probes until maximum length is reached, where the signal will plateau. The various HPV transcripts for HPV 16 are shown schematically in FIG. 12. The numbered regions 1 through 7 (FIG. 12) are designated for probe design. For instance, the E6/7 gene transcript can be captured from a sample using the DNA capture probe 3 and the combination of signal amplification probes will determine the signal output. If the variant form present is full length and the combination of amplification probes covers the entire length of the transcript, the signal will be strong. If E6/7 the variant form present is spliced and a subset of signal probes is used (e.g., probes 1 and 6), then the signal output will be somewhat weaker compared to signal from full-length/unspliced E6/7 (see TABLE 3). If the E6/7 variant form is spliced and integrated, it will provide a much weaker signal (see TABLE 3). The stronger signal is indicative of a greater number of targets and a certain disease state. E6/7 spliced integrated variant provides a weaker signal and is indicative of fewer targets captured, and thus less expression of this gene. It is also indicative of a different disease state. TABLE 3 shows the expected signal resulting from the combined use of the listed probes (shown in FIG. 12) from various regions of HPV 16.

TABLE 3

| mRNA Target | Splice Form | Capture Probes | Signal Probes | Signal Output |
|---|---|---|---|---|
| E6/7 | unspliced full length | 2 | 1, 2, 3, 4, 5, 6, 7 | ++++++ |
| | spliced | 3 | 1, 6 | ++++ |
| | spliced/integrated | 3 | 1, 6 | + |
| E2 | episomal | 5 | 1, 5, 6 | ++++++ |
| | integrated | 5 | 1, 5, 6 | + |
| L1 | spliced | 7 | 4, 6, 7 | ++++++ |

Referring again to FIG. 12 and TABLE 3, the signal contributed by non-spliced transcripts hybridizing to capture probe #2 (for example) may be subtracted from the signal generated using other capture probes to determine the degree of signal arising from spliced transcripts alone. The combination of signal amplification probes will determine the extent of coverage on the target mRNA and hence, signal output. Comparison of the signal output resulting from different combinations of amplification probes will indicate the presence of particular mRNA splice form variants. In this way, this method is a “molecular ruler” in that the signal output is dependent upon the splice form present and can indicate progression of disease state.

Example 16

Detection of Elevated Early:Late mRNA Ratio

Figure 14:
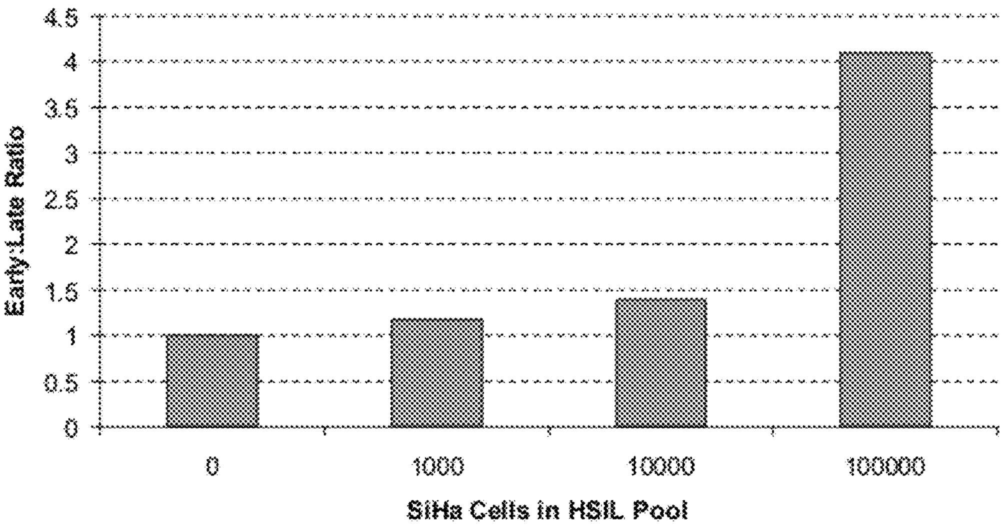
FIG. 14 shows that a fraction of cells with a high early:late HPV mRNA ratio may be detected against a background of cells with a low ratio. For this FIG. 14, SiHa cells (cervical cancer cell line) were added to a pool of cervical specimens (each diagnosed with a high-grade HPV-related lesion). The SiHa cells incorporate a high ratio of HPV early transcripts: HPV late transcripts, which is a common characteristic of cervical cancer. The sample mimicked a specimen that has cancer cells among pre-cancerous lesion cells. The results show that the invented assay will detect cancer cells in a pool of more benign lesion cells.

The methods of the present disclosure enable detection of a ratio of early and late HPV mRNA transcripts, which may be indicative of progressing HPV-related cervical disease. The described assay detected a high early:late mRNA ratio of SiHa cells (cancer cell line) against a background of HPV-positive specimens (FIG. 14). Capture and detection DNA probes were designed to detect early transcripts and late transcripts of HPV. These two assays were performed concurrently on the same samples, and the ratio of the resulting signals indicates the ratio of the early and late HPV transcripts. To mimic specimens comprising a few cancer cells mixed with cells of pre-cancerous lesion, pools of HSIL specimens (high-grade squamous intraepithelial lesion, per Bethesda System for cervical cytology) were spiked with known numbers of SiHa cells (as indicated along the x-axis), and then assayed via the methods of the present disclosure (see, e.g., EXAMPLE 12). As indicated by FIG. 14, a fraction of cells with a high E6/7 mRNA ratio may be detected against a background of cells with a low ratio.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing aspects are presented by way of example only; the scope of the present disclosure is to be limited only by the following claims.

Example 17

Use of Nucleic Acids According to the Present Application

Samples and Specimens

Cell lines of SiHa (HTB-35), CaSki (CRL-1550), HeLa (CCL-2) and HCC 1806 (CRL-2335) were obtained from ATCC (Manassas, Va.) and cultured by standard techniques. Residual cervical specimens in liquid-based cytology (LBC) medium (PreservCyt®, Hologics, Ma; 20 ml original volume) were obtained after routine testing from Cytology Services of Maryland. Specimen pools were composed of several of these specimens. These specimens were 5-8 months old and stored at room temperature before use. HPV genotyping of some clinical specimens was done according to Nazarenko et al (2008) to confirm single HPV 16 infection or to confirm the lack of HPV DNA.

RNA Target Isolation

The in vitro transcribed HPV 16 or HPV 18 RNAs for E6 (1-790 nt) and E2 (2755-3852 nt) regions were prepared with standard cloning techniques using HPV 16 (SEQ ID NO: 106) or HPV 18 (SEQ ID NO: 107) as a template. RNA was prepared from samples, cell lines and specimens using either the Rneasy® Plus Mini Kit, or QIAzol lysis reagent (QIAGEN, Valencia, Ca). For QIAzol RNA isolation, the cells preserved in LBC were isolated by centrifugation, the cells were extracted and the precipitated RNA was then resuspended in tris-buffer (pH 7).

Cell Concentration

Some cells preserved in LBC medium (1 ml) from specimens were concentrated in microfuge tubes by adsorption onto carboxyl-modified magnetic beads (8 μl of 5% solids; catalog #65162105050350, Seradyn). The specimen-bead suspension was incubated at 22° C. for 30 min in a rotating microfuge block (1100 rpm, Eppendorf). The cells adsorbed onto beads were pelleted by a magnetic tube holder (Promega, Madison, Wis.). The percent of cells pelleted from mixtures of known cell number was determined by counting the cells in the leftover supernatant using a hemocytometer. The cells were washed with saline and resuspended in lysis buffer then transferred to a 96-well assay plate.

Oligodeoxyribonucleotides

The oligodeoxyribonucleotide (oligo) probes were designed to be specific for HPV 16 (or 18) mRNA targets by using either Blast (NCBI) comparisons. The design of capture probes was adjusted to avoid cross-hybridization with other HPV types. The signal amplification oligos were complimentary to their targets, but not designed to avoid cross-reactivity with other HPV types. Capture and amplification probe sequences are shown below in Table 4. Capture oligos were modified with a 5' biotin.

TABLE 4

| Target | Type | SEQ ID NO: | 5'-3' Sequence |
|---|---|---|---|
| HPV 16 E6-7 | Capture | 1 | GTTTGCAGCTCTGTGCATAACTGTGGTAACTTTCT |
| HPV 16 E6-7 | Capture | 2 | CAGTAACTGTTGCTTGCAGTACACACATTCTAATA |
| HPV 16 E6-7 | Capture | 3 | ACATATATTCATGCAATGTAGGTGTATCTCCATGC |
| HPV 16 E6-7 | Capture | 4 | AAGGTTACAATATTGTAATGGGCTCTGTCCGGTTC |
| HPV 16 E6-7 | Capture | 5 | ATTAACAGGTCTTCCAAAGTACGAATGTCTACGTG |
| HPV 16 E2 | Capture | 6 | CAATAGTCTATATGGTCACGTAGGTCTGTACTATC |
| HPV 16 E2 | Capture | 7 | CAAGGCTAACGTCTTGTAATGTCCACTTTTCATTA |
| HPV 16 E2 | Capture | 8 | TATAAACCATAATAGTCAACTTGACCCTCTACCAC |
| HPV 16 E2 | Capture | 9 | TTGGTCACGTTGCCATTCACTATCATATGTAAGTG |
| HPV 16 E2 | Capture | 10 | CTGATCTTGGTCGCTGGATAGTCGTCTGTGTTTCT |
| HPV 18 E6-7 | Capture | 11 | TCATAGTGGTCTATGATTTTGTCCTGCACGCAACT |
| HPV 18 E6-7 | Capture | 12 | TCCAATCCTCGGTTTTGTATCGACTTTGTGCAAGG |
| HPV 18 E6-7 | Capture | 13 | TGTGACTTACACAGGTAGCGGTTTTGTCCCATGTT |
| HPV 18 E6-7 | Capture | 14 | TGGGTTGACAGGTCCACAATGCTGCTTCTCCGCGA |
| HPV 18 E6-7 | Capture | 15 | CCACCAATATTTGTACACTATCTGGAATTGCAACA |
| HPV 18 E2 | Capture | 16 | ATACACAGGTTATTTCTATGTCTTGCAGTGAAGTG |
| HPV 18 E2 | Capture | 17 | GCACTGGCCTCTATAGTGCCCAGCTATGTTGTGAA |
| HPV 18 E2 | Capture | 18 | CATAGAAGGTCAACCGGAATTTCATTTTGGGGCTC |
| HPV 18 E2 | Capture | 19 | CGGGCTGGTAAATGTTGATGATTAACTCCATCTAT |
| HPV 18 E2 | Capture | 20 | CAGGGTGTTCAGAAACAGCTGCTGGAATGCTCGAA |
| HPV 16 E2 | Amplification | 21 | TTTTATACATCCTGTTGGTGCAGTTAAATACACTT |
| HPV 16 E2 | Amplification | 22 | CCATCAAACTGCACTTCCACTGTATATCCATGTTT |
| HPV 16 E2 | Amplification | 23 | TCCAGTTTGTATAATGCATTGTATTGCATATGTCT |
| HPV 16 E2 | Amplification | 24 | AGTTACTGATGCTTCTTCACAAATATATATATGTG |
| HPV 16 E2 | Amplification | 25 | CTTTATTTTTACTATATTTTTCTGCATCATCTTTAAA |

TABLE 4-continued

| Target | Type | SEQ ID NO: | 5'-3' Sequence |
|---|---|---|---|
| HPV 16 E2 | Amplification | 26 | CATAATATTACCTGACCACCCGCATGAACTTCCCATA |
| HPV 16 E2 | Amplification | 27 | AGAGGATACTTCGTTGCTGCTAAACACAGATGTAGGA |
| HPV 16 E2 | Amplification | 28 | CGGGGTGGTTGGCCAAGTGCTGCCTAATAATTTCAGG |
| HPV 16 E2 | Amplification | 29 | CTGCACAAAATATGTTCGTATTCCTTCATGAACATAA |
| HPV 16 E2 | Amplification | 30 | TCGGTGCCCAAGGCGACGGCTTTGGTATGGGTCGCGG |
| HPV 16 E2 | Amplification | 31 | CACACATTTAAACGTTGGCAAAGAGTCTCCAT |
| HPV 16 E2 | Amplification | 32 | ATTTTCATAATGTGTTAGTATTTTGTCCTGA |
| HPV 16 E2 | Amplification | 33 | TAGTTTTTGGTATTTTAACTTGAGACAAAAA |
| HPV 16 E2 | Amplification | 34 | TCATATAGACATAAATCCAGTAGACACTGTAA |
| HPV 16 E2 | Amplification | 35 | TAATAAATAGCACATTCTAGGCGCATGTGTTTC |
| HPV 16 E2 | Amplification | 36 | TTAATATGTTTAAATCCCATTTCTCTGGCCTTG |
| HPV 16 E2 | Amplification | 37 | TTTGATACAGCCAGTGTTGGCACCACTTGGTGG |
| HPV 16 E2 | Amplification | 38 | AGTTGCAGTTCAATTGCTTGTAATGCTTTATTC |
| HPV 16 E2 | Amplification | 39 | CTATATTGTGAGTTATATATTGTTTCTAACGTT |
| HPV 16 E2 | Amplification | 40 | TAGTGGTGTGGCAGGGGTTTCCGGTGTCTGGCT |
| HPV 16 E2 | Amplification | 41 | TAACAATTGCACTTTTATGTTTTACATTATGTC |
| HPV 16 E2 | Amplification | 42 | GGAGCACTGTCCACTGAGTCTCTGTGCAACAACT |
| HPV 16 E2 | Amplification | 43 | TCCTTTGTGTGAGCTGTTAAATGCAGTGAGGATT |
| HPV 16 E2 | Amplification | 44 | CTATGGGTGTAGTGTTACTATTACAGTTAATCCG |
| HPV 16 E2 | Amplification | 45 | CATTTTAAAGTATTAGCATCACCTTTTAAATGTA |
| HPV 16 E2 | Amplification | 46 | CAATGTACAATGCTTTTTAAATCTATATCTTAAA |
| HPV 16 E2 | Amplification | 47 | CTGTCCAATGCCATGTAGACGACACTGCAGTATA |
| HPV 16 E6-7 | Amplification | 48 | ATACTATGCATAAATCCCGAAAAGCAAAGTCATATAC |
| HPV 16 E6-7 | Amplification | 49 | ATTTATCACATACAGCATATGGATTCCCATCTCTAT |
| HPV 16 E6-7 | Amplification | 50 | GTCTATACTCACTAATTTTAGAATAAAACTTTAAAC |

TABLE 4-continued

| Target | Type | SEQ ID NO: | 5'-3' Sequence |
|---|---|---|---|
| HPV 16 E6-7 | Amplification | 51 | GTTCTAATGTTGTTCCATACAAACTATAACAATAAT |
| HPV 16 E6-7 | Amplification | 52 | CTAATTAACAAATCACACAACGGTTTGTTGTATTGCT |
| HPV 16 E6-7 | Amplification | 53 | CCTGTGGGTCCTGAAACATTGCAGTTCTCTTTTGGTGCAT |
| HPV 16 E6-7 | Amplification | 54 | TGTGCTTTGTACGCACAACCGAAGCGTAGAGTCACACTTG |
| HPV 16 E6-7 | Amplification | 55 | TTATGGTTTCTGAGAACAGATGGGGCACACAATTCCTAGT |
| HPV 16 E6-7 | Amplification | 56 | TTTTCTTCAGGACACAGTGGCTTTTGACAGTTAATACAC |
| HPV 16 E6-7 | Amplification | 57 | ATATTATGGAATCTTTGCTTTTTGTCCAGATGTCTTTGC |
| HPV 16 E6-7 | Amplification | 58 | CTGCAACAAGACATACATCGACCGGTCCACCGACCCCTT |
| HPV 16 E6-7 | Amplification | 59 | ATGATTACAGCTGGGTTTCTCTACGTGTTCTTGATGAT |
| HPV 16 E6-7 | Amplification | 60 | CTCCTCTGAGCTGTCATTTAATTGCTCATAAC |
| HPV 16 E6-7 | Amplification | 61 | AGTAGAGATCAGTTGTCTCTGGTTGCAAATCTA |
| HPV 16 E6-7 | Amplification | 62 | TGCTTGTCCAGCTGGACCATCTATTTCATCCTC |
| HPV 18 E2 | Amplification | 63 | TAAACGTTCCGAAAGGGTTTCCTTCGGTGTCTGCAT |
| HPV 18 E2 | Amplification | 64 | ATACTGTATTTGGCTGTCTATGTCTTTACTGTCATTT |
| HPV 18 E2 | Amplification | 65 | AAAGAATATTGCATTTTCCCAACGTATTAGTTGCCA |
| HPV 18 E2 | Amplification | 66 | GGTGGTTTAATGTCTGTATGCCATGTTCCCTTGCTGC |
| HPV 18 E2 | Amplification | 67 | CTTTACTTTTTGAAATGTTATAGGCTGGCACCACCT |
| HPV 18 E2 | Amplification | 68 | CCTTGTAGGGCCATTTGCAGTTCAATAGCTTTATGTG |
| HPV 18 E2 | Amplification | 69 | GTTCTGTATTCCATAGTTCCTCGCATGTGTCTTGCAGTG |
| HPV 18 E2 | Amplification | 70 | TTGTACTGTTTGGCCACCTTTTTTAAAGCAGTGAGTAG |
| HPV 18 E2 | Amplification | 71 | TAGGTCATACAATTGTCTTTGTTGCCATCAAAATATAC |
| HPV 18 E2 | Amplification | 72 | CCTGCATCAGTCATATAATACACACTGTCCCATGCTACA |
| HPV 18 E2 | Amplification | 73 | ACGTGTTGTACCCTTCCTTTACATAATACAATCCCC |
| HPV 18 E2 | Amplification | 74 | ATATTTTTCACATTCACTTTTAAATTCTATATAAA |
| HPV 18 E2 | Amplification | 75 | TTCCCAAAATGTACTTCCCACGTACCTGTGTTCCC |

TABLE 4-continued

| Target | Type | SEQ ID NO: | 5'-3' Sequence |
|---|---|---|---|
| HPV 18 E2 | Amplification | 76 | TACTGCACATAGAGTCATTACAATCAATTACATTA |
| HPV 18 E2 | Amplification | 77 | AACAAGCTGAGTAGCGGATACCGTGTCGTCACTGG |
| HPV 18 E2 | Amplification | 78 | CTGGAATACGGTGAGGGGGTGTGCTGTAGCTGTTT |
| HPV 18 E2 | Amplification | 79 | GGCCGTAGGTCTTTGCGGTGCCCACGGACACGGTG |
| HPV 18 E2 | Amplification | 80 | GTCCACAGTGTCCAGGTCGTGTAGCAGCCGACGTCT |
| HPV 18 E2 | Amplification | 81 | TTTGTTGTTGCCTGTAGGTGTAGCTGCACCGAGAAG |
| HPV 18 E2 | Amplification | 82 | TATAGGCGTAGTGTTACCACTACAGAGTTTCCGTCT |
| HPV 18 E2 | Amplification | 83 | ACATTTTAAACTGTTTCTGTCACCTTTTAAATGTAT |
| HPV 18 E2 | Amplification | 84 | TAGTGGTCGCTATGTTTTCGCAATCTGTACCGTAA |
| HPV 18 E2 | Amplification | 85 | GCACCTGTCCAATGCCAGGTGGATGATATATCTCTA |
| HPV 18 E2 | Amplification | 86 | TATGTTACAGTCAGTATTCCTGTTTTTTCATTGCCT |
| HPV 18 E2 | Amplification | 87 | GTATTTAAAAATTTTGTTCTTTGTGTTTCACTATGG |
| HPV 18 E6-7 | Amplification | 88 | GGGTCGCCGTGTTGGATCCTCAAAGCGCGCCAT |
| HPV 18 E6-7 | Amplification | 89 | TTCAGTTCCGTGCACAGATCAGGTAGCTTGTA |
| HPV 18 E6-7 | Amplification | 90 | TCTGTAAGTTCCAATACTGTCTTGCAAT |
| HPV 18 E6-7 | Amplification | 91 | CACCACAAATAAATCTTTAAATGCAAATTCAAATACC |
| HPV 18 E6-7 | Amplification | 92 | ATTTATGGCATGCAGCATGGGGTATACTGTCTCTATA |
| HPV 18 E6-7 | Amplification | 93 | GTCTTAATTCTCTAATTCTAGAATAAAAATCTATAC |
| HPV 18 E6-7 | Amplification | 94 | TTTTCCAATGTGTCTCCATACACAGAGTCTGAATAAT |
| HPV 18 E6-7 | Amplification | 95 | CCTTATTAATAAATTGTATAACCCAGTGTTAGTTAGT |
| HPV 18 E6-7 | Amplification | 96 | TGCTGGATTCAACGGTTTCTGGCACCGCAGGCA |
| HPV 18 E6-7 | Amplification | 97 | ATCGTCGTTTTTCATTAAGGTGTCTAAGTTTTTC |
| HPV 18 E6-7 | Amplification | 98 | TTGGAGTCGTTCCTGTCGTGCTCGGTTGCAGCACGAATG |
| HPV 18 E6-7 | Amplification | 99 | ATGCATACTTAATATTATACTTGTGTTTCTCTGCGTCG |
| HPV 18 E6-7 | Amplification | 100 | TAAATGCAATACAATGTCTTGCAATGTTGCCTTAGGTCC |

TABLE 4-continued

| Target | Type | SEQ ID NO: | 5'-3' Sequence |
|---|---|---|---|
| HPV 18 E6-7 | Amplification | 101 | TTCATCGTTTTCTTCCTCTGAGTCGCTTAATTGCTCGTGA |
| HPV 18 E6-7 | Amplification | 102 | CAACATTGTGTGACGTTGTGGTTCGGCTCGT |
| HPV 18 E6-7 | Amplification | 103 | AATTCTGGCTTCACACTTACAACACATACA |
| HPV 18 E6-7 | Amplification | 104 | GGTCGTCTGCTGAGCTTTCTACTACTAGCTC |
| HPV 18 E6-7 | Amplification | 105 | TTACTGCTGGGATGCACACCACGGACACACAAAGGA |

The reverse-transcription, PCR primers and TaqMan probes were designed by PrimerQuest (IDT, Coralville, Iowa) and Beacon Designer (Palo Alto, Calif.). All oligonucleotides were synthesized by IDT (Coralville, Iowa).

Realtime, Reverse-Transcription and PCR (RT-PCR)

One-step RT-PCR was performed using the QuantiTect® 5× Virus Mix (no rox; QIAGEN, Valencia, Calif.), according to vendor protocol. Primer and probe sets were designed for the E6-7 region and the E2 region using software. Realtime, RT-PCR was performed using either a Stratagene MX3000P (Stratagene, LaJolla, Calif.) or Bio-Rad iQ™5 (Bio-Rad, Hercules, Calif.) realtime PCR instrument. RT-PCR volumes were 25 µl. Consensus PCR (Nazarenko et al., 2008) was used to indicate whether a cervical specimen pool contained HPV DNA types.

Hybrid Capture Assay

The RNA isolation occurred in 60 µl of lysis buffer (RLT Plus, QIAGEN Inc) with the addition of 10 µl of magnetic beads (streptavidin-modified, 0.01% solids, 1 µl, Seradyn). Biotinylated, capture oligos were coupled to the magnetic beads using standard procedures. There were five sequence-specific capture probes per target. The target RNA was captured onto these oligo-modified beads during incubation at 60° C. for 30 min with 1100 rpm rotation. This sample was diluted 1:3 with pure water and split into two wells of a 96-well microtiter plate. Amplification DNA probes (4.2 mM each, 33-45 nt) were hybridized to the target RNA in a buffer composed of a 5:8 mixture of Denaturation Reagent: Probe Diluent (QIAGEN Inc). There were 15 amplification probes for the E6-7 target and 27 amplification probes for the E2 target. The resulting hybrids affixed to beads were pelleted using a magnetic plate holder (Ambion). The hybrid-bead complex was washed on the magnetic plate with a saline, detergent-based buffer (pH 7.5). The complex was incubated (45° C., 30 min) with monoclonal Hybrid Capture antibodies conjugated to alkaline phosphatase (DR1; QIAGEN Inc). This complex was then washed with HC2 wash buffer (QIAGEN Inc). The complex was then incubated (22° C., 15 min, rotation 300 rpm) with a chemiluminescent, alkaline phosphatase substrate (DR2, QIAGEN Inc). The signal was measured in relative luminescence units (RLU) using a DML 2000 luminometer (QIAGEN Inc).

Results

Stability of HPV mRNA

Figure 15:
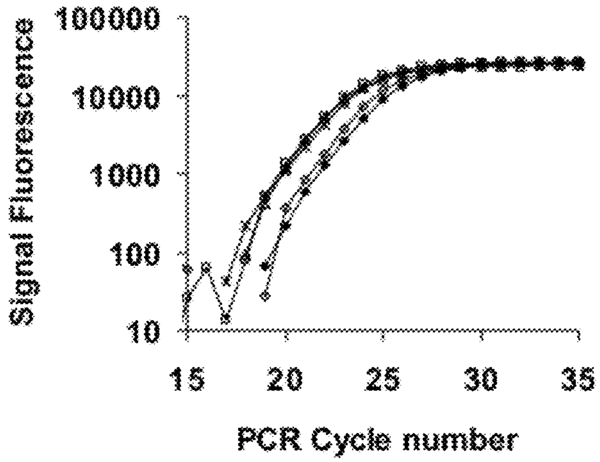
FIG. 15 shows HPV RNA stability of SiHa cells preserved in a LBC clinical specimen pool. The RT-PCR plots show the assay signal (y-axis) plotted against PCR cycle number (x-axis) for samples of SiHa cells incubated over the course of 67 days. Symbols are star, 3 days; square, 13 days; triangle, 26 days; filled diamond, 42 days; open diamond, 67 days. Values are an average of two reactions for each day.

The stability of the HPV mRNA in cells that were fixed in LBC medium was determined using a realtime, RT-PCR assay. SiHa cells contain 2 copies of integrated HPV 16 genome (no episomal) and express HPV E6-7 mRNA. Fresh SiHa cells were preserved in pooled LBC cervical specimens that previously contained no HPV as indicated by PCR. These samples were incubated at room temperature for up to 67 days. Two aliquots (1 ml) were removed periodically (3, 13, 26, 42 and 67 days) and the RNA was isolated by QIAzol reagent. The HPV mRNA level was determined using a realtime, RT-PCR (5'-3'; Forward primer GCACCAAAAGAGAACTGCAATGT (SEQ ID NO: 108), reverse primer CATATACCTCACGTCGCAGTAACT (SEQ ID NO: 109), TaqMan probe FAM-CAGGACCCACAGGAGCGACCCAGA-BHQ1 (SEQ ID NO: 110)). Each reaction contained the mRNA from approximately 125,000 SiHa cells. The cycle threshold, a measure of mRNA abundance, of the RT-PCRs was relatively stable up to 42 days and then shifted by approximately 1-2 cycles for the 42 and 67 day aliquots (FIG. 15). This shift may account for a reduction in target mRNA of approximately 3-fold based on theoretical PCR kinetics.

Analytical Performance of the Hybrid Capture mRNA Detection Assay

Figure 16:
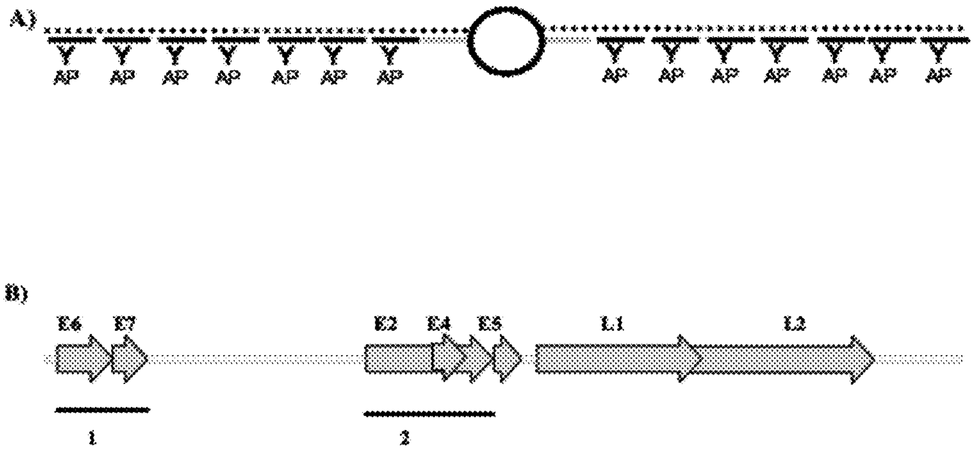
FIG. 16*a* shows a general scheme for hybrid capture detection of HPV mRNA. HPV mRNA target (dotted line) is annealed to capture oligos (short grey bars) that are coupled to a magnetic bead (circle). The RNA target is annealed with signal amplification oligos (short black bars) to create a longer hybrid. The RNA:DNA hybrid is bound with a hybrid capture antibody conjugated with alkaline phosphatase (Y-shaped AP symbol). A chemiluminescent substrate (not shown) is added to detect the complex in a luminometer.
FIG. 16*b* shows a schematic of the HPV genome structure with labeled genes (large grey arrows). The loci for E6-7 probes (1) or E2 probes (2) are shown by black bars underneath. The arrangement of genes and the loci for DNA probes are similar for HPV 16 and HPV 18, but the primary sequences are unique.

A schematic diagram for the hybrid-capture assay for mRNA is shown in FIG. 16*a*. The assay is loosely based on the digene HC2 HPV DNA Test® (QIAGEN Inc), except mRNA is the target and the probes consist of synthetic DNA (not RNA), the alkali denaturation of target is not included, and the formed RNA:DNA hybrids are captured on magnetic beads instead of an ELISA plate. Four hybrid capture assays for HPV mRNAs were designed to be specific to either HPV 16 E6-7 or E2, or HPV 18 E6-7 or E2, by using specific capture probes (Table 4). The specificity of the capture probes was confirmed by the Blast program. Cell pellets or RNA were lysed to release and unwind the RNA. The lysate was split equally into separate wells for detection of either E6-7 or E2 mRNA. Each well received a unique set of sequence-specific, capture probes (five, 35 nt) affixed to magnetic beads. After washing un-bound material, some amplification probes (33-45 nt) were added to complement the entire length of the E6-7 or E2 coding region for each captured mRNA target. These amplification probes were not designed to avoid cross-reactivity with other HPV types. Their function was to provide signal amplification via increased binding of hybrid capture antibody with alkaline phosphatase. The lengths of the formed hybrid targets were approximately 740 bp for the E6-7 and 1500 bp for the E2. The probe loci for hybrid capture probes are indicated in FIG. 16*b*.

Figure 17A:
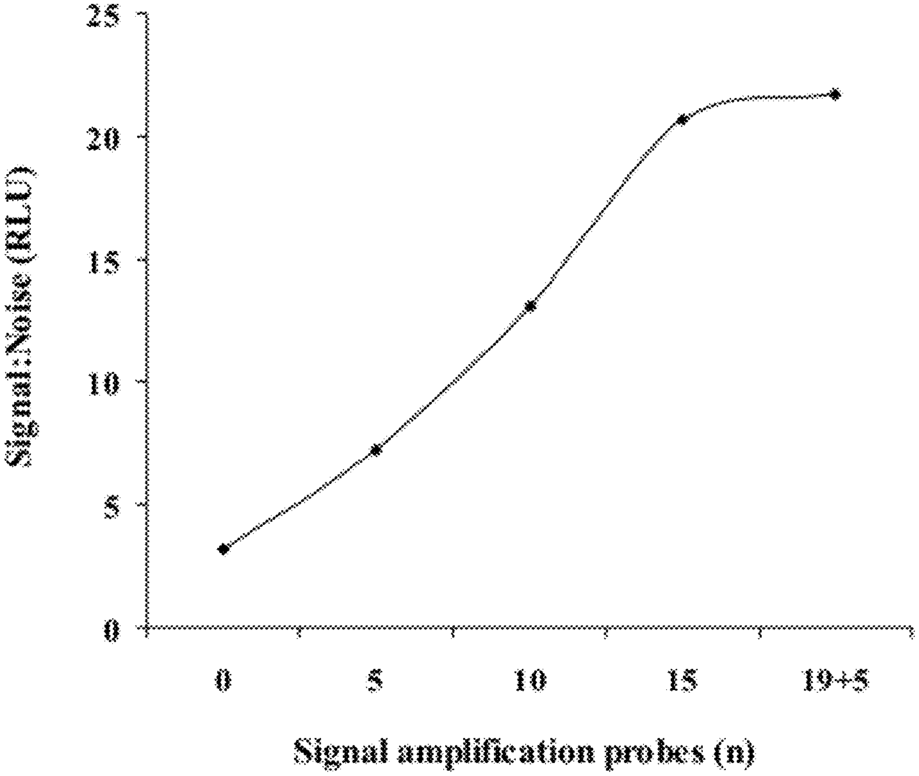
FIG. 17*a* shows the dependence of luminescence signal output (average RLU, n=4) on the number of complementary signal amplification probes per assay for the same target input ($1\times10^5$ copies, HPV 16 E6-7 in vitro transcribed RNA). In this experiment, the hybrid length increased in wells with the addition of 5, 10 and 15 probes. The signal did not increase for the well (labeled 5+15) with 5 non-complementary probes added to 15 complementary probes.
Figure 17B:
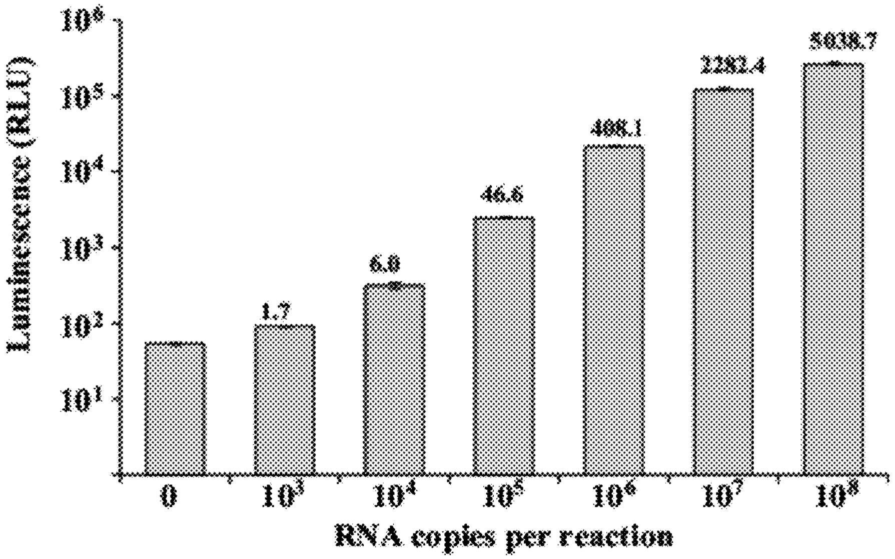
FIG. 17*b* shows the dependence of luminescence signal output (average RLU, n=3 samples, error bars show standard deviation) on target input (RNA copies per reaction) for a hybrid capture assay. Signal:noise ratio is given above bars.

The hybrid capture assay was first performed for pure, in vitro transcribed HPV RNA targets for HPV 16 E6-7, HPV 16 E2, HPV 18 E6-7 or HPV18 E2. The results for the HPV 16 E6-7 assay are shown in FIG. 17*b*. The assay detected approximately 1000 copies of RNA per reaction. There was a linear dependence of signal on target input with a dynamic range of 3-4 logs. A similar dependence of signal on target input was detected for the other three RNA targets including HPV 16 E2, HPV 18 E6-7, and HPV 18 E2 transcripts. No signal above background resulted when an HPV 18 RNA target was probed with the HPV 16 specific probes, or visa versa.

In addition to the amount of target, the assay signal depended on length of formed hybrid allowing the assay to be used as a molecular ruler. To demonstrate this, the relative length of the HPV 16 E6-7 in vitro transcribed RNA was measured by the dependence of the signal on the number of adjacent amplification probes used to lengthen the hybrids. Equivalent amounts of HPV 16 E6-7 RNA were captured by magnetic beads (five capture oligos) in several wells. An increasing number of adjacent amplification probe types were added to each separate well. Thus, each well had RNA: DNA hybrids of successively longer length, until some wells contained completely hybridized RNA targets (FIG. 17*a*). The signals for wells increased until a plateau was reached at the well in which the target was completely hybridized (15 amplification probes added). The further addition of five, non-complementary probes did not increase the assay signal.

Figure 18A:
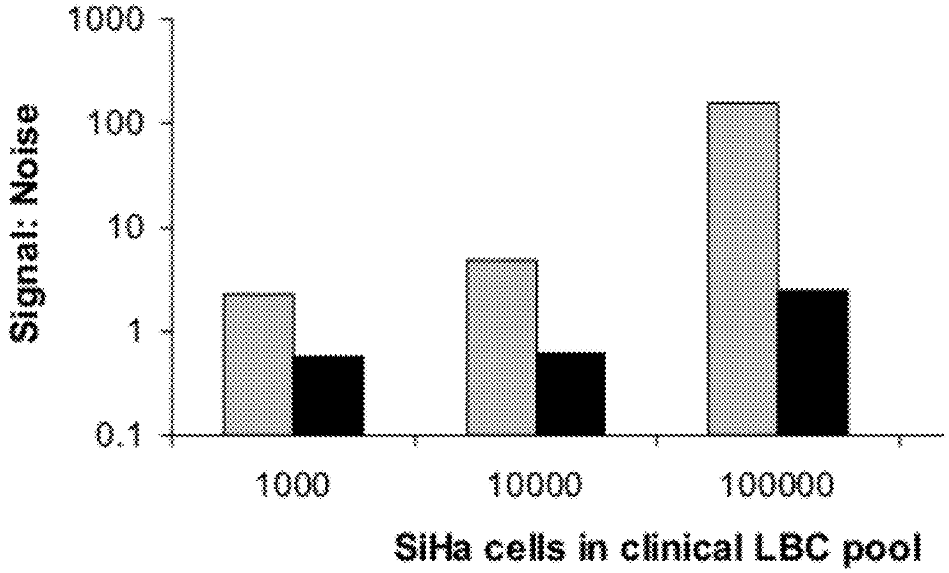
FIG. 18*a* shows the dependence of signal:noise (average, n=3) on number of SiHa cells per assay was plotted for the HPV 16 E6-7 (grey bars) and E2 (black bars); for the two assays in separate wells. For these assays, the background noise was obtained from the signal from a control assay with no target added, approximately 50 RLU.
Figure 18B:
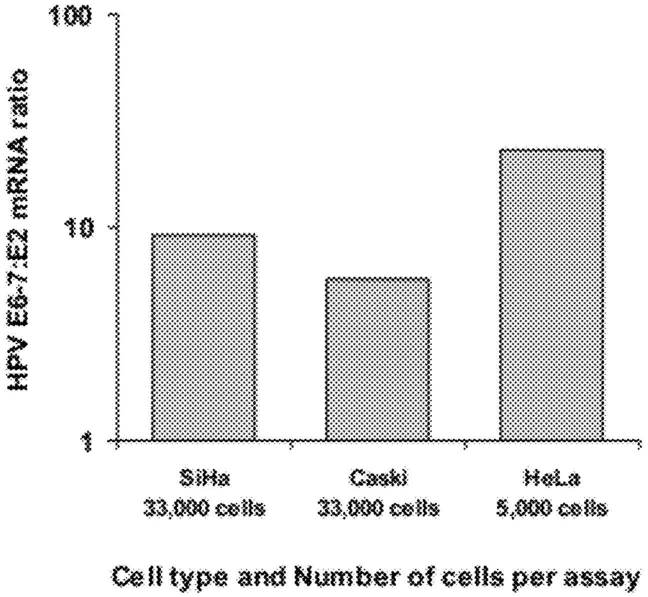
FIG. 18*b* shows the signal: noise values for HPV E6-7 and E2 mRNA assays were plotted as a ratio for the cancer cell lines, SiHa, Caski and HeLa; bars represent the average ratios of three replicate experiments.

The hybrid capture assay detected the HPV 16 mRNA of SiHa cells preserved in a pool of LBC clinical specimens which previously did not contain HPV. The cell concentration procedure using magnetic, carboxyl-coated beads was applied to pellet the SiHa and other cells, as described in methods. Ninety-five percent of the cells were pelleted in 30 min using this procedure; as determined by cell counting with a hemocytometer. The resulting cell pellets were lysed and the lysate was divided equally (by volume) into two wells. HPV 16 E6-7 transcripts were assayed in one well and HPV 16 E2 were assayed in a second well. The SiHa mixture expressed abundant E6-7 transcripts, but not E2 (FIG. 18*a*). These assays for HPV 16 detected only a negligible signal when HPV 18 mRNA of HeLa cells ($1\times10^6$ cells) was used as a target (S:N<2; not shown). Cross-reactivity with other HPV types was not tested. The ratio of HPV 16 E6-7 and E2 in SiHa cells may be calculated from this data. The maximum signal for the E2 hybrid was proportionally greater than for E6-7 hybrid due to its increased length. For this reason the E2 signal was divided by a factor of 0.51 when calculating E6-7:E2 ratios for cells and specimens. The HPV 16 E6-7:E2 ratio was 8.2 or higher for SiHa cells depending upon the number of cells in the assay. This method was used to calculate the HPV E6-7:E2 ratio for other cancer cell lines that express HPV transcripts. These include Caski and HeLa, which express HPV 16 and HPV 18, respectively (FIG. 18*b*). The ratio for the SiHa and HeLa cell lines was relatively higher than for Caski cells.

Figure 19:
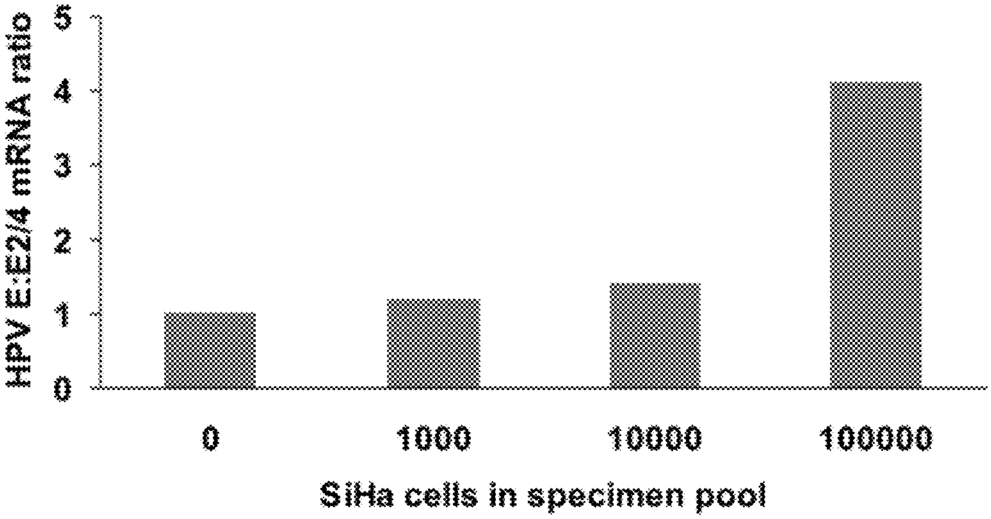
FIG. 19 shows detection of the HPV 16 E6-7:E2 transcript ratio in a mixture of SiHa cells with the cells from a pool of HPV-positive specimens. Cultured SiHa cells were mixed with a pool (2 ml) of HPV-positive, liquid-based cytology specimens (approximately 100,000 total cells in 2 ml).

Experiments were performed to determine the HPV E6-7: E2 ratios in heterogeneous mixtures of cancer cells and non-cancer cells that both express HPV E6-7 and E2 transcripts in un-equal ratios. The SiHa cells, which have a relatively high E6-7:E2 transcript ratio, were added and preserved in a pool of clinical specimens (LBC medium) that was positive for only HPV 16. The HPV 16 E6:E2 ratio of the pooled specimens was approximately 1, with no added SiHa cells. Serial dilutions of SiHa cells were added to 2 ml aliquots of this specimen pool. The sample RNA was isolated by QIAzol extraction. The results of the HPV E6-7 and E2 assays were expressed as a ratio (FIG. 19). The addition of SiHa cells to the HPV-positive pool resulted in an increased E6-7:E2 ratio, with a substantial increase of approximately 4.2-fold upon addition of 100,000 SiHa cells. In comparison, the ratio for SiHa cells alone (33,000 cells) was about 9 (FIG. 18*b*).

Figure 20:
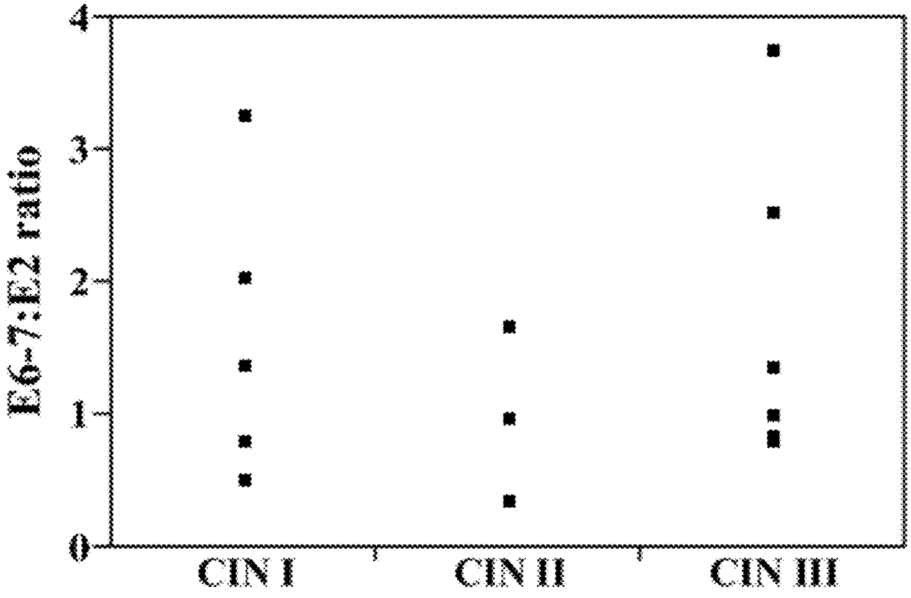
FIG. 20 shows the HPV 16 E6-7:E2 ratio in cervical specimens. The E6-7:E2 ratio was plotted from the hybrid capture assay results.
Figure 21:
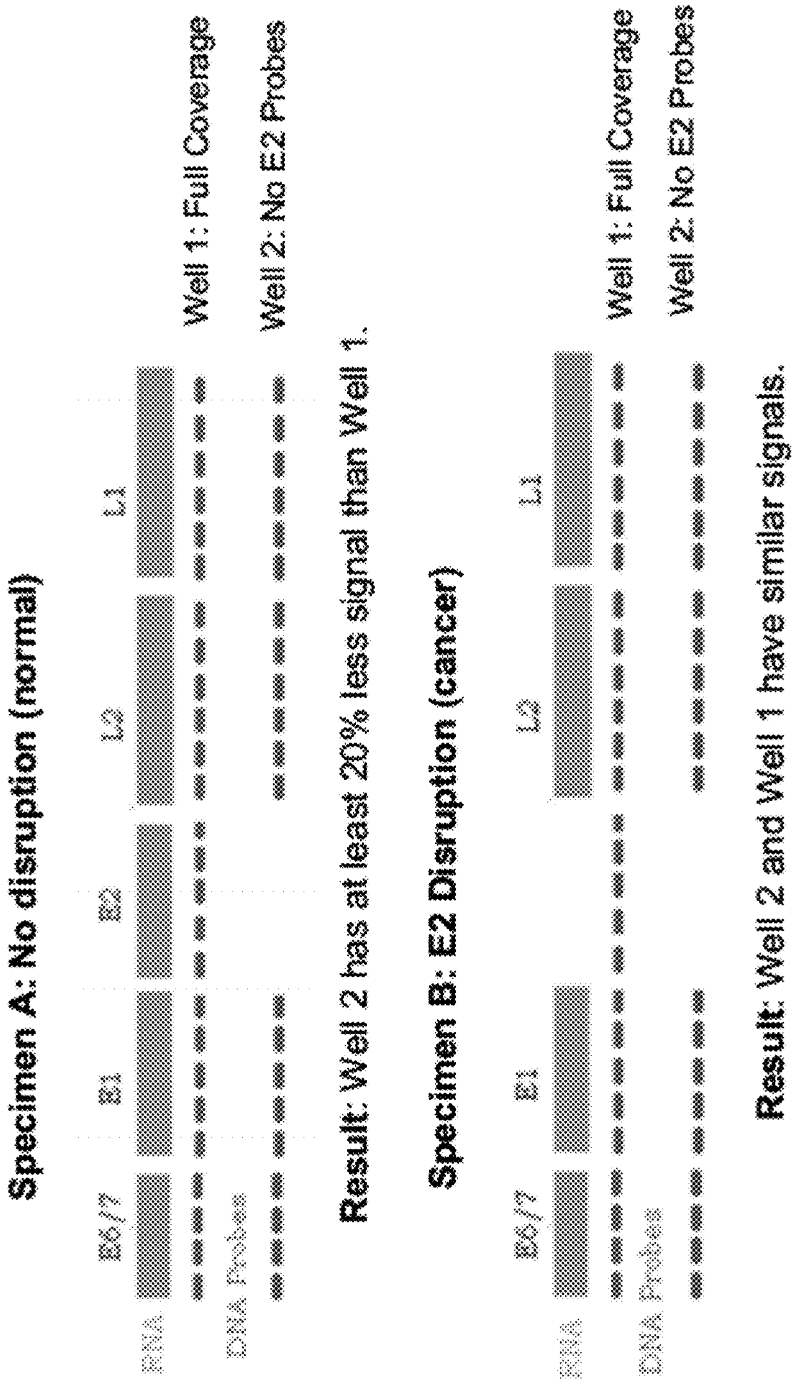
FIG. 21 illustrates a method for determining whether or not E2 gene expression is absent or disrupted.

The HPV 16 E6-7:E2 ratio was determined also in a limited number (n=13) of cervical specimens using the hybrid capture assay for HPV 16 E6-7 and E2. The histological diagnoses of the specimens were known and all specimens were confirmed by PCR to include only HPV 16. The specimen RNA was isolated by QIAzol extraction. There was a broad distribution of ratios for all histological grades, but some specimens had a relatively high ratio (FIG. 20).

This hybrid capture assay detected in vitro transcribed RNA with good linearity and dynamic range of approximately 3-4 logs. This analytical performance is similar to that of hybrid capture detection of DNA. There was no cross-reactivity between the HPV 16 and HPV 18 mRNA due to the specificity of the capture oligos. The cross-reactivity of all the various HPV types was not tested. Detection of E6-7 or E2 mRNA from either HPV 16 or HPV 18 was demonstrated by assays in separate wells. HPV E6-7:E2 ratios may be calculated from these separate assays. The use of short DNA probes for target capture and detection allow flexibility for design with various targets. The assays may be designed to detect a single HPV type (typing) in a single well or to detect simultaneously multiple, specific HPV sequences of various types (screening).

Example 18

Method for Determining the Presence or Absence of a Target Nucleic Acid

Figure 2:
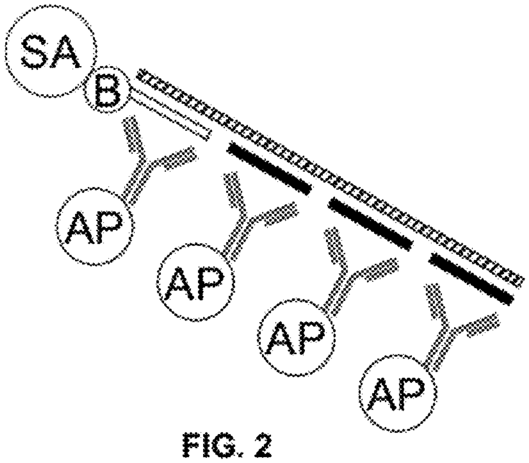
FIG. 2 is a diagram depicting the use of DNA capture probe (white bar), multiple DNA amplification probes (black bars), and multiple DNA:RNA hybrid antibodies to "amplify" the signal without the need for amplification of the target RNA (crosshatched bar). "B" represents a biotin moiety; "SA" represents a streptavidin moiety, B and SA may be replaced with other conjugation technology in which DNA probes are conjugated to the bead; "AP" represents alkaline phosphatase conjugated to an antibody, but AP could be any other appropriate detectable moiety (e.g., horseradish peroxidase, etc.).

Examples 18-21 utilize a two hybridization step assay as exemplified in FIG. 2. In the first hybridization step, an RNA is captured by biotinylated DNA probes that have been conjugated to magnetic streptavidin beads. After extraneous RNA has been washed away, a second round of DNA probes that cover the full length of the RNA target is added. While the first set of DNA probes must be specific in order to ensure that only the desired RNA target is captured, the second round of probes does not need to be specific because only the target RNA is present in the wells for this step. The hybrids are then detected by the two-step Hybrid Capture antibody system (Qiagen Gaithersburg, Inc., Gaithersburg, M(D) and the signal is read on a luminometer. This method allows for linear detection of RNA based on both quantity and length. One may apply a "molecular ruler" concept to this assay in which increasing amounts of signal probes may be added to determine, for example, the length of a transcript.

Although the following Examples use RNA, the general concept may be applied to any form of nucleic acid.

Example 18: Materials and Methods

In Vitro Transcribed RNA

In vitro transcribed RNA from HPV 16 RNA for E6/E7 (790 nucleotides) was used in some of the following examples. The RNA was prepared with standard cloning techniques using HPV 16 plasmid as a template (GenBank NC_01526, X05015)

Clinical Samples

Cervical specimens in PRESERVCYT™ media testing positive for high-risk HPV via the Hybrid Capture II test were obtained during 2009. All samples were genotyped using gp+ consensus primers. Representative samples testing positive for HPV 16 were used in this study. Of these, 14 were diagnosed as LSIL and 35 as high-grade cervical interepithelial neoplasia (HSIL). Each sample was analyzed for the integrity of E2 gene expression.

RNA Extraction

RNA was extracted from samples using the QIAZOL™ reagent (Qiagen GmbH, Hilden, Germany). The entire contents of the sample (ranging from 2-16 ml) was centrifuged for 15 min. The cell pellet was resuspended in 3 ml QIAZOL™ and incubated at RT for 5 min to achieve complete lysis. 0.6 ml of chloroform was then added and the samples were shaken vigorously, then incubated again for 2-3 min at RT and centrifuged for 15 min at 12,000×g. The colorless aqueous layer was transferred to a new tube containing 1.5 ml isopropanol and was incubated at RT for 10 min. Another centrifugation at 12,000×g for 10 min at 4° C. was then performed during which a precipitate formed on the side of the tube. The supernatant was removed and the pellet was washed once with 3 ml 75% ethanol. After the pellet was allowed to air-dry for 10 min, it was resuspended in 50 μl molecular biology grade water.

DNA Probes

DNA capture probes for HPV 16 of 35 nucleotides each were designed using BLAST (NCBI) to be specific against other HPV types. These probes were spaced along the HPV gene so that each possible RNA transcript would be captured by a probe. These capture probes were synthesized with a biotin on the 5' end. Signal probes were then designed to cover the remainder of the HPV 16 gene. Length of these probes varied from 28 to 42 nucleotides and the OligoAnalyzer program (Integrated DNA Technologies, Inc., Coralville, Iowa) was used to achieve optimal thermodynamic stability and consistency. These probes were then pooled in a probe cocktail. A separate probe cocktail, lacking all probes in the E2 region, was also made.

TABLE 5

| Region Detected | Position HPV 16 (GenBank NC 001526) |
|---|---|
| All early genes | 130-164 |
| E6 (unspliced, E6*1, E6*2) | 592-626 |
| E1 | 1803-1837 |
| E2-amino | 3014-3048 |
| E2-hinge | 3359-3393 |
| E2-carboxyl | 3851-3885 |
| L2 | 4907-4941 |
| L1 | 6476-6510 |

DNA probes were used in the reverse hybrid capture HPV 16 E2 disruption assay. Two probe sets were used in the assay, set one included probes spread along the HPV 16 genome and set two was a subset with no probes included for the E2 gene region. The probes are listed in Tables 6 & 7, with the biotinylated capture probes listed in Table 7.

TABLE 6

| SEQ ID NO | Name | Sequence 5'-3' antisense | Probe set |
|---|---|---|---|
| 111 | HPV16-129-33 | GGTCGCTCCTGTGGGTCCTGAAACATTGCAGTT | 1, 2 |
| 112 | HPV16-193-28 | CATTCTAATATTATATCATGTATAGTTG | 1, 2 |
| 113 | HPV16-225-32 | TCACGTCGCAGTAACTGTTGCTTGCAGTACAC | 1, 2 |
| 114 | HPV16-262-37 | TACTATGCATAAATCCCGAAAAGCAAAGTCATATACC | 1, 2 |
| 115 | HPV16-298-36 | TTTATCACATACAGCATATGGATTCCCATCTCTATA | 1, 2 |
| 116 | HPV16-335-37 | GTCTATACTCACTAATTTTAGAATAAAACTTTAAACA | 1, 2 |
| 51 | HPV16-371-36 | GTTCTAATGTTGTTCCATACAAACTATAACAATAAT | 1, 2 |
| 52 | HPV16-408-37 | CTAATTAACAAATCACACAACGGTTTGTTGTATTGCT | 1, 2 |
| 56 | HPV16-447-39 | TTTTCTTCAGGACACAGTGGCTTTTGACAGTTAATACAC | 1, 2 |
| 57 | HPV16-486-39 | ATATTATGGAATCTTTGCTTTTTGTCCAGATGTCTTTGC | 1, 2 |
| 58 | HPV16-525-39 | CTGCAACAAGACATACATCGACCGGTCCACCGACCCCTT | 1, 2 |
| 59 | HPV16-556-31 | CAGCTGGGTTTCTCTACGTGTTCTTGATGAT | 1, 2 |
| 117 | HPV16-591-35 | TTCATGCAATGTAGGTGTATCTCCATGCATGATTA | 1, 2 |
| 118 | HPV16-669-42 | ATCCTCCTCCTCTGAGCTGTCATTTAATTGCTCATAACAGTAG | 1, 2 |
| 119 | HPV16-700-31 | GTTCTGCTTGTCCAGCTGGACCATCTATTTC | 1, 2 |
| 120 | HPV16-731-31 | AAGGTTACAATATTGTAATGGGCTCTGTCCG | 1, 2 |
| 121 | HPV16-762-31 | CAACCGAAGCGTAGAGTCACACTTGCAACAA | 1, 2 |
| 122 | HPV16-838-41 | TGGGGCACACAATTCCTAGTGTGCCCATTAACAGGTCTTCC | 1, 2 |
| 123 | HPV16-880-42 | CTGCAGGATCAGCCATGGTAGATTATGGTTTCTGAGAACAGA | 1, 2 |
| 124 | HPV16-915-35 | TCCATTACATCCCGTACCCTCTTCCCCATTGGTAC | 1, 2 |
| 125 | HPV16-950-35 | GTTTTTTTTTCCACTACAGCCTCTACATAAAACCA | 1, 2 |

TABLE 6-continued

| SEQ ID NO | Name | Sequence 5'-3' antisense | Probe set |
|---|---|---|---|
| 126 | HPV16-985-35 | CATTTTCGTTCTCGTCATCTGATATAGCATCCCCT | 1, 2 |
| 127 | HPV16-1020-35 | TATAAAATCTACCAAATCTTCACCTGTATCACTGT | 1, 2 |
| 128 | HPV16-1055-35 | GTTTCTGCCTGTGTTAAATAATCATTATCATTTAC | 1, 2 |
| 129 | HPV16-1090-35 | CTTCCTGTGCAGTAAACAACGCATGTGCTGTCTCT | 1, 2 |
| 130 | HPV16-1125-35 | TTTTAGAACCTGTACTGCATCTCTATGTTGTTTTG | 1, 2 |
| 131 | HPV16-1160-35 | ACTAATATCACTAAGTGGACTACCAAATACTTTCG | 1, 2 |
| 132 | HPV16-1195-35 | TTTAATCTAGGACTAATATTATTGTCTACACATCC | 1, 2 |
| 133 | HPV16-1230-35 | TTGCAGCTCTACTTTGTTTTTCTATACATATAGCT | 1, 2 |
| 134 | HPV16-1265-35 | ATACCCGCTGTCTTCGCTTTCAAATAATCTCCTTT | 1, 2 |
| 135 | HPV16-1300-35 | TGTAACATCTGCTGAGTTTCCACTTCAGTATTGCC | 1, 2 |
| 136 | HPV16-1335-35 | TACATGGTGTTTCAGTCTCATGGCGCCCTTCTACC | 1, 2 |
| 137 | HPV16-1370-35 | ACTGCAACCACCCCCACTTCCACCACTATACTGAC | 1, 2 |
| 138 | HPV16-1405-35 | CTAACACCCTCTCCCCCACTTCCACTACTGTACTG | 1, 2 |
| 139 | HPV16-1440-35 | TTGTAAGTGGTGTTTGGCATATAGTGTGTCTTTCA | 1, 2 |
| 140 | HPV16-1475-35 | CTTTGCATTACTAGTTTTTAGTACATTTAAAATAT | 1, 2 |
| 141 | HPV16-1510-35 | CCGTATAACTCTTTAAATTTTGCTAACATTGCTGC | 1, 2 |
| 142 | HPV16-1545-35 | TTTTAAATGGTCTTACTAATTCTGAAAAACTCACC | 1, 2 |
| 143 | HPV16-1580-35 | AGCAATACACCAATCGCAACACGTTGATTTATTAC | 1, 2 |
| 144 | HPV16-1615-35 | ATACTGTCAGCTATACTGGGTGTAAGTCCAAATGC | 1, 2 |
| 145 | HPV16-1650-35 | GTAAATATAAACAATATTGTTGTAATAGTGTTTTT | 1, 2 |
| 146 | HPV16-1685-35 | AACCATTCCCCATGAACATGCTAAACTTTGAATGT | 1, 2 |
| 147 | HPV16-1724-39 | TCTATTTTTTCCACATTTATATCTTACTAATAGTAACAC | 1, 2 |
| 148 | HPV16-1763-39 | CACACATAATAGTTTAGACAGCAATTTTTCAATTGTTAC | 1, 2 |
| 149 | HPV16-1802-39 | ACGCAATTTTGGAGGCTCTATCATCATACACATTGGAGA | 1, 2 |
| 150 | HPV16-1872-35 | GCGTGTCTCCATACACTTCACTAATATTTGATATA | 1, 2 |
| 151 | HPV16-1907-35 | ATGTTGTAATACTGTTTGTCTTTGTATCCATTCTG | 1, 2 |
| 152 | HPV16-1942-35 | ATCTGTGATAATTCAAATGTACAATCATTAAAACT | 1, 2 |
| 153 | HPV16-1977-35 | CGTCTACTATGTCATTATCGTAGGCCCATTGTACC | 1, 2 |
| 154 | HPV16-2012-35 | TGCCAATTGTGCATATTTATATGCAATTTCACTAT | 1, 2 |
| 155 | HPV16-2047-35 | CTTTTTAGAAAGGCACTTGCATTACTATTAGTGTC | 1, 2 |
| 156 | HPV16-2082-35 | TTGCACAATCCTTTACAATTTTTGCCTGTGAATTA | 1, 2 |
| 157 | HPV16-2117-35 | TTTTTTTTCTGCTCGTTTATAATGTCTACACATTG | 1, 2 |
| 158 | HPV16-2152-35 | CATCTATATTTTATCCATTGACTCATACTCATTTG | 1, 2 |
| 159 | HPV16-2187-35 | TTTGCTTCCAATCACCTCCATCATCTACCCTATCA | 1, 2 |
| 160 | HPV16-2222-35 | AAACTCTACACCTTGATACCTTAAAAACATAACAA | 1, 2 |
| 161 | HPV16-2257-35 | TGCAAAAATCTTTTTAATGCAGTTAAAAATGACAT | 1, 2 |
| 162 | HPV16-2292-35 | CATATAGTAATATGCAATTTTTTTTAGGTATGCCT | 1, 2 |
| 163 | HPV16-2327-35 | CATACCAAATAATGATTTACCTGTGTTAGCTGCAC | 1, 2 |

TABLE 6-continued

| SEQ ID NO | Name | Sequence 5'-3' antisense | Probe set |
|---|---|---|---|
| 164 | HPV16-2362-35 | CATATTACAGACCCTTGCAGAAATTTCATTAAACT | 1, 2 |
| 165 | HPV16-2397-35 | GTTGTAACCAAAAATGGCTTTTAGAATTTACAAAA | 1, 2 |
| 166 | HPV16-2432-35 | ATCATCTAACATACCTATTTTGGCATCTGCTAATG | 1, 2 |
| 167 | HPV16-2467-35 | TTGTCATCTATGTAGTTCCAACAGGGCACTGTAGC | 1, 2 |
| 168 | HPV16-2502-35 | TAGAAACTAAATTTCCATCCAATGCATTTCTTAAA | 1, 2 |
| 169 | HPV16-2537-35 | TTTTAGTTGTACCAATGGTCTATGCTTTACATCCA | 1, 2 |
| 170 | HPV16-2572-35 | GCATTAATGTTAGATGTAATTAATAATGGAGGGCA | 1, 2 |
| 171 | HPV16-2607-35 | TATTATGTAAATAAGGCCACCTAGAATCTGTACCA | 1, 2 |
| 172 | HPV16-2642-35 | TGGAAACTCATTAGGAAATGTAAACACCACCAATC | 1, 2 |
| 173 | HPV16-2677-35 | TTAAGCTCATACACTGGATTTCCGTTTTCGTCAAA | 1, 2 |
| 174 | HPV16-2709-32 | TCCTTGAGAAAAAGGATTTCCAGTTCTTATCA | 1, 2 |
| 175 | HPV16-2743-34 | TCCTCGTCCTCGTGCAAACTTAATCTGGACCACG | 1 |
| 176 | HPV16-2777-34 | AAACGTTGGCAAAGAGTCTCCATCGTTTTCCTTG | 1 |
| 177 | HPV16-2810-33 | TAATGTGTTAGTATTTTGTCCTGACACACATTT | 1 |
| 178 | HPV16-2844-34 | TATATGGTCACGTAGGTCTGTACTATCATTTTCA | 1 |
| 179 | HPV16-2878-34 | TAGCACATTCTAGGCGCATGTGTTTCCAATAGTC | 1 |
| 180 | HPV16-2912-34 | TGTTTAAATCCCATTTCTCTGGCCTTGTAATAAA | 1 |
| 181 | HPV16-2945-33 | ACAGCCAGTGTTGGCACCACTTGGTGGTTAATA | 1 |
| 182 | HPV16-2979-34 | CAGTTCAATTGCTTGTAATGCTTTATTCTTTGAT | 1 |
| 183 | HPV16-3013-34 | ATTGTGAGTTATATATTGTTTCTAACGTTAGTTG | 1 |
| 184 | HPV16-3088-40 | TTTTTATACATCCTGTTGGTGCAGTTAAATACACTTCAAG | 1 |
| 185 | HPV16-3129-41 | TATGTCTCCATCAAACTGCACTTCCACTGTATATCCATGTT | 1 |
| 186 | HPV16-3169-40 | TATATATATGTGTCCAGTTTGTATAATGCATTGTATTGCA | 1 |
| 187 | HPV16-3204-35 | ACCCTCTACCACAGTTACTGATGCTTCTTCACAAA | 1 |
| 188 | HPV16-3235-31 | ATGAACATAATATAAACCATAATAGTCAACTTG | 1 |
| 189 | HPV16-3301-29 | CTTTATTTTTACTATATTTTTCTGCATCA | 1 |
| 190 | HPV16-3329-28 | ACCTGACCACCCGCATGAACTTCCCATA | 1 |
| 191 | HPV16-3358-29 | TGCTAAACACAGATGTAGGACATAATATT | 1 |
| 192 | HPV16-3425-32 | GTATGGGTCGCGGCGGGGTGGTTGGCCAAGTG | 1 |
| 193 | HPV16-3460-35 | TCTGTGTTTCTTCGGTGCCCAAGGCGACGGCTTTG | 1 |
| 194 | HPV16-3494-34 | GTGTCTGGCTCTGATCTTGGTCGCTGGATAGTCG | 1 |
| 195 | HPV16-3528-34 | GTGCAACAACTTAGTGGTGTGGCAGGGGTTTCCG | 1 |
| 196 | HPV16-3562-34 | CAGTGAGGATTGGAGCACTGTCCACTGAGTCTC | 1 |
| 197 | HPV16-3598-36 | TACAGTTAATCCGTCCTTTGTGTGAGCTGTTAAATG | 1 |
| 198 | HPV16-3632-34 | CCTTTTAAATGTACTATGGGTGTAGTGTTACTAT | 1 |
| 199 | HPV16-3667-35 | ATCTATATCTTAAACATTTTAAAGTATTAGCATCA | 1 |
| 200 | HPV16-3703-36 | ACGACACTGCAGTATACAATGTACAATGCTTTTTAA | 1 |
| 201 | HPV16-3738-35 | ATGTTTTACATTATGTCCTGTCCAATGCCATGTAG | 1 |

TABLE 6-continued

| SEQ ID NO | Name | Sequence 5'-3' antisense | Probe set |
|---|---|---|---|
| 202 | HPV16-3774-36 | TTCACTATCATATGTAAGTGTAACAATTGCACTTTT | 1 |
| 203 | HPV16-3812-38 | GGTATTTTAACTTGAGACAAAAATTGGTCACGTTGCCA | 1 |
| 204 | HPV16-3850-38 | ATATAGACATAAATCCAGTAGACACTGTAATAGTTTTT | 1 |
| 205 | HPV16-3918-33 | CACAAAAGCACACAAAGCAAAGCAAAAAGCACG | 1 |
| 206 | HPV16-3952-34 | AGACAAAAGCAGCGGACGTATTAATAGGCAGACA | 1 |
| 207 | HPV16-3988-36 | TAATACCAATATTATTAATGATGTGTATGTAGACAC | 1 |
| 208 | HPV16-4023-35 | CACCTAAACGCAGAGGCTGCTGTTATCCACAATAG | 1 |
| 209 | HPV16-4059-36 | AATGGTATATAAACAAATATAATATATACAATAAAA | 1 |
| 210 | HPV16-4094-35 | TAATTAAAAAGCGTGCATGTGTATGTATTAAAAAT | 1 |
| 211 | HPV16-4130-36 | ATATGTAACAATTACATTATGTACATATACATTATG | 1 |
| 212 | HPV16-4165-35 | AAAGAAAAAATAGTAAGTTATGGTATACAACAATT | 1 |
| 213 | HPV16-4201-36 | AAACAAACAAAAAAAAAAATTATATATGAAAATAAA | 1 |
| 214 | HPV16-4236-35 | ATTGTTAAGTAATAACAGTTTATTAAAAAACAAAC | 1, 2 |
| 215 | HPV16-4271-35 | CACGTTTTGTGCGTTTTGCAGAACGTTTGTGTCGC | 1, 2 |
| 216 | HPV16-4306-35 | CTGTTTGCATGTTTTATAAAGTTGGGTAGCCGATG | 1, 2 |
| 217 | HPV16-4341-35 | ACCTTAGGTATAATGTCAGGTGGACATGTACCTGC | 1, 2 |
| 218 | HPV16-4376-35 | ATTGTAATATTTGTTCAGCAATAGTTTTGCCTTCA | 1, 2 |
| 219 | HPV16-4411-35 | TCCTAACCCACCAAAAAATACACCCATACTTCCAT | 1, 2 |
| 220 | HPV16-4446-35 | CCAGTGCGTCCGCCTGTACCCGACCCTGTTCCAAT | 1, 2 |
| 221 | HPV16-4481-35 | TAGCTGTGGGAGGCCTTGTTCCCAATGGAATATAC | 1, 2 |
| 222 | HPV16-4516-35 | TGTTAAAGGGGGTCTTACAGGAGCAAGTGTATCTG | 1, 2 |
| 223 | HPV16-4551-35 | ACTATAGAAGGATCAGAAGGGCCCACAGGATCTAC | 1, 2 |
| 224 | HPV16-4586-35 | CAGCATCAATAAAACTAGTTTCTTCCACTAAAGAA | 1, 2 |
| 225 | HPV16-4621-35 | ATCTGGGGGAATGGAAGGTACAGATGTTGGTGCAC | 1, 2 |
| 226 | HPV16-4656-35 | GTATCAGTTGAAGTAGTAATACTAAATCCTGATAC | 1, 2 |
| 227 | HPV16-4691-35 | TAACAGTATTATTAATATCTAATATAGCAGGTGTG | 1, 2 |
| 228 | HPV16-4726-35 | AGTGAAAGTGGGATTATTATGTGTAGTAACAGTAG | 1, 2 |
| 229 | HPV16-4762-36 | TTCTGCAGGTGTTGGAGGCTGCAATACAGATGGGTC | 1, 2 |
| 230 | HPV16-4798-36 | AATAGTGGATGATGAAAGTGTAAAATGCCCTCCAGT | 1, 2 |
| 231 | HPV16-4834-36 | TGTATCCATAGGAATTTCTTCATAATTATGTGTACT | 1, 2 |
| 232 | HPV16-4870-36 | ACTAGTTACTGTGTTAGGGTTTGTGCTAACAATAAA | 1, 2 |
| 233 | HPV16-4906-36 | GCGTGCCACTGGGCGAGACCCTGGTATGGGTGTGCT | 1, 2 |
| 234 | HPV16-4975-34 | AGTGGGAGTGGTTACAAAAGCAGGGTCTACAACT | 1, 2 |
| 235 | HPV16-5010-35 | CCTTCATATGCAGGATTATCATATGTAATAAGTTT | 1, 2 |
| 236 | HPV16-5045-35 | TACTAGAAAAATATAATGTATTATCCACATCTATA | 1, 2 |
| 237 | HPV16-5080-35 | GTCAGGATCTGGAGCTATATTAATACTATTATCAT | 1, 2 |
| 238 | HPV16-5115-35 | AATGCTGGCCTATGTAAAGCAACTATATCCAAAAA | 1, 2 |
| 239 | HPV16-5150-35 | TTCTACTGTACCTAATGCCAGTACGCCTAGAGGTT | 1, 2 |

TABLE 6-continued

| SEQ ID NO | Name | Sequence 5'-3' antisense | Probe set |
|---|---|---|---|
| 240 | HPV16-5185-35 | TCCACTACGAGTACGTAGTGTTTGTTTATTACCAA | 1, 2 |
| 241 | HPV16-5220-35 | TCATAATAATAATGTACCTTAGCACCTATAGATTT | 1, 2 |
| 242 | HPV16-5255-35 | ATTCTATTTCTTCTGCAGGATCAATAGTACTTAAA | 1, 2 |
| 243 | HPV16-5290-35 | AGTGGTAGTATATGTAGAAGGTGTTATAGTTTGTA | 1, 2 |
| 244 | HPV16-5325-35 | CCATTATTAATAGAAGTAGGTGAGGCTGCATGTGA | 1, 2 |
| 245 | HPV16-5360-35 | CTGTAATAAAGTCATCTGCATAAATATCATATAAT | 1, 2 |
| 246 | HPV16-5395-35 | AGAGGGTACAGATGGTACCGGGGTTGTAGAAGTAT | 1, 2 |
| 247 | HPV16-5430-35 | GTTGTATTTGCAGGAATATAACCTGATAAAGATGT | 1, 2 |
| 248 | HPV16-5465-35 | CTAAAGGAATATTGTATGCACCACCAAAAGGAATT | 1, 2 |
| 249 | HPV16-5500-35 | GTCAGTTATATTAATGGGTATATCAGGACCTGATA | 1, 2 |
| 250 | HPV16-5535-35 | GACCCTGGAACTATAGGAATTAATGAAGGAGCTTG | 1, 2 |
| 251 | HPV16-5570-35 | AGTCACCTGCATCAGCAATAATTGTATATTGTGGA | 1, 2 |
| 252 | HPV16-5604-34 | TTTCGTAACATGTAATAACTAGGATGTAAATAAA | 1, 2 |
| 253 | HPV16-5638-34 | ATCTGAAAAAAAATATGGTAAACGTTTACGTCGT | 1, 2 |
| 254 | HPV16-5675-37 | CAAGTAGACAGTGGCCTCACTAGGCAGCCAAAGAGAC | 1, 2 |
| 255 | HPV16-5713-38 | TCATCCGTGCTTACAACCTTAGATACTGGGACAGGAGG | 1, 2 |
| 256 | HPV16-5750-37 | TCCTGCATGATAATATATGTTTGTGCGTGCAACATAT | 1, 2 |
| 257 | HPV16-5788-38 | GGAAAATAGGGATGTCCAACTGCAAGTAGTCTGGATGT | 1, 2 |
| 258 | HPV16-5823-35 | GAACTAATATTTTGTTATTGTTAGGTTTTTTAATA | 1, 2 |
| 259 | HPV16-5857-34 | CTAAATACCCTGTATTGTAATCCTGATACTTTAG | 1, 2 |
| 260 | HPV16-5891-34 | AAAACCAAACTTATTGGGGTCAGGTAAATGTATT | 1, 2 |
| 261 | HPV16-5926-35 | CGCTGTGTATCTGGATTATAAAATGAGGTGTCAGG | 1, 2 |
| 262 | HPV16-5960-34 | ACCTACCTCAACACCTACACAGGCCCAAACCAGC | 1, 2 |
| 263 | HPV16-5994-34 | GGCCACTAATGCCCACACCTAATGGCTGACCACG | 1, 2 |
| 264 | HPV16-6029-35 | ATTTTCTGTGTCATCCAATTTATTTAATAAAGGAT | 1, 2 |
| 265 | HPV16-6063-34 | TATCCACACCTGCATTTGCTGCATAAGCACTAGC | 1, 2 |
| 266 | HPV16-6097-34 | GTTTGTTTGTAATCCATAGATATACATTCTCTAT | 1, 2 |
| 267 | HPV16-6132-35 | CTATAGGTGGTTTGCAACCAATTAAACACAATTGT | 1, 2 |
| 268 | HPV16-6166-34 | TTGGTACATGGGGATCCTTTGCCCCAGTGTTCCC | 1, 2 |
| 269 | HPV16-6200-34 | TAATGGTGGACAATCACCTGGATTTACTGCAACA | 1, 2 |
| 270 | HPV16-6235-35 | ATATCACCATCCTGAATAACTGTGTTTATTAACTC | 1, 2 |
| 271 | HPV16-6269-34 | AGTAAAGTCCATAGCACCAAAGCCAGTATGAACC | 1, 2 |
| 272 | HPV16-6303-34 | CCAGTGGAACTTCACTTTTGTTAGCCTGTAATGT | 1, 2 |
| 273 | HPV16-6338-35 | ATAATCTGGATATTTGCAAATAGATGTACAAATAT | 1, 2 |
| 274 | HPV16-6372-34 | AGCTGTCGCCATATGGTTCTGACACCATTTTAAT | 1, 2 |
| 275 | HPV16-6406-34 | ACAAACATTTGTTCCCTTCGTAAATAAAAAAATA | 1, 2 |
| 276 | HPV16-6441-35 | CACCAACAGTACCAGCCCTATTAAATAAATGTCTA | 1, 2 |
| 277 | HPV16-6475-34 | GAGCCTTTAATGTATAAATCGTCTGGTACATTTT | 1, 2 |

TABLE 6-continued

| SEQ ID NO | Name | Sequence 5'-3' antisense | Probe set |
|---|---|---|---|
| 278 | HPV16-6546-36 | CATCAGAGGTAACCATAGAACCACTAGGTGTAGGAA | 1, 2 |
| 279 | HPV16-6582-36 | CTCGTTGTAACCAATAAGGTTTATTGAATATTTGGG | 1, 2 |
| 280 | HPV16-6618-36 | GGTTACCCCAACAAATGCCATTATTGTGGCCCTGTG | 1, 2 |
| 281 | HPV16-6653-35 | ACTGCGTGTAGTATCAACAACAGTAACAAATAGTT | 1, 2 |
| 282 | HPV16-6689-36 | TGAAGTAGATATGGCAGCACATAATGACATATTTGT | 1, 2 |
| 283 | HPV16-6725-36 | GTACTCCTTAAAGTTAGTATTTTTATATGTAGTTTC | 1, 2 |
| 284 | HPV16-6761-36 | AATAAACTGTAAATCATATTCCTCCCCATGTCGTAG | 1, 2 |
| 285 | HPV16-6796-35 | ACGTCTGCAGTTAAGGTTATTTTGCACAGTTGAAA | 1, 2 |
| 286 | HPV16-6832-36 | AAAATAGTGGAATTCATAGAATGTATGTATGTCATA | 1, 2 |
| 287 | HPV16-6868-36 | CCTGGGGGAGGTTGTAGACCAAAATTCCAGTCCTCC | 1, 2 |
| 288 | HPV16-6903-35 | GGGTTACAAACCTATAAGTATCTTCTAGTGTGCCT | 1, 2 |
| 289 | HPV16-6939-36 | GTGCTGGAGGTGTATGTTTTTGACAAGCAATTGCCT | 1, 2 |
| 290 | HPV16-6975-36 | AAAAAGTGTATTTTTTAAGGGGATCATCTTCTTTAG | 1, 2 |
| 291 | HPV16-7011-36 | GGTCTGCAGAAAACTTTTCCTTTAAATTTACTTCCC | 1, 2 |
| 292 | HPV16-7047-36 | GTAGTAAAAATTTGCGTCCTAAAGGAAACTGATCT | 1, 2 |
| 293 | HPV16-7082-35 | TAATGTAAATTTTGGTTTGGCCTTCAATCCTGCTT | 1, 2 |
| 294 | HPV16-7115-33 | AGATGAGGTGGTGGGTGTAGCTTTTCGTTTTCC | 1, 2 |
| 295 | HPV16-7141-25 | CACATACAACTTAATATTTACAAGC | 1, 2 |
| 296 | HPV16-7148-33 | CTTACGTTTTTTGCGTTTAGCAGTTGTAGAGGT | 1, 2 |
| 297 | HPV16-7181-33 | AACACTAATTCAACATACATACAATACTTACAG | 1, 2 |
| 298 | HPV16-7216-35 | ACATACAAGCACATACAAACATATACACAACAAAC | 1, 2 |
| 299 | HPV16-7265-24 | TTTATTATACCATACATACAAACA | 1, 2 |

TABLE 7

| SEQ ID NO | Name | Sequence |
|---|---|---|
| 300 | HPV16 CP1 | ACAACTATACATGATATAATATTAGAATGTGTGTAC |
| 301 | HPV16 CP2 | TCTACTGTTATGAGCAATTAAATGACAGCTCAGAGG |
| 302 | HPV16 CP3 | TGGAAGACCTGTTAATGGGCACACTAGGAATTGTGT |
| 303 | HPV16 CP4 | GTATATCAAATATTAGTGAAGTGTATGGAGACACGC |
| 304 | HPV16 CP5 | CCTTGAAGTGTATTTAACTGCACCAACAGGATGTAT |
| 305 | HPV16 CP6 | ACTTGGCCAACCACCCCGCCGCGACCCATACCAAAG |
| 306 | HPV16 CP7 | GCGTGCTTTTTGCTTTGCTTTGTGTGCTTTTGTGTG |
| 307 | HPV16 CP8 | AAGTTGTAGACCCTGCTTTTGTAACCACTCCCACTA |
| 308 | HPV16 CP9 | TTCCTACACCTAGTGGTTCTATGGTTACCTCTGATG |

Bead/Probe Conjugation

Magnetic streptavidin beads (5% solids, Seradyn, Inc., Indianapolis, Ind.), were vortexed and washed twice in a Tween-based wash buffer. They were then incubated with a cocktail of biotinylated capture probes comprising 180 nM/probe and incubated at 37° C. for 30 min with shaking at 1150 RPM. The beads were pelleted, washed three more times, and resuspended in a casein blocking solution for storage at 4° C.

E2 Integrity Assay

20 µl of Qiazol extracted RNA in 30 µl of a chaotropic salt solution was captured onto 10 µl of the bead-conjugated capture probes for 30 min at 60° C. with shaking. After this step the sample was split by pipetting 30 µl of the reaction into two separate clean wells on the same 96-well plate. A magnetic rack was then used to pull the bead-probe-RNA complex down and the resulting pellet was washed with a buffered saline-detergent solution twice, once for 2 min and once for 5 min. The signal probe cocktails, one with all probes and one without E2-region probes, were then added at 4.2 nM in 65 µl of a nucleic acid hybridization buffer and the hybridization reaction was performed for 30 min at 60° C. with shaking. After this reaction the bead complex was again pelleted and the plate was dried on absorbent paper towels. A solution of anti-DNA:RNA nucleic acid hybrid antibody conjugated with alkaline phosphatase, was added at 45 µl/well and the plate was incubated for 30 min at 45°. The beads were again pelleted and washed five times for one min/wash, this time with a Tris-based wash buffer. 35 μl of chemiluminescent alkaline phosphatase substrate was then added and the plate was shaken at 350 RPM for 15 min at room temperature under a foil seal to protect the samples from light. The luminescence from the wells was then read on a QIAGEN® DML 3000™ microplate luminometer (Qiagen Gaithersburg, Inc., Gaithersburg, Md.).

The signal:noise ("S/N") of the sample values in the two wells (with and without E2 probes) was determined. Samples with a signal:noise value below 2 in the all-probes well were excluded from statistical analyses. The extent of E2 disruption was determined with the following formula percentage difference: [(S/N(all)−S/N(no E2))/S/N(all)]×100.

Example 19

Figure 13:
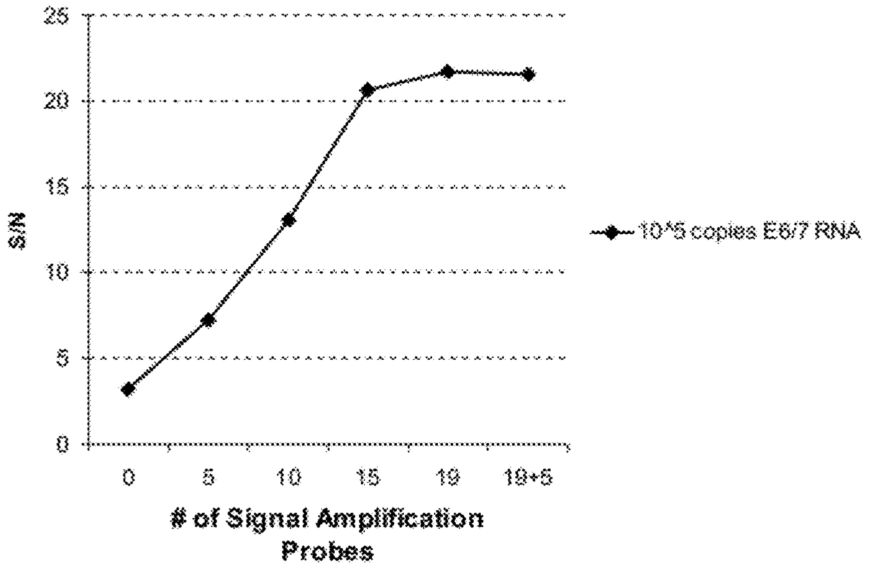
FIG. 13 shows increasing signal as the number of signal amplification probes is increased. In this way, an RNA transcript length may be measured by the increasing signal generated by the increased number of consecutive amplification probes.

An in vitro transcribed HPV E6/E7 was provided as described above. Three biotinylated capture probes of 40 nucleotides each, evenly spaced along the transcript were conjugated to magnetic streptavidin beads as described above. 1×105 copies of the HPV 16 E6/E7 transcript was then captured to the streptavidin beads as described above. Probe cocktails comprising 0, 5, 10, 15, and 19 signal probes for HPV E6/E7 were generated. Excluding the capture probe, 19 signal probes is sufficient to hybridize to the full length of the E6/E7 transcript. Additionally, a probe cocktail comprising 19 signal probes for HPV E6/E7 plus 5 signal probes for HPV 16 L1 was generated. The S/N ratio was calculated for each probe cocktail. Results are shown at FIG. 13. As can be seen, signal intensity increases in a somewhat linear fashion with increasing numbers of probes.

Example 20

Figure 22:
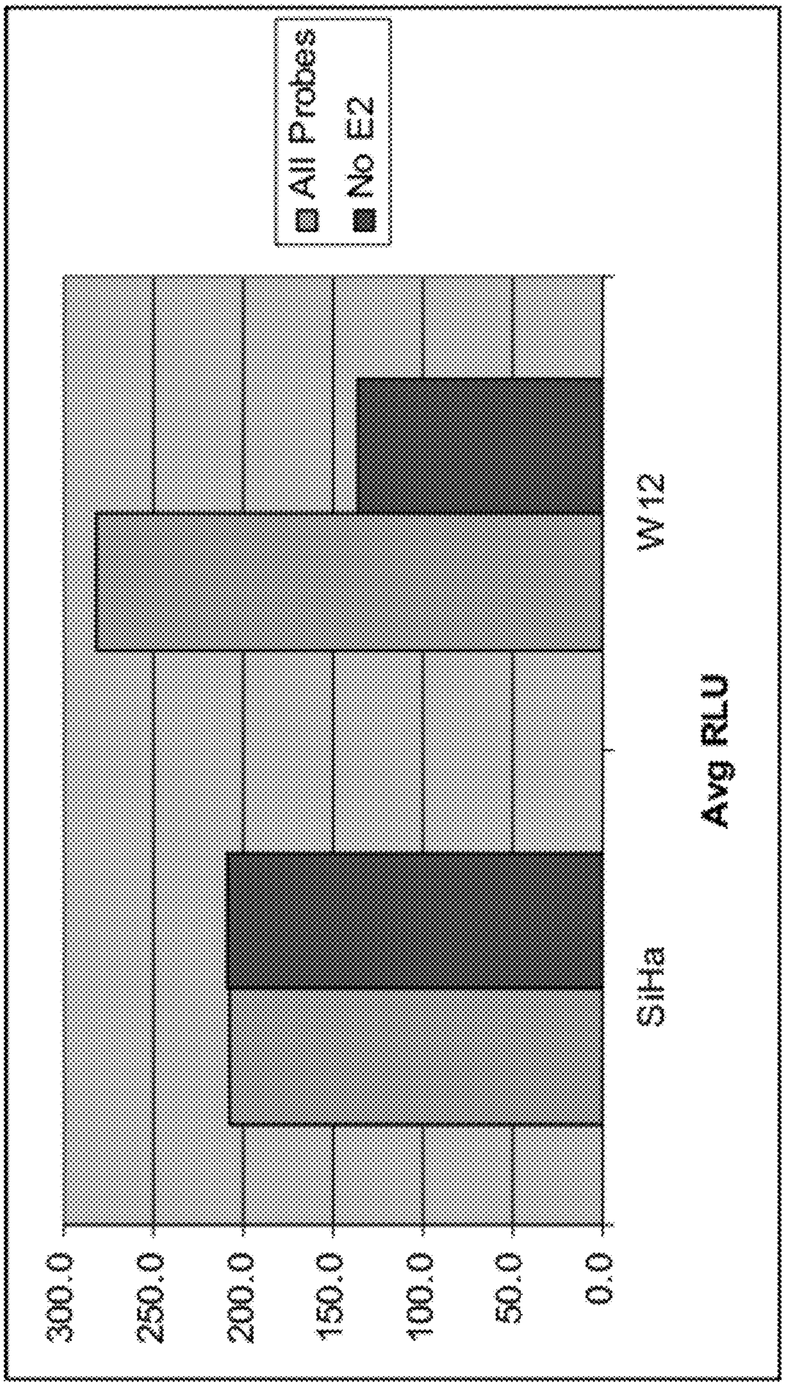
FIG. 22 illustrates a comparison of the integrity of E2 gene expression in SiHa and W12 cells.

E2 integrity in SiHa and W12 cells was compared using the methods described at Example 18. SiHa cells comprise an integrated HPV 16 genome, resulting in disruption of the majority of the E2 gene maintained in the cell. In contrast, the HPV 16 genome is maintained in episomal form in W12 cells; thus the E2 gene is intact. Data are shown at FIG. 22. When E2 probes are removed from the signal amplification cocktail, there is no drop in signal in SiHa cells because none of the signal with all of the probes is from the E2 region. However, the signal from W12 drops significantly, indicating that approximately 50% of the RNA transcripts detected are from E2.

Example 21

Figure 23:
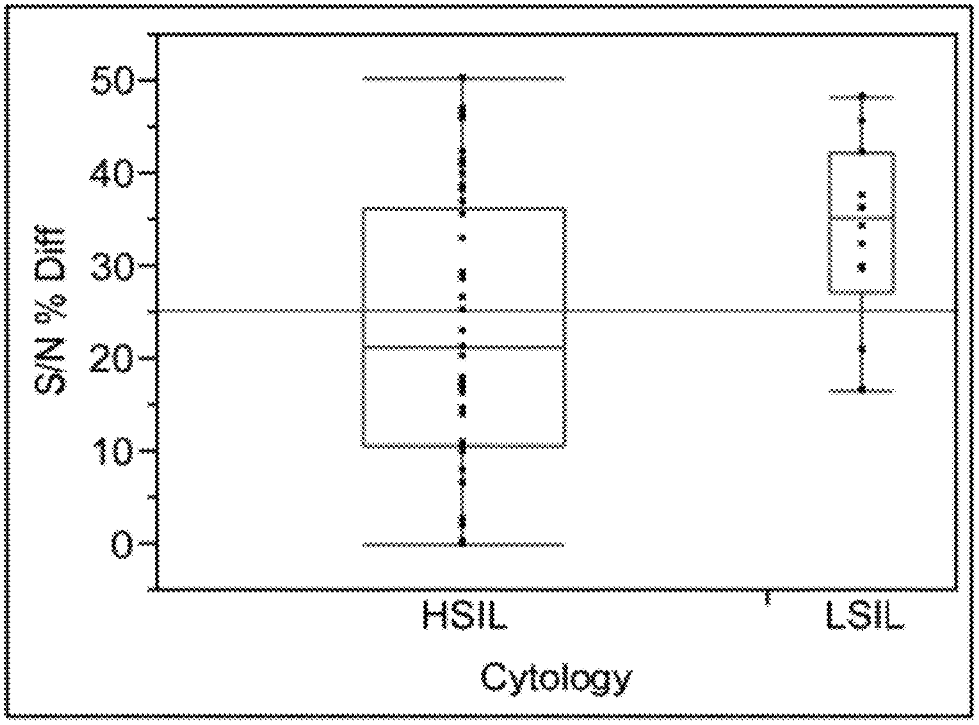
FIG. 23 illustrates a comparison of the integrity of E2 gene expression in LSIL and HSIL samples.

LSIL and HSIL samples were tested in the E2 integrity assay described at Example 18. Data are shown at FIG. 23 and summarized below at Table 8.

TABLE 8

| Level | Minimum | 25% | Median | 75% | Maximum |
|---|---|---|---|---|---|
| HSIL | 2 | 11 | 22.9 | 38.1 | 50.2 |
| LSIL | 16.5 | 34 | 42.9 | 47.7 | 57.2 |

As can be seen, there is a significant difference between LSIL and HSIL samples (p=0.0012). More noteworthy, however, is the distribution of the samples in each lesion category. While the maximum percentage difference for the lesion categories is similar, the minimums are much more different (2 for HSIL and 16.5 for LSIL). This pattern makes sense given that only a small percentage of HSIL samples eventually progress to cervical cancer.

What is claimed is:

1. A method of detecting the presence of a target HPV RNA, the method comprising:

a) providing at least one DNA capture probe;

b) providing a first anti-RNA:DNA hybrid antibody, wherein the first anti-RNA:DNA hybrid antibody is bound to a support;

c) hybridizing the target HPV RNA to said at least one DNA capture probe, yielding a target RNA:DNA capture probe complex;

d) incubating said target HPV RNA:DNA capture probe complex with said anti-RNA:DNA hybrid antibody, yielding a bound target HPV RNA:DNA capture probe complex;

e) providing at least one DNA amplification probe, and hybridizing said at least one DNA amplification probe to said bound target HPV RNA:DNA capture probe complex, yielding a bound target HPV RNA:DNA capture/amplification probe complex;

f) providing a second anti-RNA:DNA hybrid antibody, and incubating said bound target HPV RNA:DNA capture/amplification probe complex with said second anti-RNA:DNA hybrid antibody, yielding a bound target HPV RNA:DNA:antibody complex;

g) detecting said second anti-RNA:DNA hybrid antibody, wherein said detecting indicates the presence of said target HPV RNA, wherein at least one of the capture probes comprises an isolated nucleic acid having an overall length of not more than 50 nucleotides, wherein the isolated nucleic acid comprises at least one nucleotide sequence having at least 75-percent homology to a nucleotide sequence selected from the group consisting of SEQ ID NO: 1 to SEQ ID NO: 20 and SEQ ID NO: 300 to SEQ ID NO: 308, RNA equivalents thereof, and full complements thereof;

wherein the capture probe is not capable of hybridizing to more than one type of HPV genome;

wherein the amplification probe comprises at least one nucleotide sequence having at least 75-percent homology to a nucleotide sequence selected from the group consisting of SEQ ID NO: 21 to SEQ ID NO: 105 and SEQ ID NO: 111 to SEQ ID NO: 299; and wherein the target HPV RNA is not amplified.

2. The method of claim 1, wherein the target HPV RNA is a splice variant, and wherein the at least one DNA capture probe and the at least one DNA amplification probe are selected to detect the presence of said splice variant.

3. A method for determining whether a target nucleic acid is absent from or disrupted in a sample, said method comprising:

a) treating a first portion of the sample under conditions sufficient to induce the formation of:

i) a first set of DNA:RNA hybrids comprising the target nucleic acid; and ii) a second set of DNA:RNA hybrids comprising a reference nucleic acid;

b) treating a second portion of the sample under conditions sufficient to induce the formation of the second set of DNA:RNA hybrids, but not the first set of DNA:RNA hybrids;

c) generating a detectable signal in the first portion of the sample and the second portion of the sample, wherein the detectable signal has an intensity that correlates with the concentration of DNA:RNA hybrids; and d) comparing the intensity of the detectable signal in the first portion of the sample and the intensity of the detectable signal in the second portion of the sample, wherein:

i) the target nucleic acid is intact and present in the sample if the intensity of the detectable signal in the first portion of the sample is greater than the intensity of the detectable signal in the second portion of the sample; and ii) the target nucleic acid is absent from the sample if the intensity of the detectable signal in the first portion of the sample is less than or equal to the intensity of the detectable signal in the second portion of the sample;

wherein the first portion of the sample and the second portion of the sample are formed by a method comprising contacting the sample with a first capture probe set specific for the target nucleic acid, wherein hybridization of the first capture probe set to the target nucleic acid generates a first capture complex; and a second capture probe set specific for the reference nucleic acid, wherein hybridization of the second capture probe set to the reference nucleic acid generates a second capture complex;

wherein the first capture probe set comprises at least two capture probes having an overall length of not more than 50 nucleotides, wherein each capture probe comprises at least one nucleotide sequence having at least 75-percent homology to a nucleotide sequence selected from the group consisting of SEQ ID NO: 51, SEQ ID NO: 52, SEQ ID NO: 56 to SEQ ID NO: 59, and SEQ ID NO: 111 to SEQ ID NO: 299, RNA equivalents thereof, and full complements thereof;

wherein the second capture probe set comprises at least two capture probes having an overall length of not more than 50 nucleotides, wherein each capture probe comprises at least one nucleotide sequence having at least 75-percent homology to a nucleotide sequence selected from the group consisting of SEQ ID NO: 51, SEQ ID NO: 52, SEQ ID NO: 56 to SEQ ID NO: 59, SEQ ID NO: 111 to SEQ ID NO: 174, SEQ ID NO: 214 to SEQ ID NO: 299, RNA equivalents thereof, and full complements thereof;

wherein the first capture probe comprises: i) a region capable of hybridizing to the target nucleic acid; and ii) a region capable of hybridizing to a first nucleic acid sequence of an anchor probe; and the second capture probe comprises: i) a region capable of hybridizing to the target nucleic acid; and ii) a region capable of hybridizing to a second nucleic acid sequence of an anchor probe, and wherein the anchor probe is bound to or adapted to be bound to a first support and/or second support.

4. The method of claim 3, further comprising capturing the first capture complex and the second capture complex to a support.

5. The method of claim 4, wherein the first and second capture probes are bound to or adapted to be bound to the support.

6. The method of claim 5, wherein the capture probes comprise a ligand and the support comprises a ligand-binding moiety.

7. The method of claim 6, wherein the first capture probe and the second capture probe comprise the same ligand.

8. The method of claim 6, wherein the first capture probe and the second capture probe comprise different ligands, wherein:

a) the first portion of the sample is contacted with a first set of solid supports comprising a ligand binding moiety capable of binding the ligand of the first capture probe and a ligand binding moiety capable of binding the ligand of the second capture probe; and b) the second portion of the sample is contacted with a second set of solid supports comprising a ligand binding moiety capable of binding the ligand of the second capture probe, but not the first capture probe.

9. The method of claim 8, wherein the first portion of the sample and the second portion of the sample is contacted with i) a first probe set comprising a plurality of signal probes capable of hybridizing to the target nucleic acid; and ii) a second probe set comprising a plurality of signal probes capable of hybridizing to the reference nucleic acid.

10. The method of claim 6, wherein the first capture probe and the second capture probe are biotinylated and wherein the first support and the second support comprise a biotin-binding moiety.

11. The method of claim 6, wherein the capture probes are covalently bound to the support.

12. The method of claim 4, wherein:

a) the first and second capture complexes comprise a DNA:RNA hybrid; and b) the first and second capture complexes are captured to the first and second supports by a method comprising contacting the first and second capture complexes with an entity capable of specifically binding to a DNA:RNA hybrid, wherein the entity capable of specifically binding to a DNA:RNA hybrid is bound to the support or adapted to be bound to the support.

13. The method of claim 12, wherein the entity capable of specifically binding to a DNA:RNA hybrid comprises a ligand and the first and second supports comprise a ligand-binding moiety.

14. The method of claim 13, wherein the entity capable of specifically binding to a DNA:RNA hybrid is biotinylated and wherein the support comprises a biotin-binding moiety.

15. The method of claim 12, wherein the entity capable of specifically binding to a DNA:RNA hybrid is covalently bound to the support.

16. The method of claim 12, wherein the entity capable of specifically binding to a DNA:RNA hybrid is a DNA:RNA hybrid-specific antibody or a fragment thereof.

17. The method of claim 3, wherein the first nucleic acid sequence and the second nucleic acid sequence are the same.

18. The method of claim 3, wherein the first nucleic acid sequence and the second nucleic acid sequence are different.

19. The method of claim 18, wherein the first nucleic acid sequence and the second nucleic acid sequence are disposed in the same anchor probe.

20. The method of claim 18, wherein the first nucleic acid sequence and the second nucleic acid sequence are disposed in different anchor probes.

21. The method of claim 3, wherein:

a) the first support comprises an anchor probe comprising the first nucleic acid sequence and an anchor probe comprising second nucleic acid sequence; and b) the second support comprises anchor probes comprising the second nucleic acid sequence, but does not comprise anchor probes comprising the first nucleic acid sequence.

22. The method of claim 3, wherein:

a) the first set of DNA:RNA hybrids is formed by a method comprising contacting the sample with a first signal probe capable of hybridizing to the target nucleic acid; and b) the second set of DNA:RNA hybrids is formed by a method comprising contacting the sample with a second signal probe capable of hybridizing to the reference nucleic acid.

23. The method of claim 22, wherein:

a) the first portion of the sample is contacted with the first signal probe and the second signal probe; and b) the second portion of the sample is contacted with the second signal probe, but not the first signal probe, wherein the first signal probe is specific for the target nucleic acid and the second signal probe is specific for the reference nucleic acid.

24. The method of claim 13, wherein:

a) the first signal probe is disposed in a first probe set comprising a plurality of signal probes capable of hybridizing to the target nucleic acid; and b) the second signal probe is disposed in a second probe set comprising a plurality of signal probes capable of hybridizing to the reference nucleic acid.

25. The method of claim 24, wherein:

a) the plurality of signal probes of the first probe set is capable of hybridizing to at least 70% of the target nucleic acid;

b) the plurality of signal probes of the second probe set is capable of hybridizing to at least 70% of the reference nucleic acid.

26. The method of claim 3, wherein the detectable signal is generated by a method comprising contacting the first portion of the sample and the second portion of the sample with an entity capable of specifically binding to a DNA:RNA hybrid.

27. The method of claim 26, wherein the entity capable of specifically binding a DNA:RNA hybrid is an DNA:RNA hybrid-specific antibody or a fragment thereof.

28. The method of claim 3, further comprising:

a) generating the first portion of the sample and the second portion of the sample by a method comprising:

i) contacting the sample with at least a first biotinylated capture probe specific for the target nucleic acid;

ii) contacting the sample with at least a second biotinylated capture probe specific for the reference nucleic acid;

iii) contacting the sample with a streptavidin-coated magnetic bead under conditions sufficient to permit binding of the biotinylated capture probes to the streptavidin coated bead; and iv) separating the streptavidin coated beads into separate containers to form the first portion of the sample and the second portion of the sample;

b) forming the first set of DNA:RNA hybrids and the second set of DNA:RNA hybrids in the first portion of the sample by a method comprising contacting the first portion of the sample with a probe cocktail comprising:

i) a plurality of detectably labeled nucleic acid probes capable of hybridizing to the target nucleic acid, wherein said plurality is sufficient to cover the target nucleic acid; and ii) a plurality of detectably labeled nucleic acid probes capable of hybridizing to the reference nucleic acid, wherein said plurality is sufficient to cover the target nucleic acid; and c) forming the second set of DNA:RNA hybrids in the second portion of the sample by a method comprising contacting the second portion of the sample with a probe cocktail comprising a plurality of detectably labeled signal probes capable of hybridizing to the reference nucleic acid, wherein said plurality is sufficient to cover the target nucleic acid, wherein the detectable signal is generated by the detectably labeled signal probes.

29. The method of claim 3, wherein:

a) the target nucleic acid is an HPV E2 nucleic acid; and b) the reference nucleic acid is selected from the group consisting of:

i) HPV E1 nucleic acid ii) HPV E6/E7 nucleic acid iii) HPV L1 nucleic acid iv) HPV L2 nucleic acid.

30. The method of claim 29, wherein a group of reference nucleic acids are detected, the group comprising at least two reference nucleic acids selected from the group consisting of:

i) HPV E1 mRNA or cDNA ii) HPV E6/E7 mRNA or cDNA iii) HPV L1 mRNA or cDNA; and iv) HPV L2 mRNA or cDNA.

31. The method of claim 30, wherein the group of reference nucleic acids comprises:

i) HPV E1 mRNA;

ii) HPV E6/E7 mRNA;

iii) HPV L1 mRNA; and iv) HPV L2 mRNA.

32. A method of predicting the onset of HPV-induced cell transformation in a patient, said method comprising detecting the presence or absence of an HPV E2 mRNA in an HPV-infected tissue derived from the patient by the method of claim 29, wherein the absence of HPV E2 mRNA is indicative of the onset of HPV-induced cell transformation.

33. A method of detecting integration of an HPV genome into a genome of a host cell, said method comprising detecting the presence or absence of an HPV E2 mRNA in an HPV-infected tissue derived from the patient by the method of claim 29, wherein the absence of HPV E2 mRNA is indicative of integration of the HPV genome into a genome of a host cell.

* * * * *

SEQUENCE LISTING

```
<160> NUMBER OF SEQ ID NOS: 308

<210> SEQ ID NO 1
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 1

gtttgcagct ctgtgcataa ctgtggtaac tttct                                  35


<210> SEQ ID NO 2
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 2

cagtaactgt tgcttgcagt acacacattc taata                                  35


<210> SEQ ID NO 3
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 3
```

acatatattc atgcaatgta ggtgtatctc catgc 35

<210> SEQ ID NO 4
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 4
aaggttacaa tattgtaatg ggctctgtcc ggttc 35

<210> SEQ ID NO 5
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 5
attaacaggt cttccaaagt acgaatgtct acgtg 35

<210> SEQ ID NO 6
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 6
caatagtcta tatggtcacg taggtctgta ctatc 35

<210> SEQ ID NO 7
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 7
caaggctaac gtcttgtaat gtccactttt catta 35

<210> SEQ ID NO 8
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 8
tataaaccat aatagtcaac ttgaccctct accac 35

<210> SEQ ID NO 9
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 9
ttggtcacgt tgccattcac tatcatatgt aagtg 35

<210> SEQ ID NO 10
<211> LENGTH: 35
<212> TYPE: DNA

<213> ORGANISM: Artificial Sequence
<220> FEATURE:
<223> OTHER INFORMATION: Nucleic acid probe

<400> SEQUENCE: 10
ctgatcttgg tcgctggata gtcgtctgtg tttct 35

<210> SEQ ID NO 11
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 11
tcatagtggt ctatgatttt gtcctgcacg caact 35

<210> SEQ ID NO 12
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 12
tccaatcctc ggttttgtat cgactttgtg caagg 35

<210> SEQ ID NO 13
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 13
tgtgacttac acaggtagcg gttttgtccc atgtt 35

<210> SEQ ID NO 14
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 14
tgggttgaca ggtccacaat gctgcttctc cgcga 35

<210> SEQ ID NO 15
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 15
ccaccaatat ttgtacacta tctggaattg caaca 35

<210> SEQ ID NO 16
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 16
atacacaggt tatttctatg tcttgcagtg aagtg 35

-continued

<210> SEQ ID NO 17
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 17
gcactggcct ctatagtgcc cagctatgtt gtgaa 35

<210> SEQ ID NO 18
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 18
catagaaggt caaccggaat ttcattttgg ggctc 35

<210> SEQ ID NO 19
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 19
cgggctggta aatgttgatg attaactcca tctat 35

<210> SEQ ID NO 20
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 20
cagggtgttc agaaacagct gctggaatgc tcgaa 35

<210> SEQ ID NO 21
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 21
ttttatacat cctgttggtg cagttaaata cactt 35

<210> SEQ ID NO 22
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 22
ccatcaaact gcacttccac tgtatatcca tgttt 35

<210> SEQ ID NO 23
<211> LENGTH: 35
<212> TYPE: DNA
<213> ORGANISM: Artificial Sequence
<220> FEATURE:

-continued

<223> OTHER INFORMATION: Nucleic acid probe

<400> SEQUENCE: 23
tccagtttgt ataatgcatt gtattgcata tgtct 35

<210> SEQ ID NO 24
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 24
agttactgat gcttcttcac aaatatatat atgtg 35

<210> SEQ ID NO 25
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 25
ctttattttt actatatttt tctgcatcat ctttaaa 37

<210> SEQ ID NO 26
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 26
cataatatta cctgaccacc cgcatgaact tcccata 37

<210> SEQ ID NO 27
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 27
agaggatact tcgttgctgc taaacacaga tgtagga 37

<210> SEQ ID NO 28
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 28
cggggtggtt ggccaagtgc tgcctaataa tttcagg 37

<210> SEQ ID NO 29
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 29
ctgcacaaaa tatgttcgta ttccttcatg aacataa 37

<210> SEQ ID NO 30
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 30
tcggtgccca aggcgacggc tttggtatgg gtcgcgg 37

<210> SEQ ID NO 31
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 31
cacacattta aacgttggca aagagtctcc at 32

<210> SEQ ID NO 32
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 32
attttcataa tgtgttagta ttttgtcctg a 31

<210> SEQ ID NO 33
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 33
tagtttttgg tattttaact tgagacaaaa a 31

<210> SEQ ID NO 34
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 34
tcatatagac ataaatccag tagacactgt aa 32

<210> SEQ ID NO 35
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 35
taataaatag cacattctag gcgcatgtgt ttc 33

<210> SEQ ID NO 36
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 36
ttaatatgtt taaatcccat ttctctggcc ttg 33

<210> SEQ ID NO 37
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 37
tttgatacag ccagtgttgg caccacttgg tgg 33

<210> SEQ ID NO 38
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 38
agttgcagtt caattgcttg taatgcttta ttc 33

<210> SEQ ID NO 39
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 39
ctatattgtg agttatatat tgtttctaac gtt 33

<210> SEQ ID NO 40
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 40
tagtggtgtg gcaggggttt ccggtgtctg gct 33

<210> SEQ ID NO 41
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 41
taacaattgc acttttatgt tttacattat gtc 33

<210> SEQ ID NO 42
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 42
ggagcactgt ccactgagtc tctgtgcaac aact 34

<210> SEQ ID NO 43
<211> LENGTH: 34

-continued

<212> TYPE: DNA
<213> ORGANISM: Artificial Sequence
<220> FEATURE:
<223> OTHER INFORMATION: Nucleic acid probe

<400> SEQUENCE: 43
tcctttgtgt gagctgttaa atgcagtgag gatt 34

<210> SEQ ID NO 44
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 44
ctatgggtgt agtgttacta ttacagttaa tccg 34

<210> SEQ ID NO 45
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 45
ctatgggtgt agtgttacta ttacagttaa tccg 34

<210> SEQ ID NO 46
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 46
caatgtacaa tgctttttaa atctatatct taaa 34

<210> SEQ ID NO 47
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 47
ctgtccaatg ccatgtagac gacactgcag tata 34

<210> SEQ ID NO 48
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 48
atactatgca taaatcccga aaagcaaagt catatac 37

<210> SEQ ID NO 49
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 49
atttatcaca tacagcatat ggattcccat ctctat 36

<210> SEQ ID NO 50
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 50
gtctatactc actaatttta gaataaaact ttaaac 36

<210> SEQ ID NO 51
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 51
gttctaatgt tgttccatac aaactataac aataat 36

<210> SEQ ID NO 52
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 52
ctaattaaca aatcacacaa cggtttgttg tattgct 37

<210> SEQ ID NO 53
<211> LENGTH: 40
<212> TYPE: DNA
<213> ORGANISM: Artificial Sequence
<220> FEATURE:
<223> OTHER INFORMATION: Nucleic acid probe

<400> SEQUENCE: 53
cctgtgggtc ctgaaacatt gcagttctct tttggtgcat 40

<210> SEQ ID NO 54
<211> LENGTH: 40
<212> TYPE: DNA
<213> ORGANISM: Artificial Sequence
<220> FEATURE:
<223> OTHER INFORMATION: Nucleic acid probe

<400> SEQUENCE: 54
tgtgctttgt acgcacaacc gaagcgtaga gtcacacttg 40

<210> SEQ ID NO 55
<211> LENGTH: 40
<212> TYPE: DNA
<213> ORGANISM: Artificial Sequence
<220> FEATURE:
<223> OTHER INFORMATION: Nucleic acid probe

<400> SEQUENCE: 55
ttatggtttc tgagaacaga tggggcacac aattcctagt 40

<210> SEQ ID NO 56
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 56
ttttcttcag gacacagtgg cttttgacag ttaatacac 39

<210> SEQ ID NO 57
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 57
atattatgga atctttgctt tttgtccaga tgtctttgc 39

<210> SEQ ID NO 58
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 58
ctgcaacaag acatacatcg accggtccac cgacccctt 39

<210> SEQ ID NO 59
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 59
atgattacag ctgggtttct ctacgtgttc ttgatgat 38

<210> SEQ ID NO 60
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 60
ctcctctgag ctgtcattta attgctcata ac 32

<210> SEQ ID NO 61
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 61
agtagagatc agttgtctct ggttgcaaat cta 33

<210> SEQ ID NO 62
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 62
tgcttgtcca gctggaccat ctatttcatc ctc 33

-continued

<210> SEQ ID NO 63
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 63
taaacgttcc gaaagggttt ccttcggtgt ctgcat 36

<210> SEQ ID NO 64
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 64
atactgtatt tggctgtcta tgtctttact gtcattt 37

<210> SEQ ID NO 65
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 65
aaagaatatt gcattttccc aacgtattag ttgcca 36

<210> SEQ ID NO 66
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 66
ggtggtttaa tgtctgtatg ccatgttccc ttgctgc 37

<210> SEQ ID NO 67
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 67
ctttactttt tgaaatgtta taggctggca ccacct 36

<210> SEQ ID NO 68
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 68
ccttgtaggg ccatttgcag ttcaatagct ttatgtg 37

<210> SEQ ID NO 69
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 69
gttctgtatt ccatagttcc tcgcatgtgt cttgcagtg 39

<210> SEQ ID NO 70
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 70
ttgtactgtt tggccacctt ttttaaagca gtgagtag 38

<210> SEQ ID NO 71
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 71
taggtcatac aattgtcttt gttgccatca aaatatac 38

<210> SEQ ID NO 72
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 72
cctgcatcag tcatataata cacactgtcc catgctaca 39

<210> SEQ ID NO 73
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 73
acgtgttgta cccttccttt acataataca atcccc 36

<210> SEQ ID NO 74
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 74
atatttttca cattcacttt taaattctat ataaa 35

<210> SEQ ID NO 75
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 75
ttcccaaaat gtacttccca cgtacctgtg ttccc 35

<210> SEQ ID NO 76

<211> LENGTH: 35
<212> TYPE: DNA
<213> ORGANISM: Artificial Sequence
<220> FEATURE:
<223> OTHER INFORMATION: Nucleic acid probe

<400> SEQUENCE: 76
tactgcacat agagtcatta caatcaatta catta 35

<210> SEQ ID NO 77
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 77
aacaagctga gtagcggata ccgtgtcgtc actgg 35

<210> SEQ ID NO 78
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 78
ctggaatacg gtgagggggt gtgctgtagc tgttt 35

<210> SEQ ID NO 79
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 79
ggccgtaggt ctttgcggtg cccacggaca cggtg 35

<210> SEQ ID NO 80
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 80
gtccacagtg tccaggtcgt gtagcagccg acgtct 36

<210> SEQ ID NO 81
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 81
tttgttgttg cctgtaggtg tagctgcacc gagaag 36

<210> SEQ ID NO 82
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 82
tataggcgta gtgttaccac tacagagttt ccgtct 36

<210> SEQ ID NO 83
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 83
acattttaaa ctgtttctgt caccttttaa atgtat 36

<210> SEQ ID NO 84
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 84
tagtggtcgc tatgttttcg caatctgtac cgtaa 35

<210> SEQ ID NO 85
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 85
gcacctgtcc aatgccaggt ggatgatata tctcta 36

<210> SEQ ID NO 86
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 86
tatgttacag tcagtattcc tgttttttca ttgcct 36

<210> SEQ ID NO 87
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 87
gtatttaaaa attttgttct ttgtgtttca ctatgg 36

<210> SEQ ID NO 88
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 88
gggtcgccgt gttggatcct caaagcgcgc cat 33

<210> SEQ ID NO 89
<211> LENGTH: 32
<212> TYPE: DNA

<213> ORGANISM: Artificial Sequence
<220> FEATURE:
<223> OTHER INFORMATION: Nucleic acid probe

<400> SEQUENCE: 89
ttcagttccg tgcacagatc aggtagcttg ta 32

<210> SEQ ID NO 90
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 90
tctgtaagtt ccaatactgt cttgcaat 28

<210> SEQ ID NO 91
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 91
caccacaaat aaatctttaa atgcaaattc aaatacc 37

<210> SEQ ID NO 92
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 92
atttatggca tgcagcatgg ggtatactgt ctctata 37

<210> SEQ ID NO 93
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 93
gtcttaattc tctaattcta gaataaaaat ctatac 36

<210> SEQ ID NO 94
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 94
ttttccaatg tgtctccata cacagagtct gaataat 37

<210> SEQ ID NO 95
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 95
ccttattaat aaattgtata acccagtgtt agttagt 37

<210> SEQ ID NO 96
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 96
tgctggattc aacggtttct ggcaccgcag gca 33

<210> SEQ ID NO 97
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 97
atcgtcgttt ttcattaagg tgtctaagtt tttc 34

<210> SEQ ID NO 98
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 98
ttggagtcgt tcctgtcgtg ctcggttgca gcacgaatg 39

<210> SEQ ID NO 99
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 99
atgcatactt aatattatac ttgtgtttct ctgcgtcg 38

<210> SEQ ID NO 100
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 100
taaatgcaat acaatgtctt gcaatgttgc cttaggtcc 39

<210> SEQ ID NO 101
<211> LENGTH: 40
<212> TYPE: DNA
<213> ORGANISM: Artificial Sequence
<220> FEATURE:
<223> OTHER INFORMATION: Nucleic acid probe

<400> SEQUENCE: 101
ttcatcgttt tcttcctctg agtcgcttaa ttgctcgtga 40

<210> SEQ ID NO 102
<211> LENGTH: 31
<212> TYPE: DNA
<213> ORGANISM: Artificial Sequence
<220> FEATURE:

-continued

<223> OTHER INFORMATION: Nucleic acid probe

<400> SEQUENCE: 102
caacattgtg tgacgttgtg gttcggctcg t 31

<210> SEQ ID NO 103
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 103
aattctggct tcacacttac aacacataca 30

<210> SEQ ID NO 104
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 104
ggtcgtctgc tgagctttct actactagct c 31

<210> SEQ ID NO 105
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 105
ttactgctgg gatgcacacc acggacacac aaagga 36

<210> SEQ ID NO 106
<211> LENGTH: 7905
<212> TYPE: DNA
<213> ORGANISM: Human papillomavirus type 16

<400> SEQUENCE: 106
actacaataa ttcatgtata aaactaaggg cgtaaccgaa atcggttgaa ccgaaaccgg 60
ttagtataaa agcagacatt ttatgcacca aaagagaact gcaatgtttc aggacccaca 120
ggagcgaccc agaaagttac cacagttatg cacagagctg caaacaacta tacatgatat 180
aatattagaa tgtgtgtact gcaagcaaca gttactgcga cgtgaggtat atgactttgc 240
ttttcgggat ttatgcatag tatatagaga tgggaatcca tatgctgtat gtgataaatg 300
tttaaagttt tattctaaaa ttagtgagta tagacattat tgttatagtt tgtatggaac 360
aacattagaa cagcaataca acaaaccgtt gtgtgatttg ttaattaggt gtattaactg 420
tcaaaagcca ctgtgtcctg aagaaaagca aagacatctg gacaaaaagc aaagattcca 480
taatataagg ggtcggtgga ccggtcgatg tatgtcttgt tgcagatcat caagaacacg 540
tagagaaacc cagctgtaat catgcatgga gatacaccta cattgcatga atatatgtta 600
gatttgcaac cagagacaac tgatctctac tgttatgagc aattaaatga cagctcagag 660
gaggaggatg aaatagatgg tccagctgga caagcagaac cggacagagc ccattacaat 720
attgtaacct tttgttgcaa gtgtgactct acgcttcggt tgtgcgtaca aagcacacac 780
gtagacattc gtactttgga agacctgtta atgggcacac taggaattgt gtgccccatc 840
tgttctcaga aaccataatc taccatggct gatcctgcag gtaccaatgg ggaagagggt 900

-continued

```
acgggatgta atggatggtt ttatgtagag gctgtagtgg aaaaaaaaac aggggatgct    960
atatcagatg acgagaacga aaatgacagt gatacaggtg aagatttggt agattttata   1020
gtaaatgata atgattattt aacacaggca gaaacagaga cagcacatgc gttgtttact   1080
gcacaggaag caaaacaaca tagagatgca gtacaggttc taaaacgaaa gtatttggta   1140
gtccacttag tgatattagt ggatgtgtag acaataatat tagtcctaga ttaaaagcta   1200
tatgtataga aaaacaaagt agagctgcaa aaaggagatt atttgaaagc gaagacagcg   1260
ggtatggcaa tactgaagtg gaaactcagc agatgttaca ggtagaaggg cgccatgaga   1320
ctgaaacacc atgtagtcag tatagtggtg gaagtggggg tggttgcagt cagtacagta   1380
gtggaagtgg gggagagggt gttagtgaaa gacacactat atgccaaaca ccacttacaa   1440
atattttaaa tgtactaaaa actagtaatg caaaggcagc aatgttagca aaatttaaag   1500
agttatacgg ggtgagtttt tcagaattag taagaccatt taaaagtaat aaatcaacgt   1560
gttgcgattg gtgtattgct gcatttggac ttacacccag tatagctgac agtataaaaa   1620
cactattaca acaatattgt ttatatttac acattcaaag tttagcatgt tcatggggaa   1680
tggttgtgtt actattagta agatataaat gtggaaaaaa tagagaaaca attgaaaaat   1740
tgctgtctaa actattatgt gtgtctccaa tgtgtatgat gatagagcct ccaaaattgc   1800
gtagtacagc agcagcatta tattggtata aaacaggtat atcaaatatt agtgaagtgt   1860
atggagacac gccagaatgg atacaaagac aaacagtatt acaacatagt tttaatgatt   1920
gtacatttga attatcacag atggtacaat gggcctacga taatgacata gtagacgata   1980
gtgaaattgc atataaatat gcacaattgg cagacactaa tagtaatgca agtgcctttc   2040
taaaaagtaa ttcacaggca aaaattgtaa aggattgtgc aacaatgtgt agacattata   2100
aacgagcaga aaaaaaacaa atgagtatga gtcaatggat aaaatataga tgtgataggg   2160
tagatgatgg aggtgattgg aagcaaattg ttatgttttt aaggtatcaa ggtgtagagt   2220
ttatgtcatt tttaactgca ttaaaaagat ttttgcaagg catacctaaa aaaaattgca   2280
tattactata tggtgcagct aacacaggta aatcattatt tggtatgagt ttaatgaaat   2340
ttctgcaagg gtctgtaata tgttttgtaa attctaaaag ccatttttgg ttacaaccat   2400
tagcagatgc caaaataggt atgttagatg atgctacagt gccctgttgg aactacatag   2460
atgacaattt aagaaatgca ttggatggaa atttagtttc tatggatgta aagcatagac   2520
cattggtaca actaaaatgc cctccattat taattacatc taacattaat gctggtacag   2580
attctaggtg gccttattta cataatagat tggtggtgtt tacatttcct aatgagtttc   2640
catttgacga aaacggaaat ccagtgtatg agcttaatga taagaactgg aaatcctttt   2700
tctcaaggac gtggtccaga ttaagtttgc acgaggacga ggacaaggaa aacgatggag   2760
actctttgcc aacgtttaaa tgtgtgtcag gacaaaatac taacacatta tgaaaatgat   2820
agtacagacc tacgtgacca tatagactat tggaaacaca tgcgcctaga atgtgctatt   2880
tattacaagg ccagagaaat gggatttaaa catattaacc accaagtggt gccaacactg   2940
gctgtatcaa agaataaagc attacaagca attgaactgc aactaacgtt agaaacaata   3000
tataactcac aatatagtaa tgaaaagtgg acattacaag acgttagcct tgaagtgtat   3060
ttaactgcac caacaggatg tataaaaaaa catggatata cagtggaagt gcagtttgat   3120
ggagacatat gcaatacaat gcattataca aactggacac atatatatat ttgtgaagaa   3180
gcatcagtaa ctgtggtaga gggtcaagtt gactattatg gtttatatta tgttcatgaa   3240
```

ggaatacgaa catattttgt gcagtttaaa gatgatgcag aaaaatatag taaaaataaa 3300
gtatgggaag ttcatgcggg tggtcaggta atattatgtc ctacatctgt gtttagcagc 3360
aacgaagtat cctctcctga aattattagg cagcacttgg ccaaccaccc cgccgcgacc 3420
cataccaaag ccgtcgcctt gggcaccgaa gaaacacaga cgactatcca gcgaccaaga 3480
tcagagccag acaccggaaa cccctgccac accactaagt tgttgcacag agactcagtg 3540
gacagtgctc caatcctcac tgcatttaac agctcacaca aaggacggat taactgtaat 3600
agtaacacta cacccatagt acatttaaaa ggtgatgcta atactttaaa atgtttaaga 3660
tatagattta aaaagcattg tacattgtat actgcagtgt cgtctacatg gcattggaca 3720
ggacataatg taaaacataa aagtgcaatt gttacactta catatgatag tgaatggcaa 3780
cgtgaccaat ttttgtctca agttaaaata ccaaaaacta ttacagtgtc tactggattt 3840
atgtctatat gacaaatctt gatactgcat ccacaacatt actggcgtgc tttttgcttt 3900
gcttttgtgt gcttttgtgt gtctgcctat taatacgtcc gctgcttttg tctgtgtcta 3960
catacacatc attaataata ttggtattac tattgtggat aacagcagcc tctgcgttta 4020
ggtgttttat tgtatatatt atatttgttt atataccatt atttttaata catacacatg 4080
cacgcttttt aattacataa tgtatatgta cataatgtaa ttgttacata taattgttgt 4140
ataccataac ttactatttt ttctttttta ttttcatata taattttttt ttttgtttgt 4200
ttgtttgttt tttaataaac tgttattact taacaatgcg acacaaacgt tctgcaaaac 4260
gcacaaaacg tgcatcggct acccaacttt ataaaacatg caaacaggca ggtacatgtc 4320
cacctgacat tatacctaag gttgaaggca aaactattgc tgaacaaata ttacaatatg 4380
gaagtatggg tgtatttttt ggtgggttag gaattggaac agggtcgggt acaggcggac 4440
gcactgggta tattccattg ggaacaaggc ctcccacagc tacagataca cttgctcctg 4500
taagaccccc tttaacagta gatcctgtgg gcccttctga tccttctata gtttctttag 4560
tggaagaaac tagttttatt gatgctggtg caccaacatc tgtaccttcc attcccccag 4620
atgtatcagg atttagtatt actacttcaa ctgataccac acctgctata ttagatatta 4680
ataatactgt tactactgtt actacacata ataatcccac tttcactgac ccatctgtat 4740
tgcagcctcc aacacctgca gaaactggag ggcattttac actttcatca tccactatta 4800
gtacacataa ttatgaagaa attcctatgg atacatttat tgttagcaca aaccctaaca 4860
cagtaactag tagcacaccc ataccagggt ctcgcccagt ggcacgccta ggattatata 4920
gtcgcacaac acaacaggtt aaagttgtag accctgcttt tgtaaccact cccactaaac 4980
ttattacata tgataatcct gcatatgaag gtatagatgt ggataataca ttatattttt 5040
ctagtaatga taatagtatt aatatagctc cagatcctga ctttttggat atagttgctt 5100
tacataggcc agcattaacc tctaggcgta ctggcattag gtacagtaga attggtaata 5160
aacaaacact acgtactcgt agtggaaaat ctataggtgc taaggtacat tattattatg 5220
atttaagtac tattgatcct gcagaagaaa tagaattaca aactataaca ccttctacat 5280
atactaccac ttcacatgca gcctcaccta cttctattaa taatggatta tatgatattt 5340
atgcagatga ctttattaca gatacttcta caaccccggt accatctgta ccctctacat 5400
ctttatcagg ttatattcct gcaaatacaa caattccttt tggtggtgca tacaatattc 5460
ctttagtatc aggtcctgat atacccatta atataactga ccaagctcct tcattaattc 5520
ctatagttcc agggtctcca caatatacaa ttattgctga tgcaggtgac ttttatttac 5580
atcctagtta ttacatgtta cgaaaacgac gtaaacgttt accatatttt ttttcagatg 5640
tctctttggc tgcctagtga ggccactgtc tacttgcctc ctgtcccagt atctaaggtt 5700
gtaagcacgg atgaatatgt tgcacgcaca aacatatatt atcatgcagg aacatccaga 5760
ctacttgcag ttggacatcc ctattttcct attaaaaaac ctaacaataa caaaatatta 5820
gttcctaaag tatcaggatt acaatacagg gtatttagaa tacatttacc tgaccccaat 5880
aagtttggtt ttcctgacac ctcattttat aatccagata cacagcggct ggtttgggcc 5940
tgtgtaggtg ttgaggtagg tcgtggtcag ccattaggtg tgggcattag tggccatcct 6000
ttattaaata aattggatga cacagaaaat gctagtgctt atgcagcaaa tgcaggtgtg 6060
gataatagag aatgtatatc tatggattac aaacaaacac aattgtgttt aattggttgc 6120
aaaccaccta taggggaaca ctggggcaaa ggatccccat gtaccaatgt tgcagtaaat 6180
ccaggtgatt gtccaccatt agagttaata aacacagtta ttcaggatgg tgatatggtt 6240
catactggct ttggtgctat ggactttact acattacagg ctaacaaaag tgaagttcca 6300
ctggatattt gtacatctat ttgcaaatat ccagattata ttaaaatggt gtcagaacca 6360
tatggcgaca gcttattttt ttatttacga agggaacaaa tgtttgttag acatttattt 6420
aatagggctg gtactgttgg tgaaaatgta ccagacgatt tatacattaa aggctctggg 6480
tctactgcaa atttagccag ttcaaattat tttcctacac ctagtggttc tatggttacc 6540
tctgatgccc aaatattcaa taaaccttat tggttacaac gagcacaggg ccacaataat 6600
ggcatttgtt ggggtaacca actatttgtt actgttgttg atactacacg cagtacaaat 6660
atgtcattat gtgctgccat atctacttca gaaactacat ataaaaatac taactttaag 6720
gagtacctac gacatgggga ggaatatgat ttacagttta tttttcaact gtgcaaaata 6780
accttaactg cagacgttat gacatacata cattctatga attccactat tttggaggac 6840
tggaattttg gtctacaacc tcccccagga ggcacactag aagatactta taggtttgta 6900
acccaggcaa ttgcttgtca aaaacataca cctccagcac ctaaagaaga tgatcccctt 6960
aaaaaataca ctttttggga agtaaattta aaggaaaagt tttctgcaga cctagatcag 7020
tttcctttag gacgcaaatt tttactacaa gcaggattga aggccaaacc aaaatttaca 7080
ttaggaaaac gaaaagctac acccaccacc tcatctacct ctacaactgc taaacgcaaa 7140
aaacgtaagc tgtaagtatt gtatgtatgt tgaattagtg ttgtttgttg tgtatatgtt 7200
tgtatgtgct tgtatgtgct tgtaaatatt aagttgtatg tgtgtttgta tgtatggtat 7260
aataaacacg tgtgtatgtg tttttaaatg cttgtgtaac tattgtgtca tgcaacataa 7320
ataaacttat tgtttcaaca cctactaatt gtgttgtggt tattcattgt atataaacta 7380
tatttgctac atcctgtttt tgttttatat atactatatt ttgtagcgcc aggcccattt 7440
tgtagcttca accgaattcg gttgcatgct ttttggcaca aaatgtgttt ttttaaatag 7500
ttctatgtca gcaactatgg tttaaacttg tacgtttcct gcttgccatg cgtgccaaat 7560
ccctgttttc ctgacctgca ctgcttgcca accattccat tgttttttac actgcactat 7620
gtgcaactac tgaatcacta tgtacattgt gtcatataaa ataaatcact atgcgccaac 7680
gccttacata ccgctgttag gcacatattt ttggcttgtt ttaactaacc taattgcata 7740
tttggcataa ggtttaaact tctaaggcca actaaatgtc accctagttc atacatgaac 7800
tgtgtaaagg ttagtcatac attgttcatt tgtaaaactg cacatgggtg tgtgcaaacc 7860
gattttgggt tacacattta caagcaactt atataataat actaa 7905

<210> SEQ ID NO 107

<211> LENGTH: 7857
<212> TYPE: DNA
<213> ORGANISM: Human papillomavirus type 18

<400> SEQUENCE: 107
attaatactt ttaacaattg tagtatataa aaaagggagt aaccgaaaac ggtcgggacc 60
gaaaacggtg tatataaaag atgtgagaaa cacaccacaa tactatggcg cgctttgagg 120
atccaacacg gcgaccctac aagctacctg atctgtgcac ggaactgaac acttcactgc 180
aagacataga aataacctgt gtatattgca agacagtatt ggaacttaca gaggtatttg 240
aatttgcatt taaagattta tttgtggtgt atagagacag tataccccat gctgcatgcc 300
ataaatgtat agatttttat tctagaatta gagaattaag acattattca gactctgtgt 360
atggagacac attggaaaaa ctaactaaca ctgggttata caatttatta ataaggtgcc 420
tgcggtgcca gaaaccgttg aatccagcag aaaaacttag acaccttaat gaaaaacgac 480
gatttcacaa catagctggg cactatagag gccagtgcca ttcgtgctgc aaccgagcac 540
gacaggaacg actccaacga cgcagagaaa cacaagtata atattaagta tgcatggacc 600
taaggcaaca ttgcaagaca ttgtattgca tttagagccc caaaatgaaa ttccggttga 660
ccttctatgt cacgagcaat taagcgactc agaggaagaa aacgatgaaa tagatggagt 720
taatcatcaa catttaccag cccgacgagc cgaaccacaa cgtcacacaa tgttgtgtat 780
gtgttgtaag tgtgaagcca gaattgagct agtagtagaa agctcagcag acgaccttcg 840
agcattccag cagctgtttc tgaacaccct gtcctttgtg tgtccgtggt gtgcatccca 900
gcagtaagca acaatggctg atccagaagg tacagacggg gagggcacgg gttgtaacgg 960
ctggttttat gtacaagcta ttgtagacaa aaaaacagga gatgtaatat cagatgacga 1020
ggacgaaaat gcaacagaca cagggtcgga tatggtagat tttattgata cacaaggaac 1080
attttgtgaa caggcagagc tagagacagc acaggcattg ttccatgcgc aggaggtcca 1140
caatgatgca caagtgttgc atgttttaaa acgaaagttt gcaggaggca gcacagaaaa 1200
cagtccatta ggggagcggc tggaggtgga tacagagtta agtccacggt tacaagaaat 1260
atctttaaat agtgggcaga aaaaggcaaa aaggcggctg tttacaatat cagatagtgg 1320
ctatggctgt tctgaagtgg aagcaacaca gattcaggta actacaaatg gcgaacatgg 1380
cggcaatgta tgtagtggcg gcagtacgga ggctatagac aacgggggca cagagggcaa 1440
caacagcagt gtagacggta caagtgacaa tagcaatata gaaaatgtaa atccacaatg 1500
taccatagca caattaaaag acttgttaaa agtaaacaat aaacaaggag ctatgttagc 1560
agtatttaaa gacacatatg ggctatcatt tacagattta gttagaaatt ttaaaagtga 1620
taaaaccacg tgtacagatt gggttacagc tatatttgga gtaaacccaa caatagcaga 1680
aggatttaaa acactaatac agccatttat attatatgcc catattcaat gtctagactg 1740
taaatgggga gtattaatat tagccctgtt gcgttacaaa tgtggtaaga gtagactaac 1800
agttgctaaa ggtttaagta cgttgttaca cgtacctgaa acttgtatgt taattcaacc 1860
accaaaattg cgaagtagtg ttgcagcact atattggtat agaacaggaa tatcaaatat 1920
tagtgaagta atgggagaca cacctgagtg gatacaaaga cttactatta tacaacatgg 1980
aatagatgat agcaattttg atttgtcaga aatggtacaa tgggcatttg ataatgagct 2040
gacagatgaa agcgatatgg catttgaata tgccttatta gcagacagca acagcaatgc 2100
agctgccttt ttaaaaagca attgccaagc taaatattta aaagattgtg ccacaatgtg 2160
caaacattat aggcgagccc aaaaacgaca aatgaatatg tcacagtgga tacgatttag 2220

-continued

```
atgttcaaaa atagatgaag ggggagattg gagaccaata gtgcaattcc tgcgatacca   2280
acaaatagag tttataacat ttttaggagc cttaaaatca tttttaaaag gaacccccaa   2340
aaaaaattgt ttagtatttt gtggaccagc aaatacagga aaatcatatt ttggaatgag   2400
ttttatacac tttatacaag gagcagtaat atcatttgtg aattccacta gtcatttttg   2460
gttggaaccg ttaacagata ctaaggtggc catgttagat gatgcaacga ccacgtgttg   2520
gacatacttt gatacctata tgagaaatgc gttagatggc aatccaataa gtattgatag   2580
aaagcacaaa ccattaatac aactaaaatg tcctccaata ctactaacca caaatataca   2640
tccagcaaag gataatagat ggccatattt agaaagtaga ataacagtat ttgaatttcc   2700
aaatgcattt ccatttgata aaaatggcaa tccagtatat gaaataaatg acaaaaattg   2760
gaaatgtttt tttgaaagga catggtccag attagatttg cacgaggaag aggaagatgc   2820
agacaccgaa ggaaaccctt tcggaacgtt taagttgcgt gcaggacaaa atcatagacc   2880
actatgaaaa tgacagtaaa gacatagaca gccaaataca gtattggcaa ctaatacgtt   2940
gggaaaatgc aatattcttt gcagcaaggg aacatggcat acagacatta aaccaccagg   3000
tggtgccagc ctataacatt tcaaaaagta aagcacataa agctattgaa ctgcaaatgg   3060
ccctacaagg ccttgcacaa agtcgataca aaaccgagga ttggacactg caagacacat   3120
gcgaggaact atggaataca gaacctactc actgctttaa aaaaggtggc caaacagtac   3180
aagtatattt tgatggcaac aaagacaatt gtatgaccta tgtagcatgg gacagtgtgt   3240
attatatgac tgatgcagga acatgggaca aaaccgctac ctgtgtaagt cacaggggat   3300
tgtattatgt aaaggaaggg tacaacacgt tttatataga atttaaaagt gaatgtgaaa   3360
aatatgggaa cacaggtacg tgggaagtac attttgggaa taatgtaatt gattgtaatg   3420
actctatgtg cagtaccagt gacgacacgg tatccgctac tcagcttgtt aaacagctac   3480
agcacacccc ctcaccgtat tccagcaccg tgtccgtggg caccgcaaag acctacggcc   3540
agacgtcggc tgctacacga cctggacact gtggactcgc ggagaagcag cattgtggac   3600
ctgtcaaccc acttctcggt gcagctacac ctacaggcaa caacaaaaga cggaaactct   3660
gtagtggtaa cactacgcct ataatacatt taaaaggtga cagaaacagt ttaaaatgtt   3720
tacggtacag attgcgaaaa catagcgacc actatagaga tatatcatcc acctggcatt   3780
ggacaggtgc aggcaatgaa aaaacaggaa tactgactgt aacataccat agtgaaacac   3840
aaagaacaaa atttttaaat actgttgcaa ttccagatag tgtacaaata ttggtgggat   3900
acatgacaat gtaatacata tgctgtagta ccaatatgtt atcacttatt tttttatttt   3960
gcttttgtgt atgcatgtat gtgtgctgcc atgtcccgct tttgccatct gtctgtatgt   4020
gtgcgtatgc atgggtattg gtatttgtgt atattgtggt aataacgtcc cctgccacag   4080
cattcacagt atatgtattt tgttttttat tgcccatgtt actattgcat atacatgcta   4140
tattgtcttt acagtaattg tataggttgt tttatacagt gtattgtaca ttgtatattt   4200
tgttttatac cttttatgct tttgtatttt ttgtaataaa agtatggtat cccaccgtgc   4260
cgcacgacgc aaacgggctt cggtaactga cttatataaa acatgtaaac aatctggtac   4320
atgtccacct gatgttgttc ctaaggtgga gggcaccacg ttagcagata aaatattgca   4380
atggtcaagc cttggtatat ttttgggtgg acttggcata ggtactggca gtggtacagg   4440
gggtcgtaca gggtacattc cattgggtgg gcgttccaat acagtggtgg atgttggtcc   4500
tacacgtccc ccagtggtta ttgaacctgt gggccccaca gacccatcta ttgttacatt   4560
```

-continued aatagaggac tccagtgtgg ttacatcagg tgcacctagg cctacgttta ctggcacgtc 4620
tgggtttgat ataacatctg cgggtacaac tacacctgcg gttttggata tcacaccttc 4680
gtctacctct gtgtctattt ccacaaccaa ttttaccaat cctgcatttt ctgatccgtc 4740
cattattgaa gttccacaaa ctggggaggt ggcaggtaat gtatttgttg gtacccctac 4800
atctggaaca catgggtatg aggaaatacc tttacaaaca tttgcttctt ctggtacggg 4860
ggaggaaccc attagtagta ccccattgcc tactgtgcgg cgtgtagcag gtccccgcct 4920
ttacagtagg gcctaccaac aagtgtcagt ggctaaccct gagtttctta cacgtccatc 4980
ctctttaatt acatatgaca acccggcctt tgagcctgtg gacactacat taacatttga 5040
tcctcgtagt gatgttcctg attcagattt tatggatatt atccgtctac ataggcctgc 5100
tttaacatcc aggcgtggga ctgttcgctt tagtagatta ggtcaacggg caactatgtt 5160
tacccgcagc ggtacacaaa taggtgctag ggttcacttt tatcatgata taagtcctat 5220
tgcaccttcc ccagaatata ttgaactgca gcctttagta tctgccacgg aggacaatga 5280
cttgtttgat atatatgcag atgacatgga ccctgcagtg cctgtaccat cgcgttctac 5340
tacctccttt gcattttta aatattcgcc cactatatct tctgcctctt cctatagtaa 5400
tgtaacggtc cctttaacct cctcttggga tgtgcctgta tacacgggtc ctgatattac 5460
attaccatct actacctctg tatggcccat tgtatcaccc acggcccctg cctctacaca 5520
gtatattggt atacatggta cacattatta tttgtggcca ttatattatt ttattcctaa 5580
gaaacgtaaa cgtgttccct attttttgc agatggcttt gtggcggcct agtgacaata 5640
ccgtatatct tccacctcct tctgtggcaa gagttgtaaa taccgatgat tatgtgactc 5700
ccacaagcat attttatcat gctggcagct ctagattatt aactgttggt aatccatatt 5760
ttagggttcc tgcaggtggt ggcaataagc aggatattcc taaggtttct gcataccaat 5820
atagagtatt tagggtgcag ttacctgacc caaataaatt tggtttacct gatactagta 5880
tttataatcc tgaaacacaa cgtttagtgt gggcctgtgc tggagtggaa attggccgtg 5940
gtcagccttt aggtgttggc cttagtgggc atccatttta taataaatta gatgacactg 6000
aaagttccca tgccgccacg tctaatgttt ctgaggacgt tagggacaat gtgtctgtag 6060
attataagca gacacagtta tgtattttgg gctgtgcccc tgctattggg gaacactggg 6120
ctaaaggcac tgcttgtaaa tcgcgtcctt tatcacaggg cgattgcccc cctttagaac 6180
ttaaaaacac agttttggaa gatggtgata tggtagatac tggatatggt gccatggact 6240
ttagtacatt gcaagatact aaatgtgagg taccattgga tatttgtcag tctatttgta 6300
aatatcctga ttatttacaa atgtctgcag atccttatgg ggattccatg tttttttgct 6360
tacggcgtga gcagcttttt gctaggcatt tttggaatag agcaggtact atgggtgaca 6420
ctgtgcctca atccttatat attaaaggca caggtatgcc tgcttcacct ggcagctgtg 6480
tgtattctcc ctctccaagt ggctctattg ttacctctga ctcccagttg tttaataaac 6540
catattggtt acataaggca cagggtcata acaatggtgt ttgctggcat aatcaattat 6600
ttgttactgt ggtagatacc actcccagta ccaatttaac aatatgtgct tctacacagt 6660
ctcctgtacc tgggcaatat gatgctacca aatttaagca gtatagcaga catgttgagg 6720
aatatgattt gcagtttatt tttcagttgt gtactattac tttaactgca gatgttatgt 6780
cctatattca tagtatgaat agcagtattt tagaggattg gaactttggt gttccccccc 6840
ccccaactac tagtttggtg gatacatatc gttttgtaca atctgttgct attacctgtc 6900
aaaaggatgc tgcaccggct gaaaataagg atccctatga taagttaaag ttttggaatg 6960

```
tggatttaaa ggaaaagttt tctttagact tagatcaata tccccttgga cgtaaatttt   7020

tggttcaggc tggattgcgt cgcaagccca ccataggccc tcgcaaacgt tctgctccat   7080

ctgccactac gtcttctaaa cctgccaagc gtgtgcgtgt acgtgccagg aagtaatatg   7140

tgtgtgtgta tatatatata catctattgt tgtgtttgta tgtcctgtgt ttgtgtttgt   7200

tgtatgattg cattgtatgg tatgtatggt tgttgttgta tgttgtatgt tactatattt   7260

gttggtatgt ggcattaaat aaaatatgtt ttgtggttct gtgtgttatg tggttgcgcc   7320

ctagtgagta acaactgtat ttgtgtttgt ggtatgggtg ttgcttgttg ggctatatat   7380

tgtcctgtat ttcaagttat aaaactgcac accttacagc atccatttta tcctacaatc   7440

ctccattttg ctgtgcaacc gatttcggtt gcctttggct tatgtctgtg gttttctgca   7500

caatacagta cgctggcact attgcaaact ttaatctttt gggcactgct cctacatatt   7560

ttgaacaatt ggcgcgcctc tttggcgcat ataaggcgca cctggtatta gtcattttcc   7620

tgtccaggtg cgctacaaca attgcttgca taactatatc cactccctaa gtaataaaac   7680

tgcttttagg cacatatttt agtttgtttt tacttaagct aattgcatac ttggcttgta   7740

caactacttt catgtccaac attctgtcta cccttaacat gaactataat atgactaagc   7800

tgtgcataca tagtttatgc aaccgaaata ggttgggcag cacatactat acttttc      7857
```

<210> SEQ ID NO 108
<211> LENGTH: 23
<212> TYPE: DNA
<213> ORGANISM: Artificial Sequence
<220> FEATURE:
<223> OTHER INFORMATION: Nucleic acid primer

<400> SEQUENCE: 108
gcaccaaaag agaactgcaa tgt 23

<210> SEQ ID NO 109
<211> LENGTH: 24
<212> TYPE: DNA
<213> ORGANISM: Artificial Sequence
<220> FEATURE:
<223> OTHER INFORMATION: Nucleic acid primer

<400> SEQUENCE: 109
catatacctc acgtcgcagt aact 24

<210> SEQ ID NO 110
<211> LENGTH: 24
<212> TYPE: DNA
<213> ORGANISM: Artificial Sequence
<220> FEATURE:
<223> OTHER INFORMATION: Nucleic acid primer

<400> SEQUENCE: 110
caggacccac aggagcgacc caga 24

<210> SEQ ID NO 111
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 111
ggtcgctcct gtgggtcctg aaacattgca gtt 33

<210> SEQ ID NO 112
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 112
cattctaata ttatatcatg tatagttg 28

<210> SEQ ID NO 113
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 113
tcacgtcgca gtaactgttg cttgcagtac ac 32

<210> SEQ ID NO 114
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 114
tactatgcat aaatcccgaa aagcaaagtc atatacc 37

<210> SEQ ID NO 115
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 115
tttatcacat acagcatatg gattcccatc tctata 36

<210> SEQ ID NO 116
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 116
gtctatactc actaatttta gaataaaact ttaaaca 37

<210> SEQ ID NO 117
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 117
ttcatgcaat gtaggtgtat ctccatgcat gatta 35

<210> SEQ ID NO 118
<211> LENGTH: 43
<212> TYPE: DNA
<213> ORGANISM: Artificial Sequence
<220> FEATURE:
<223> OTHER INFORMATION: Nucleic acid probe

<400> SEQUENCE: 118
atcctcctcc tctgagctgt catttaattg ctcataacag tag 43

<210> SEQ ID NO 119
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 119
gttctgcttg tccagctgga ccatctattt c 31

<210> SEQ ID NO 120
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 120
aaggttacaa tattgtaatg ggctctgtcc g 31

<210> SEQ ID NO 121
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 121
caaccgaagc gtagagtcac acttgcaaca a 31

<210> SEQ ID NO 122
<211> LENGTH: 41
<212> TYPE: DNA
<213> ORGANISM: Artificial Sequence
<220> FEATURE:
<223> OTHER INFORMATION: Nucleic acid probe

<400> SEQUENCE: 122
tggggcacac aattcctagt gtgcccatta acaggtcttc c 41

<210> SEQ ID NO 123
<211> LENGTH: 42
<212> TYPE: DNA
<213> ORGANISM: Artificial Sequence
<220> FEATURE:
<223> OTHER INFORMATION: Nucleic acid probe

<400> SEQUENCE: 123
ctgcaggatc agccatggta gattatggtt tctgagaaca ga 42

<210> SEQ ID NO 124
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 124
tccattacat cccgtaccct cttccccatt ggtac 35

<210> SEQ ID NO 125

<211> LENGTH: 35
<212> TYPE: DNA
<213> ORGANISM: Artificial Sequence
<220> FEATURE:
<223> OTHER INFORMATION: Nucleic acid probe

<400> SEQUENCE: 125
gttttttttt ccactacagc ctctacataa aacca 35

<210> SEQ ID NO 126
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 126
cattttcgtt ctcgtcatct gatatagcat cccct 35

<210> SEQ ID NO 127
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 127
tataaaatct accaaatctt cacctgtatc actgt 35

<210> SEQ ID NO 128
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 128
gtttctgcct gtgttaaata atcattatca tttac 35

<210> SEQ ID NO 129
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 129
cttcctgtgc agtaaacaac gcatgtgctg tctct 35

<210> SEQ ID NO 130
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 130
ttttagaacc tgtactgcat ctctatgttg ttttg 35

<210> SEQ ID NO 131
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 131
actaatatca ctaagtggac taccaaatac tttcg 35

<210> SEQ ID NO 132
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 132
tttaatctag gactaatatt attgtctaca catcc 35

<210> SEQ ID NO 133
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 133
ttgcagctct actttgtttt tctatacata tagct 35

<210> SEQ ID NO 134
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 134
atacccgctg tcttcgcttt caaataatct ccttt 35

<210> SEQ ID NO 135
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 135
tgtaacatct gctgagtttc cacttcagta ttgcc 35

<210> SEQ ID NO 136
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 136
tacatggtgt ttcagtctca tggcgccctt ctacc 35

<210> SEQ ID NO 137
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 137
actgcaacca cccccacttc caccactata ctgac 35

<210> SEQ ID NO 138
<211> LENGTH: 35
<212> TYPE: DNA

<213> ORGANISM: Artificial Sequence
<220> FEATURE:
<223> OTHER INFORMATION: Nucleic acid probe

<400> SEQUENCE: 138
ctaacaccct ctcccccact tccactactg tactg 35

<210> SEQ ID NO 139
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 139
ttgtaagtgg tgtttggcat atagtgtgtc tttca 35

<210> SEQ ID NO 140
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 140
ctttgcatta ctagttttta gtacatttaa aatat 35

<210> SEQ ID NO 141
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 141
ccgtataact ctttaaattt tgctaacatt gctgc 35

<210> SEQ ID NO 142
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 142
ttttaaatgg tcttactaat tctgaaaaac tcacc 35

<210> SEQ ID NO 143
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 143
agcaatacac caatcgcaac acgttgattt attac 35

<210> SEQ ID NO 144
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 144
atactgtcag ctatactggg tgtaagtcca aatgc 35

<210> SEQ ID NO 145
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 145
gtaaatataa acaatattgt tgtaatagtg ttttt 35

<210> SEQ ID NO 146
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 146
aaccattccc catgaacatg ctaaactttg aatgt 35

<210> SEQ ID NO 147
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 147
tctatttttt ccacatttat atcttactaa tagtaacac 39

<210> SEQ ID NO 148
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 148
cacacataat agtttagaca gcaatttttc aattgtttc 39

<210> SEQ ID NO 149
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 149
acgcaatttt ggaggctcta tcatcataca cattggaga 39

<210> SEQ ID NO 150
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 150
gcgtgtctcc atacacttca ctaatatttg atata 35

<210> SEQ ID NO 151
<211> LENGTH: 35
<212> TYPE: DNA
<213> ORGANISM: Artificial Sequence
<220> FEATURE:

<223> OTHER INFORMATION: Nucleic acid probe

<400> SEQUENCE: 151
atgttgtaat actgtttgtc tttgtatcca ttctg 35

<210> SEQ ID NO 152
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 152
atctgtgata attcaaatgt acaatcatta aaact 35

<210> SEQ ID NO 153
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 153
cgtctactat gtcattatcg taggcccatt gtacc 35

<210> SEQ ID NO 154
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 154
tgccaattgt gcatatttat atgcaatttc actat 35

<210> SEQ ID NO 155
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 155
ctttttagaa aggcacttgc attactatta gtgtc 35

<210> SEQ ID NO 156
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 156
ttgcacaatc ctttacaatt tttgcctgtg aatta 35

<210> SEQ ID NO 157
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 157 tttttttct gctcgtttat aatgtctaca cattg 35

<210> SEQ ID NO 158
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 158
catctatatt ttatccattg actcatactc atttg 35

<210> SEQ ID NO 159
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 159
tttgcttcca atcacctcca tcatctaccc tatca 35

<210> SEQ ID NO 160
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 160
aaactctaca ccttgatacc ttaaaaacat aacaa 35

<210> SEQ ID NO 161
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 161
tgcaaaaatc tttttaatgc agttaaaaat gacat 35

<210> SEQ ID NO 162
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 162
catatagtaa tatgcaattt tttttaggta tgcct 35

<210> SEQ ID NO 163
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 163
cataccaaat aatgatttac ctgtgttagc tgcac 35

<210> SEQ ID NO 164
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 164
catattacag acccttgcag aaatttcatt aaact 35

<210> SEQ ID NO 165
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 165
gttgtaacca aaaatggctt ttagaattta caaaa 35

<210> SEQ ID NO 166
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 166
atcatctaac atacctattt tggcatctgc taatg 35

<210> SEQ ID NO 167
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 167
ttgtcatcta tgtagttcca acagggcact gtagc 35

<210> SEQ ID NO 168
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 168
tagaaactaa atttccatcc aatgcatttc ttaaa 35

<210> SEQ ID NO 169
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 169
ttttagttgt accaatggtc tatgctttac atcca 35

<210> SEQ ID NO 170
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 170
gcattaatgt tagatgtaat taataatgga gggca 35

<210> SEQ ID NO 171
<211> LENGTH: 35

<212> TYPE: DNA
<213> ORGANISM: Artificial Sequence
<220> FEATURE:
<223> OTHER INFORMATION: Nucleic acid probe

<400> SEQUENCE: 171
tattatgtaa ataaggccac ctagaatctg tacca 35

<210> SEQ ID NO 172
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 172
tggaaactca ttaggaaatg taaacaccac caatc 35

<210> SEQ ID NO 173
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 173
ttaagctcat acactggatt tccgttttcg tcaaa 35

<210> SEQ ID NO 174
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 174
tccttgagaa aaaggatttc cagttcttat ca 32

<210> SEQ ID NO 175
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 175
tcctcgtcct cgtgcaaact taatctggac cacg 34

<210> SEQ ID NO 176
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 176
aaacgttggc aaagagtctc catcgttttc cttg 34

<210> SEQ ID NO 177
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 177
taatgtgtta gtattttgtc ctgacacaca ttt 33

<210> SEQ ID NO 178
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 178
tatatggtca cgtaggtctg tactatcatt ttca 34

<210> SEQ ID NO 179
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 179
tagcacattc taggcgcatg tgtttccaat agtc 34

<210> SEQ ID NO 180
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 180
tgtttaaatc ccatttctct ggccttgtaa taaa 34

<210> SEQ ID NO 181
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 181
acagccagtg ttggcaccac ttggtggtta ata 33

<210> SEQ ID NO 182
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 182
cagttcaatt gcttgtaatg ctttattctt tgat 34

<210> SEQ ID NO 183
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 183
attgtgagtt atatattgtt tctaacgtta gttg 34

<210> SEQ ID NO 184
<211> LENGTH: 40
<212> TYPE: DNA
<213> ORGANISM: Artificial Sequence -continued
<220> FEATURE:
<223> OTHER INFORMATION: Nucleic acid probe

<400> SEQUENCE: 184
tttttataca tcctgttggt gcagttaaat acacttcaag 40

<210> SEQ ID NO 185
<211> LENGTH: 41
<212> TYPE: DNA
<213> ORGANISM: Artificial Sequence
<220> FEATURE:
<223> OTHER INFORMATION: Nucleic acid probe

<400> SEQUENCE: 185
tatgtctcca tcaaactgca cttccactgt atatccatgt t 41

<210> SEQ ID NO 186
<211> LENGTH: 40
<212> TYPE: DNA
<213> ORGANISM: Artificial Sequence
<220> FEATURE:
<223> OTHER INFORMATION: Nucleic acid probe

<400> SEQUENCE: 186
tatatatatg tgtccagttt gtataatgca ttgtattgca 40

<210> SEQ ID NO 187
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 187
accctctacc acagttactg atgcttcttc acaaa 35

<210> SEQ ID NO 188
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 188
atgaacataa tataaaccat aatagtcaac ttg 33

<210> SEQ ID NO 189
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 189
ctttattttt actatatttt tctgcatca 29

<210> SEQ ID NO 190
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 190
acctgaccac ccgcatgaac ttcccata 28

<210> SEQ ID NO 191
<211> LENGTH: 29
<212> TYPE: DNA
<213> ORGANISM: Artificial Sequence
<220> FEATURE:
<223> OTHER INFORMATION: Nucleic acid probe

<400> SEQUENCE: 191
tgctaaacac agatgtagga cataatatt 29

<210> SEQ ID NO 192
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 192
gtatgggtcg cggcggggtg gttggccaag tg 32

<210> SEQ ID NO 193
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 193
tctgtgtttc ttcggtgccc aaggcgacgg ctttg 35

<210> SEQ ID NO 194
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 194
gtgtctggct ctgatcttgg tcgctggata gtcg 34

<210> SEQ ID NO 195
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 195
gtgcaacaac ttagtggtgt ggcaggggtt tccg 34

<210> SEQ ID NO 196
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 196
cagtgaggat tggagcactg tccactgagt ctc 33

<210> SEQ ID NO 197
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 197
tacagttaat ccgtcctttg tgtgagctgt taaatg 36

<210> SEQ ID NO 198
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 198
ccttttaaat gtactatggg tgtagtgtta ctat 34

<210> SEQ ID NO 199
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 199
atctatatct taaacatttt aaagtattag catca 35

<210> SEQ ID NO 200
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 200
acgacactgc agtatacaat gtacaatgct ttttaa 36

<210> SEQ ID NO 201
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 201
atgttttaca ttatgtcctg tccaatgcca tgtag 35

<210> SEQ ID NO 202
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 202
ttcactatca tatgtaagtg taacaattgc actttt 36

<210> SEQ ID NO 203
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 203
ggtattttaa cttgagacaa aaattggtca cgttgcca 38

<210> SEQ ID NO 204

<211> LENGTH: 38
<212> TYPE: DNA
<213> ORGANISM: Artificial Sequence
<220> FEATURE:
<223> OTHER INFORMATION: Nucleic acid probe

<400> SEQUENCE: 204
atatagacat aaatccagta gacactgtaa tagttttt 38

<210> SEQ ID NO 205
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 205
cacaaaagca cacaaagcaa agcaaaaagc acg 33

<210> SEQ ID NO 206
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 206
agacaaaagc agcggacgta ttaataggca gaca 34

<210> SEQ ID NO 207
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 207
taataccaat attattaatg atgtgtatgt agacac 36

<210> SEQ ID NO 208
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 208
cacctaaacg cagaggctgc tgttatccac aatag 35

<210> SEQ ID NO 209
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 209
aatggtatat aaacaaatat aatatataca ataaaa 36

<210> SEQ ID NO 210
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 210
taattaaaaa gcgtgcatgt gtatgtatta aaaat 35

<210> SEQ ID NO 211
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 211
atatgtaaca attacattat gtacatatac attatg 36

<210> SEQ ID NO 212
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 212
aaagaaaaaa tagtaagtta tggtatacaa caatt 35

<210> SEQ ID NO 213
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 213
aaacaaacaa aaaaaaaaat tatatatgaa aataaa 36

<210> SEQ ID NO 214
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 214
attgttaagt aataacagtt tattaaaaaa caaac 35

<210> SEQ ID NO 215
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 215
cacgttttgt gcgttttgca gaacgtttgt gtcgc 35

<210> SEQ ID NO 216
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 216
ctgtttgcat gttttataaa gttgggtagc cgatg 35

<210> SEQ ID NO 217
<211> LENGTH: 35
<212> TYPE: DNA

<213> ORGANISM: Artificial Sequence
<220> FEATURE:
<223> OTHER INFORMATION: Nucleic acid probe

<400> SEQUENCE: 217
accttaggta taatgtcagg tggacatgta cctgc 35

<210> SEQ ID NO 218
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 218
attgtaatat ttgttcagca atagttttgc cttca 35

<210> SEQ ID NO 219
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 219
tcctaaccca ccaaaaaata cacccatact tccat 35

<210> SEQ ID NO 220
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 220
ccagtgcgtc cgcctgtacc cgaccctgtt ccaat 35

<210> SEQ ID NO 221
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 221
tagctgtggg aggccttgtt cccaatggaa tatac 35

<210> SEQ ID NO 222
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 222
tgttaaaggg ggtcttacag gagcaagtgt atctg 35

<210> SEQ ID NO 223
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 223
actatagaag gatcagaagg gcccacagga tctac 35

<210> SEQ ID NO 224
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 224
cagcatcaat aaaactagtt tcttccacta aagaa 35

<210> SEQ ID NO 225
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 225
atctggggga atggaaggta cagatgttgg tgcac 35

<210> SEQ ID NO 226
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 226
gtatcagttg aagtagtaat actaaatcct gatac 35

<210> SEQ ID NO 227
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 227
taacagtatt attaatatct aatatagcag gtgtg 35

<210> SEQ ID NO 228
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 228
agtgaaagtg ggattattat gtgtagtaac agtag 35

<210> SEQ ID NO 229
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 229
ttctgcaggt gttggaggct gcaatacaga tgggtc 36

<210> SEQ ID NO 230
<211> LENGTH: 36
<212> TYPE: DNA
<213> ORGANISM: Artificial Sequence
<220> FEATURE:

<223> OTHER INFORMATION: Nucleic acid probe

<400> SEQUENCE: 230
aatagtggat gatgaaagtg taaaatgccc tccagt 36

<210> SEQ ID NO 231
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 231
tgtatccata ggaatttctt cataattatg tgtact 36

<210> SEQ ID NO 232
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 232
actagttact gtgttagggt ttgtgctaac aataaa 36

<210> SEQ ID NO 233
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 233
gcgtgccact gggcgagacc ctggtatggg tgtgct 36

<210> SEQ ID NO 234
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 234
agtgggagtg gttacaaaag cagggtctac aact 34

<210> SEQ ID NO 235
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 235
ccttcatatg caggattatc atatgtaata agttt 35

<210> SEQ ID NO 236
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 236
tactagaaaa atataatgta ttatccacat ctata 35

<210> SEQ ID NO 237
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 237
gtcaggatct ggagctatat taatactatt atcat 35

<210> SEQ ID NO 238
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 238
aatgctggcc tatgtaaagc aactatatcc aaaaa 35

<210> SEQ ID NO 239
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 239
ttctactgta cctaatgcca gtacgcctag aggtt 35

<210> SEQ ID NO 240
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 240
tccactacga gtacgtagtg tttgtttatt accaa 35

<210> SEQ ID NO 241
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 241
tcataataat aatgtacctt agcacctata gattt 35

<210> SEQ ID NO 242
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 242
attctatttc ttctgcagga tcaatagtac ttaaa 35

<210> SEQ ID NO 243
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 243
agtggtagta tatgtagaag gtgttatagt ttgta 35

<210> SEQ ID NO 244
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 244
ccattattaa tagaagtagg tgaggctgca tgtga 35

<210> SEQ ID NO 245
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 245
ctgtaataaa gtcatctgca taaatatcat ataat 35

<210> SEQ ID NO 246
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 246
agagggtaca gatggtaccg gggttgtaga agtat 35

<210> SEQ ID NO 247
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 247
gttgtatttg caggaatata acctgataaa gatgt 35

<210> SEQ ID NO 248
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 248
ctaaaggaat attgtatgca ccaccaaaag gaatt 35

<210> SEQ ID NO 249
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 249
gtcagttata ttaatgggta tatcaggacc tgata 35

<210> SEQ ID NO 250
<211> LENGTH: 35

<212> TYPE: DNA
<213> ORGANISM: Artificial Sequence
<220> FEATURE:
<223> OTHER INFORMATION: Nucleic acid probe

<400> SEQUENCE: 250
gaccctggaa ctataggaat taatgaagga gcttg 35

<210> SEQ ID NO 251
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 251
agtcacctgc atcagcaata attgtatatt gtgga 35

<210> SEQ ID NO 252
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 252
tttcgtaaca tgtaataact aggatgtaaa taaa 34

<210> SEQ ID NO 253
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 253
atctgaaaaa aaatatggta aacgtttacg tcgt 34

<210> SEQ ID NO 254
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 254
caagtagaca gtggcctcac taggcagcca aagagac 37

<210> SEQ ID NO 255
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 255
tcatccgtgc ttacaacctt agatactggg acaggagg 38

<210> SEQ ID NO 256
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 256

-continued tcctgcatga taatatatgt ttgtgcgtgc aacatat 37

<210> SEQ ID NO 257
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 257
ggaaaatagg gatgtccaac tgcaagtagt ctggatgt 38

<210> SEQ ID NO 258
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 258
gaactaatat tttgttattg ttaggttttt taata 35

<210> SEQ ID NO 259
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 259
ctaaataccc tgtattgtaa tcctgatact ttag 34

<210> SEQ ID NO 260
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 260
aaaaccaaac ttattggggt caggtaaatg tatt 34

<210> SEQ ID NO 261
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 261
cgctgtgtat ctggattata aaatgaggtg tcagg 35

<210> SEQ ID NO 262
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 262
acctacctca acacctacac aggcccaaac cagc 34

<210> SEQ ID NO 263
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 263
ggccactaat gcccacacct aatggctgac cacg 34

<210> SEQ ID NO 264
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 264
attttctgtg tcatccaatt tatttaataa aggat 35

<210> SEQ ID NO 265
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 265
tatccacacc tgcatttgct gcataagcac tagc 34

<210> SEQ ID NO 266
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 266
gtttgtttgt aatccataga tatacattct ctat 34

<210> SEQ ID NO 267
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 267
ctataggtgg tttgcaacca attaaacaca attgt 35

<210> SEQ ID NO 268
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 268
ttggtacatg gggatccttt gccccagtgt tccc 34

<210> SEQ ID NO 269
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 269
taatggtgga caatcacctg gatttactgc aaca 34

-continued

<210> SEQ ID NO 270
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 270
atatcaccat cctgaataac tgtgtttatt aactc 35

<210> SEQ ID NO 271
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 271
agtaaagtcc atagcaccaa agccagtatg aacc 34

<210> SEQ ID NO 272
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 272
ccagtggaac ttcacttttg ttagcctgta atgt 34

<210> SEQ ID NO 273
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 273
ataatctgga tatttgcaaa tagatgtaca aatat 35

<210> SEQ ID NO 274
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 274
agctgtcgcc atatggttct gacaccattt taat 34

<210> SEQ ID NO 275
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 275
acaaacattt gttcccttcg taaataaaaa aata 34

<210> SEQ ID NO 276
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 276
caccaacagt accagcccta ttaaataaat gtcta 35

<210> SEQ ID NO 277
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 277
gagcctttaa tgtataaatc gtctggtaca tttt 34

<210> SEQ ID NO 278
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 278
catcagaggt aaccatagaa ccactaggtg taggaa 36

<210> SEQ ID NO 279
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 279
ctcgttgtaa ccaataaggt ttattgaata tttggg 36

<210> SEQ ID NO 280
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 280
ggttacccca acaaatgcca ttattgtggc cctgtg 36

<210> SEQ ID NO 281
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 281
actgcgtgta gtatcaacaa cagtaacaaa tagtt 35

<210> SEQ ID NO 282
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 282
tgaagtagat atggcagcac ataatgacat atttgt 36

<210> SEQ ID NO 283

<211> LENGTH: 36
<212> TYPE: DNA
<213> ORGANISM: Artificial Sequence
<220> FEATURE:
<223> OTHER INFORMATION: Nucleic acid probe

<400> SEQUENCE: 283
gtactcctta aagttagtat ttttatatgt agtttc 36

<210> SEQ ID NO 284
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 284
aataaactgt aaatcatatt cctccccatg tcgtag 36

<210> SEQ ID NO 285
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 285
acgtctgcag ttaaggttat tttgcacagt tgaaa 35

<210> SEQ ID NO 286
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 286
aaaatagtgg aattcataga atgtatgtat gtcata 36

<210> SEQ ID NO 287
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 287
cctgggggag gttgtagacc aaaattccag tcctcc 36

<210> SEQ ID NO 288
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 288
gggttacaaa cctataagta tcttctagtg tgcct 35

<210> SEQ ID NO 289
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 289
gtgctggagg tgtatgtttt tgacaagcaa ttgcct 36

<210> SEQ ID NO 290
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 290
aaaaagtgta ttttttaagg ggatcatctt ctttag 36

<210> SEQ ID NO 291
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 291
ggtctgcaga aaacttttcc tttaaattta cttccc 36

<210> SEQ ID NO 292
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 292
gtagtaaaaa tttgcgtcct aaaggaaact gatcta 36

<210> SEQ ID NO 293
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 293
taatgtaaat tttggtttgg ccttcaatcc tgctt 35

<210> SEQ ID NO 294
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 294
agatgaggtg gtgggtgtag cttttcgttt tcc 33

<210> SEQ ID NO 295
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 295
cacatacaac ttaatattta caagc 25

<210> SEQ ID NO 296
<211> LENGTH: 33
<212> TYPE: DNA

<213> ORGANISM: Artificial Sequence
<220> FEATURE:
<223> OTHER INFORMATION: Nucleic acid probe

<400> SEQUENCE: 296
cttacgtttt ttgcgtttag cagttgtaga ggt 33

<210> SEQ ID NO 297
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 297
aacactaatt caacatacat acaatactta cag 33

<210> SEQ ID NO 298
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 298
acatacaagc acatacaaac atatacacaa caaac 35

<210> SEQ ID NO 299
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 299
tttattatac catacataca aaca 24

<210> SEQ ID NO 300
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 300
acaactatac atgatataat attagaatgt gtgtac 36

<210> SEQ ID NO 301
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 301
tctactgtta tgagcaatta aatgacagct cagagg 36

<210> SEQ ID NO 302
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 302
tggaagacct gttaatgggc acactaggaa ttgtgt 36

<210> SEQ ID NO 303
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 303
gtatatcaaa tattagtgaa gtgtatggag acacgc 36

<210> SEQ ID NO 304
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 304
ccttgaagtg tatttaactg caccaacagg atgtat 36

<210> SEQ ID NO 305
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 305
acttggccaa ccaccccgcc gcgacccata ccaaag 36

<210> SEQ ID NO 306
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 306
gcgtgctttt tgctttgctt tgtgtgcttt tgtgtg 36

<210> SEQ ID NO 307
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 307
aagttgtaga ccctgctttt gtaaccactc ccacta 36

<210> SEQ ID NO 308
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 308
ttcctacacc tagtggttct atggttacct ctgatg 36